United States Patent
Kang et al.

(10) Patent No.: US 12,232,418 B2
(45) Date of Patent: Feb. 18, 2025

(54) ORGANIC ELECTROLUMINESCENCE DEVICE

(71) Applicant: LG DISPLAY CO., LTD., Seoul (KR)

(72) Inventors: Hyeseung Kang, Seoul (KR); Dohan Kim, Goyang-si (KR); Jungkeun Kim, Seoul (KR); Seungryong Joung, Gimpo-si (KR); Ki-Woog Song, Goyang-si (KR); Jungsoo Park, Paju-si (KR); Seongsu Jeon, Gwangmyeong-si (KR); Taewoo Jeon, Paju-si (KR)

(73) Assignee: LG DISPLAY CO., LTD., Seoul (KR)

( * ) Notice: Subject to any disclaimer, the term of this patent is extended or adjusted under 35 U.S.C. 154(b) by 1058 days.

(21) Appl. No.: 16/582,911

(22) Filed: Sep. 25, 2019

(65) Prior Publication Data

US 2020/0106026 A1    Apr. 2, 2020

(30) Foreign Application Priority Data

Oct. 2, 2018    (KR) .................. 10-2018-0117700

(51) Int. Cl.
| | |
|---|---|
| H10K 85/60 | (2023.01) |
| H10K 50/11 | (2023.01) |
| H10K 50/13 | (2023.01) |
| H10K 101/00 | (2023.01) |
| H10K 101/10 | (2023.01) |
| H10K 102/00 | (2023.01) |

(52) U.S. Cl.
CPC ....... *H10K 85/6572* (2023.02); *H10K 85/622* (2023.02); *H10K 85/626* (2023.02); *H10K 85/633* (2023.02); *H10K 85/636* (2023.02); *H10K 85/654* (2023.02); *H10K 50/11* (2023.02); *H10K 50/13* (2023.02); *H10K 85/615* (2023.02); *H10K 85/624* (2023.02); *H10K 2101/10* (2023.02); *H10K 2101/90* (2023.02); *H10K 2102/351* (2023.02)

(58) Field of Classification Search
CPC ............. H01L 51/0072; H01L 51/0054; H01L 51/0058; H01L 51/006; H01L 51/0061; H01L 51/0067; H01L 51/0052; H01L 51/0056; H01L 2251/5384; H10K 85/6572; H10K 85/654; H10K 85/636; H10K 85/633; H10K 85/622; H10K 85/626

See application file for complete search history.

(56) References Cited

U.S. PATENT DOCUMENTS

| | | |
|---|---|---|
| 9,172,046 B1 | 10/2015 | Kim et al. |
| 10,276,637 B2 | 4/2019 | Matsumoto et al. |
| 2003/0165715 A1* | 9/2003 | Yoon .................... C07D 235/18 313/506 |
| 2004/0150352 A1* | 8/2004 | Koide .................. G09G 3/3258 315/169.3 |
| 2007/0252516 A1* | 11/2007 | Kondakova ......... H01L 51/5092 428/917 |
| 2011/0127503 A1* | 6/2011 | Takahashi .............. H05B 33/10 252/301.16 |
| 2012/0223276 A1* | 9/2012 | Parham ................ C07D 403/12 544/212 |
| 2012/0326141 A1* | 12/2012 | Pflumm .............. H01L 51/5004 257/E51.026 |
| 2014/0048784 A1* | 2/2014 | Inoue .................. H01L 51/0052 548/440 |
| 2014/0167016 A1* | 6/2014 | Yoo ..................... H01L 51/5072 257/40 |
| 2015/0112064 A1 | 4/2015 | Kim et al. |
| 2015/0236261 A1* | 8/2015 | Stoessel ................ H05B 33/22 252/500 |
| 2017/0117488 A1 | 4/2017 | Ahn et al. |
| 2017/0186965 A1* | 6/2017 | Parham ............... H01L 51/0074 |
| 2018/0062103 A1 | 3/2018 | Kim et al. |
| 2018/0212149 A1 | 7/2018 | Pfister et al. |
| 2018/0301636 A1 | 10/2018 | Park et al. |
| 2021/0210699 A1 | 7/2021 | Park et al. |

FOREIGN PATENT DOCUMENTS

| | | | |
|---|---|---|---|
| CN | 103534833 A | | 1/2014 |
| CN | 107771208 A | | 3/2018 |
| JP | 2003133075 A | * | 5/2003 |

(Continued)

OTHER PUBLICATIONS

Tominaga et al., machine translation of JP-2003133075-A (2003) pp. 1-9. (Year: 2003).*

(Continued)

*Primary Examiner* — Dylan C Kershner

(74) *Attorney, Agent, or Firm* — Birch, Stewart, Kolasch & Birch, LLP

(57) ABSTRACT

An organic electroluminescence device including an anode, a cathode and a light-emission layer. The light-emission layer includes a stack of a blue light-emission layer and a red/green light concurrent-emission sub-stack. Further, the red/green light concurrent-emission sub-stack includes a stack of a red light-emission layer and a green light-emission layer. The red light-emission layer contains a red host compound including an arylamino group-substituted spiro-bisfluorene compound. Further, the green light-emission layer contains a green host compound including a mixture between a first green host compound and a second green host compound. Also, the first green host compound includes a bis-carbazole based compound, and the second green host compound includes a carbazole-based compound.

15 Claims, 13 Drawing Sheets

(56) References Cited

FOREIGN PATENT DOCUMENTS

| KR | 10-2018-0027468 A | 3/2018 |
| KR | 10-2018-0031770 A | 3/2018 |
| KR | 10-1857632 B1 | 5/2018 |
| WO | WO 2015/088249 A1 | 6/2015 |

OTHER PUBLICATIONS

Su et al., "Highly Efficient Red Electrophosphorescent Device Based on Iridium Isoquinoline Complexes: Remarkable External Quantum Efficiency Over a Wide Range of Current" Advanced Materials (2003) vol. 15, pp. 884-888. (Year: 2003).*

Thompson et al., "High-efficiency organic electrophosphorescent devices" Proceedings of SPIE, vol. 4105 (2001) pp. 119-124. (Year: 2001).*

Adachi et al., "High-efficiency red electrophosphorescence devices" Applied Physics Letters (2001) vol. 78, pp. 1622-1624. (Year: 2001).*

* cited by examiner

220

ORGANIC ELECTROLUMINESCENCE DEVICE

CROSS-REFERENCE TO RELATED APPLICATIONS

This application claims the priority of Korean Patent Application No. 10-2018-0117700 filed on Oct. 2, 2018, in the Korean Intellectual Property Office, the disclosure of which is hereby incorporated by reference in its entirety.

BACKGROUND

1. Technical Field

The present disclosure relates to an organic electroluminescence device.

2. Description of the Related Art

An organic electroluminescence device is a self-light-emission device that converts electrical energy into light energy using an organic material. Generally, in the organic electroluminescence device, an organic material layer is placed between an anode and a cathode.

When a voltage is applied between the anode and the cathode, holes are injected from the anode into the organic material layer, and electrons are injected into the organic material layer from the cathode. When the injected holes and electrons encounter each other, excitons are formed. Light emission then occurs when the exciton falls to a ground state.

In order to increase the efficiency and stability of the organic electroluminescence device, the organic material layer may have a multi-layered structure composed of different materials. For example, the organic material layer may include a hole injection layer, a hole transport layer, a light-emission layer, an electron transport layer, and an electron injection layer.

SUMMARY

A purpose of the present disclosure is to provide a white-light organic electroluminescence device with improved color purity and color reproducibility.

The purposes of the present disclosure are not limited to the above-mentioned purposes. Other purposes and advantages of the present disclosure, as not mentioned above, may be understood from the following descriptions and more clearly understood from the embodiments of the present disclosure. Further, it will be readily appreciated that the objects and advantages of the present disclosure may be realized by features and combinations thereof as disclosed in the claims.

The present disclosure provides an organic electroluminescence device including a light-emission layer that includes a stack of a blue light-emission layer and red/green light concurrent-emission sub-stacks. The red/green light concurrent-emission sub-stack includes a stack of a red light-emission layer and a green light-emission layer. The green light-emission layer is closer to the cathode than the red light-emission layer is. In other words, the organic electroluminescence device includes an anode, a cathode and the light-emission layer, wherein the green light-emission layer is placed between the red light-emission layer and the cathode.

The red light-emission layer contains a red host compound represented by Chemical Formula 1 and a red phosphorescent dopant.

The green light-emission layer contains a green host compound and a green phosphorescent dopant. The green host compound includes a mixture of a first green host compound represented by Chemical Formula 2 and a second green host compound represented by Chemical Formula 3:

<Chemical Formula 1>

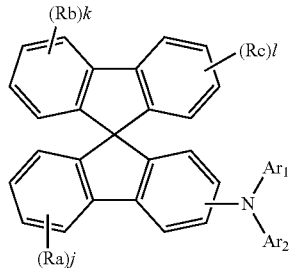

In the Chemical Formula 1, each of Ra, Rb and Rc independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C15 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 1, each of j, k, and l independently denotes an integer of 1 to 4.

In the Chemical Formula 1, each of $Ar_1$ and $Ar_2$ independently represents one selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted dibenzofuranyl group and a substituted or unsubstituted dibenzothiophenyl group.

<Chemical Formula 2>

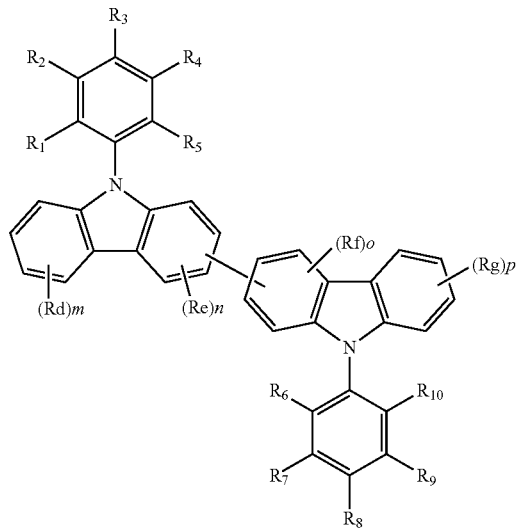

In the Chemical Formula 2, each of Rd, Re, Rf and Rg independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C15 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 2, each of m and p independently denotes an integer of 1 to 4. Each of n and o independently denotes an integer of 1 to 3.

In the Chemical Formula 2, each of $R_1$, $R_2$, $R_3$, $R_4$, $R_5$, $R_6$, $R_7$, $R_8$, $R_9$, and $R_{10}$ independently represents one selected from the group consisting of hydrogen, deuterium, halogen, a substituted or unsubstituted C1 to C6 alkyl group, a substituted or unsubstituted C6 to C15 aryl group, a substituted or unsubstituted carbazole group, a substituted or unsubstituted dibenzofuranyl group, and a substituted or unsubstituted dibenzothiophenyl group.

<Chemical Formula 3>

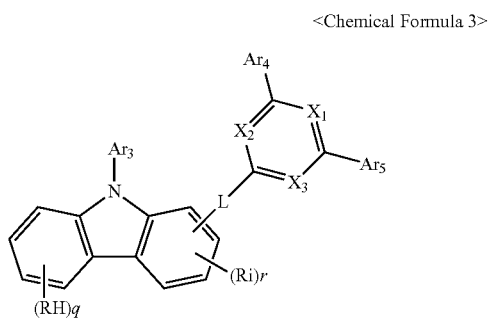

In the Chemical Formula 3, each of Rh and Ri independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C15 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 3, q denotes an integer from 1 to 4, and r denotes an integer from 1 to 3.

In the Chemical Formula 3, each of $Ar_3$, $Ar_4$ and $Ar_5$ independently represents one selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted dibenzofuranyl group, and a substituted or unsubstituted dibenzothiophenyl group.

In the Chemical Formula 3, L represents one selected from the group consisting of a single bond, a phenyl group, a naphthyl group, and a pyridyl group.

In the Chemical Formula 3, each of $X_1$, $X_2$, and $X_3$ independently represents N or CH, and at least two of $X_1$, $X_2$, and $X_3$ represent N.

Details of other embodiments are included in detailed descriptions and drawings.

The present disclosure provides a white-light organic electroluminescence device that meets color coordinates required for high color purity and high color reproducibility.

Further specific effects of the present disclosure as well as the effects as described above will be described in conjunction with specific details for carrying out the present disclosure.

BRIEF DESCRIPTION OF DRAWINGS

The present invention will become more fully understood from the detailed description given hereinbelow and the accompanying drawings, which are given by illustration only, and thus are not limitative of the present invention, and wherein.

DETAILED DESCRIPTION

Figure 1:
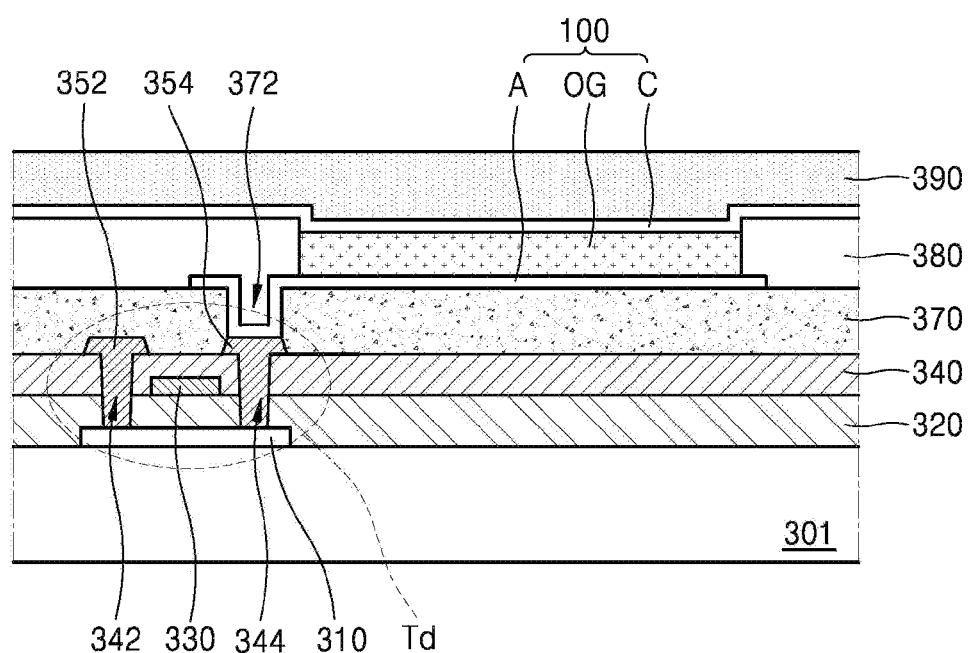
FIG. 1 is a schematic cross-sectional view of an organic electroluminescence display device.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

For simplicity and clarity of illustration, elements in the figures are not necessarily drawn to scale. The same reference numbers in different figures denote the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expressions such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, a "Ca to Cb" hydrocarbon group is defined as a hydrocarbon group or a hydrocarbon derivative group having a carbon number of "a" or greater and "b" or smaller. A phrase "a to b" is defined as being a or greater and b or smaller.

As used herein, in a phase "substituted" or "unsubstituted", the term "substituted" means that at least one hydrogen of a hydrocarbon compound or hydrocarbon derivative is replaced with a hydrocarbon group, a hydrocarbon derivative group, halogen or a cyano group (—CN) or the like. The term "unsubstituted" means that at least one hydrogen of a hydrocarbon compound or hydrocarbon derivative is not replaced with a hydrocarbon group, a hydrocarbon derivative group, halogen or a cyano group (—CN) or the like. Examples of the hydrocarbon group or the hydrocarbon derivative group may include C1 to C6 alkyl, C2 to C6 alkenyl, C2 to C6 alkynyl, C6 to C15 aryl, C1 to C6 alkyl C6 to C15 aryl, C6 to C15 aryl C1 to C6 alkyl, C1 to C6 alkylamino, C6 to C15 arylamino, C1 to C6 alkylidene, and the like, but not limited thereto.

Hereinafter, an organic electroluminescence display device according to one embodiment of the present disclosure will be described with reference to FIG. 1. In particular, FIG. 1 shows a schematic cross-section of an organic electroluminescence display device 1000.

As shown, the organic electroluminescence display device 1000 contains a display region in which pixels are arranged in a matrix form and a non-display region disposed around the display region. The display region refers to an area in which an image or information generated from the organic electroluminescence display device 1000 can be viewed by the viewer. The non-display region refers to an area where the image or information generated from the organic electroluminescence display device 1000 cannot be viewed by the viewer, and is generally referred to as a bezel area. Further, the organic electroluminescence display device 1000 includes a plurality of pixels. FIG. 1 shows one pixel among a plurality of pixels provided in the organic electroluminescence display device 1000.

The organic electroluminescence display device 1000 may include a circuit substrate 301 including an organic electroluminescence device 100 and a thin-film transistor Td on a pixel basis. The organic electroluminescence device 100 is electrically connected to the thin-film transistor Td and generates light-emission. In the organic electroluminescence device 100, each pixel contains an anode A, a cathode C, and an organic material layer OG. The organic material layer OG is disposed between the anode A and the cathode C. When the organic electroluminescence display device 1000 has a front light-emission type structure in which an image is rendered toward the cathode C, the cathode C may be embodied as a light transmitting type electrode while the anode A may be embodied as a reflective electrode. When the organic electroluminescence display device 1000 has a rear light-emission type structure in which an image is rendered toward the anode A, the anode A may be embodied as a light transmission type electrode, while the cathode C may be embodied as a reflective electrode.

Further, the light transmission type electrode may be made of a light-transmitting metal oxide such as ITO, IZO, or ZnO. The reflective electrode may be made of a metal such as Ag, Mg, Al, Pt, Pd, Au, Ni, Nd, Ir, Cr, Li and Ca, for example.

The organic electroluminescence display device 1000 may further include a pixel-defining film 380 functioning to define a pixel. The pixel-defining film 380 may be disposed between the anode A and the cathode C and on top of the thin-film transistor Td. The pixel-defining film 380 may be partially removed to expose a portion of the anode A. In the partially removed region of the pixel-defining film 380 where the portion of the anode A is exposed, an organic material layer OG may be disposed therein.

The organic electroluminescence display device 1000 may further include an encapsulation layer 390. The encapsulation layer 390 may be disposed on the cathode C to prevent water or the like from entering the organic material layer OG from the outside.

In addition, the circuit substrate 301 may include a driving circuit disposed on the substrate 301. Specifically, the driving circuit may include a driving thin-film transistor Td disposed on the substrate 301. Also, a switching thin-film transistor or the like may be disposed on the substrate 301 to constitute the circuit substrate. Further, the substrate 301 can be a transparent substrate such as a glass substrate, a transparent polymer resin substrate, or the like. A buffer layer may also be optionally interposed between the substrate 301 and the driving thin-film transistor Td to improve a flatness of the substrate 301. The buffer layer may be composed of an inorganic oxide such as silicon oxide or an inorganic nitride such as silicon nitride.

In addition, the driving thin-film transistor Td is disposed on the substrate 301 and may include a semiconductor layer 310, a first insulating film 320, a gate electrode 330, a second insulating film 340, a source electrode 352, and a drain electrode 354.

As shown, the semiconductor layer 310 is disposed on the substrate 301 in a first region thereof. For example, the semiconductor layer 310 may be made of oxide semiconductor material or polycrystalline silicon. When the semiconductor layer 310 is made of polycrystalline silicon, the semiconductor layer 310 may include an active layer and a channel region disposed at each of both sides of the active layer.

In addition, the first insulating film 320 is disposed between the gate electrode 330 and the substrate 301. A portion of the first insulating film 320 is disposed on the semiconductor layer 310 in the first region of the substrate 301 while a remaining portion of the first insulating film 320 is disposed on the substrate 301 in a second region of the substrate 301. The first region and the second region of the substrate 301 may be individual. As used herein, the first region of the substrate 301 may be defined as a region in which the semiconductor layer 310 is formed. The first insulating film 320 may be made of an inorganic oxide such as silicon oxide or an inorganic nitride such as silicon nitride.

Further, the gate electrode 330 is disposed on the first insulating film 320 and overlaps the semiconductor layer 310 in the first region of the substrate 301. The gate electrode 330 may also be made of an aluminum-based metal such as aluminum (Al) and aluminum alloy, or a silver-based metal such as silver (Ag) and sliver alloy, a copper based metal such as copper (Cu) and copper alloy, a molybdenum based metal such as molybdenum (Mo) and molybdenum alloy, chromium (Cr), titanium (Ti), tantalum (Ta), or the like.

The second insulating film 340 is disposed on the first insulating film 320 and the gate electrode 330. Specifically, a portion of the second insulating film 340 is disposed on the first insulating film 320, while a remaining portion of the second insulating film 340 is disposed on the gate electrode 330. The second insulating film 340 may be made of an inorganic oxide such as silicon oxide or an inorganic nitride such as silicon nitride as in the first insulating film 320.

As shown, the source electrode 352 and the drain electrode 354 are disposed on the second insulating film 340 and are disposed apart from each other on the second insulating film 340. Further, the source electrode 352 and the drain electrode 354 are connected to the semiconductor layer 310 via contact holes 342 and 344 defined in the first insulating film 320 and the second insulating film 340 respectively. Also, each of the source electrode 352 and the drain electrode 354 may be made of a metal such as Al, Ag, Mg, Mo, Ti or W.

The organic electroluminescence display device 1000 may further include a passivation layer 370 disposed between the circuit substrate and the organic electroluminescence device 100. As shown, the passivation layer 370 may have a contact hole 372 defined therein for connecting the anode A and the drain electrode 354 with each other.

The organic electroluminescence device 100 may be embodied as a white organic electroluminescence device that emits white light using light-beams of three primary colors. For example, the organic electroluminescence device 100 may be configured to have an RGB direct stacked structure, a quantum well structure, or a multilayered light emitting structure. For example, FIG. 2 shows a schematic diagram of an organic electroluminescence device 200 of an exemplary multilayered light emitting structure.

Figure 2:
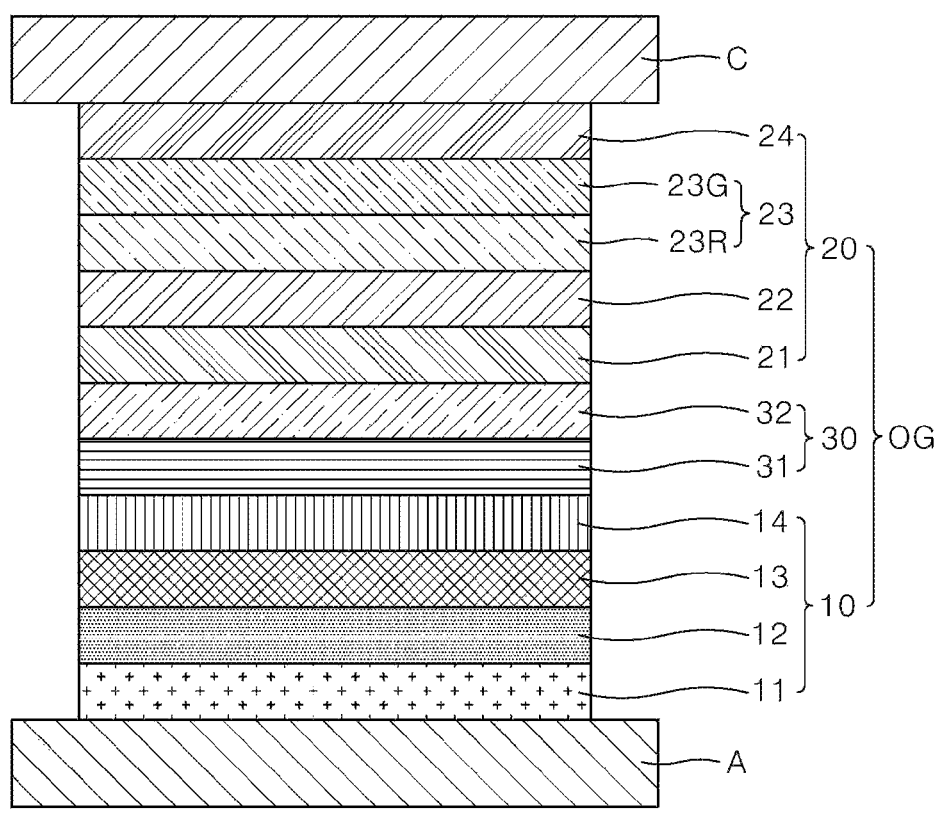
FIG. 2 is a schematic diagram of an embodiment of an organic electroluminescence device having multilayer light emitting structures.

Referring to FIG. 2, the organic electroluminescence device 200 includes an anode A, a cathode C, and an organic material layer OG. The organic material layer OG is placed between the anode A and cathode C and may include a first stack 10, a second stack 20, and a charge generation layer 30. The charge generation layer 30 is disposed between the first stack 10 and the second stack 20. Also, the first stack 10 is disposed between the anode A and the charge generation layer 30, while the second stack 20 is disposed between the cathode C and the charge generation layer 30.

The first stack 10 includes a hole transport layer 12, a blue light-emission layer 13, and an electron transport layer 14. Also, the second stack 20 includes a hole transport layer 22, a red/green light concurrent-emission sub-stack 23, and an electron transport layer 24. The red/green light concurrent-emission sub-stack 23 includes a stack of a red light-emitting layer 23R and a green light-emitting layer 23G. The green light-emitting layer 23G is closer to the cathode C than the red light-emitting layer 23R is. The blue light-emitting layer 13 may be disposed between the anode A and the red light-emitting layer 23R of the red/green concurrent light-emitting layer 23. Further, the green light-emission layer 23G of the red/green light concurrent-emission sub-stack 23 may be disposed between the cathode C and the red light-emission layer 23R of the red/green light concurrent-emission sub-stack 23.

The first stack 10 may have a structure in which the hole transport layer 12, the blue light-emission layer 13, and the electron transport layer 14 are sequentially stacked in a direction from the anode A to the second stack 20. The second stack 20 may have a structure in which the hole transport layer 22, the red/green light concurrent-emission sub-stack 23, and the electron transport layer 24 are sequentially stacked in a direction from the first stack 10 to the cathode C.

In addition, the first stack 10 may further include a hole injection layer 11 disposed between the anode A and the hole transport layer 12. Also, the first stack 10 may further include a first functional layer having both of a hole injection function and a hole transport function, a second functional layer having both of an electron transport function and an electron injection function, an electron blocking layer, a hole blocking layer, a buffer layer, and an electron injection layer. In this case, a first functional layer, a buffer layer and an electron blocking layer may be sequentially stacked between the hole transport layer 12 and the blue light-emitting layer 13 and in a direction from the hole transport layer 12 to the blue light-emission layer 13. Further, a hole blocking layer may be disposed between the blue light-emitting layer 13 and the electron transport layer 14. Further, an electron injection layer and a second functional layer may be sequentially stacked between the electron transport layer 14 and the n-type charge generation layer 31 of the charge generation layer 30 and in a direction from the electron transport layer 14 to the n-type charge generation layer 31.

Also, the second stack 20 may further include a hole injection layer 21 disposed between the charge generation layer 30 and the hole transport layer 22. The second stack 20 may further include a first functional layer having both of a hole injection function and a hole transport function, a second functional layer having both of an electron transport function and an electron injection function, an electron blocking layer, a hole blocking layer, a buffer layer, and an electron injection layer. In this instance, a first functional layer, a buffer layer and an electron blocking layer can be sequentially stacked between the hole transport layer 22 and the red/green light concurrent-emission sub-stack 23 and in a direction from the hole transport layer 22 to the red/green light concurrent-emission sub-stack 23. Further, a hole blocking layer can be disposed between the red/green light concurrent-emission sub-stack 23 and the electron transport layer 24. Further, an electron injection layer and a second functional layer can be sequentially stacked between the electron transport layer 24 and the cathode C and in a direction from the electron transport layer 14 to the cathode C.

In addition, the charge generation layer 30 includes the n-type charge generation layer 31 and the p-type charge generation layer 32. In more detail, the n-type charge generation layer 31 is disposed between the first stack 10 and the second stack 20. For example, the n-type charge generation layer 31 may be disposed between one of the electron transport layer 14 and the electron injection layer of the first stack 10 and one of the hole injection layer 21 and the hole transport layer 22 of the second stack 20. The p-type charge generation layer 32 is disposed between the n-type charge generation layer 31 and the second stack 20. For example, the p-type charge generation layer 32 may be disposed between one of the hole injection layer 21 and the hole transport layer 22 of the second stack 20 and the n-type charge generation layer 31.

The hole injection layers 11 and 21 serve to facilitate hole injection. In one example, each of the hole injection layers 11 and 21 may contain at least one selected from a group of consisting of HAT-CN, CuPu (cupper phthalocyanine), PEDOT (poly(3,4-ethylenedioxythiophene). PEDOT:PSS (poly(3,4)-ethylenedioxythiophene)poly(styrenesulfonate), PANI (polyaniline), and NPD (N,N-dinaphthyl-N,N'-diphenyl benzidine).

The hole transport layers 12 and 22 serve to facilitate transport of holes. In one example, each of the hole transport layers 12 and 22 may contain at least one selected from a group of consisting of NPD (N,Ndinaphthyl-N,N'-diphenyl-benzidine), TPD (N,N'-bis-(3-methylphenyl)-N,N'-bis-(phenyl)-benzidine), s-TAD, and MTDATA (4,4',4"-tris(N-3-methylphenyl-N-phenyl-amino)-triphenylamine).

The electron transport layers 14 and 24 serve to facilitate the transport of electrons. In one example, each of the electron transport layers 14 and 24 may contain at least one selected from a group of consisting of Alq3 (tris(8-hydroxyquinolino)aluminum), PBD, TAZ, spiro-PBD, BAlq and SAlq.

The electron injection layer serves to facilitate the injection of electrons. In one example, the electron injection layer may contain at least one selected from a group of consisting of Alq3 (tris(8-hydroxyquinolino)aluminum), PBD, TAZ, spiro-PBD, BAlq and SAlq.

The charge generation layer 30 controls a charge balance between the first stack 10 and the second stack 20. In particular, the charge generation layer 30 allows the light emitting efficiency of the organic electroluminescence device 200 to be increased and allows the lifetime of the device 200 to be improved. The n-type charge generation layer 31 is formed by doping an electron transport material with an alkali metal or an alkaline earth metal. In this connection, the electron transport material may have a fused aromatic ring including a hetero ring, and examples of the alkali metal or alkaline earth metal may include lithium (Li), sodium (Na), magnesium (Mg), calcium (Ca), cesium (Cs) and the like. The p-type charge generation layer 32 contains a hole transport material.

Further, the blue light-emission layer 13 contains a blue host compound and a blue dopant compound. An example of the blue host compound includes an anthracene based compound, and an example of the blue dopant compound includes a pyrene based dopant compound or a boron-containing dopant compound.

In addition, the organic electroluminescence device 200 can render a white light using lights of the three primary colors emitted from the blue light-emission layer 13 and the red/green light concurrent-emission sub-stack 23. In more detail, a color coordinate of the white light is determined by a color coordinate of blue light from the blue light-emission layer 13 and color coordinates of red light and green light from the red/green light concurrent-emission sub-stack 23. However, when the mobility of holes and mobility of electrons injected into the red/green light concurrent-emission sub-stack 23 are not balanced, it is difficult to render white light using the three primary colors of light beams emitted from the blue light-emission layer 13 and the red/green light concurrent-emission sub-stack 23.

For example, in order for the red/green light concurrent-emission sub-stack 23 to emit yellow-green light, the mobility of holes and the mobility of electrons as introduced into the red/green light concurrent-emission sub-stack 23 must be balanced. When the mobility of holes entering the red/green light concurrent-emission sub-stack 23 is higher than the mobility of electrons entering the red/green light concurrent-emission sub-stack 23, the red/green light concurrent-emission sub-stack 23 emit greenish-yellow light having a higher green concentration. In contrast, when the mobility of holes entering the red/green light concurrent-emission sub-stack 23 is lower than the mobility of electrons entering the red/green light concurrent-emission sub-stack 23, the red/green light concurrent-emission sub-stack 23 emit reddish-yellow light having a higher red concentration.

Because, it is very difficult to balance the hole mobility and electron mobility in the red/green light concurrent-emission sub-stack 23, it is very difficult to render the white light using the blue light-emission layer 13 and the red/green light concurrent-emission sub-stack 23.

There is a direct correlation between the charge mobility and the molecular structure of the host material. In particular, the present inventors have found that the hole mobility and electron mobility in the red/green light concurrent-emission sub-stack 23 can be balanced using the organic coupling relationship between the host material used for the red light-emitting layer 23R and the host material used for the green light-emitting layer 23G.

In more detail, the red light-emission layer 23R contains a red host compound represented by a following Chemical Formula 1 and a red phosphorescent dopant:

<Chemical Formula 1>

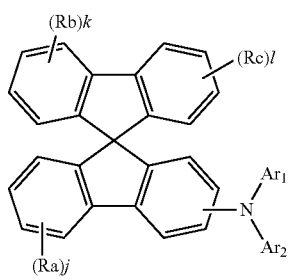

In the Chemical Formula 1, each of Ra, Rb and Rc independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C15 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 1, each of j, k, and l independently denotes an integer of 1 to 4. In the Chemical Formula 1, each of $Ar_1$ and $Ar_2$ independently represents one selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted dibenzofuranyl group and a substituted or unsubstituted dibenzothiophenyl group.

For example, examples of the red host compound may include following RH-1 to RH-12. The red host compound may include at least one of following RH-1 to RH-12.

RH-1

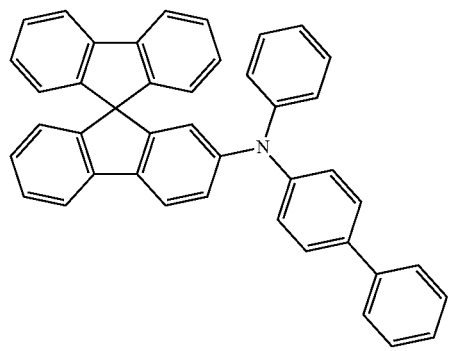

RH-2

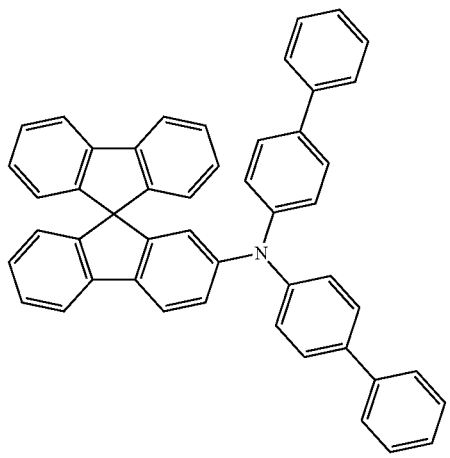

RH-3

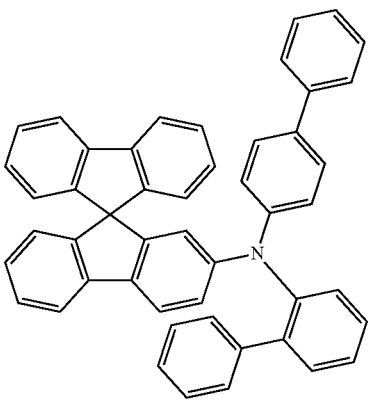

RH-4

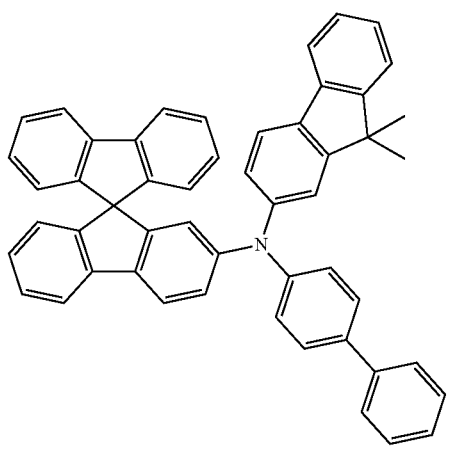

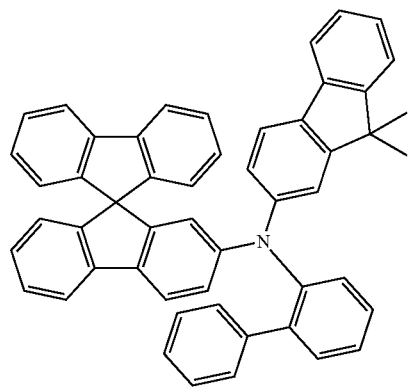
RH-5
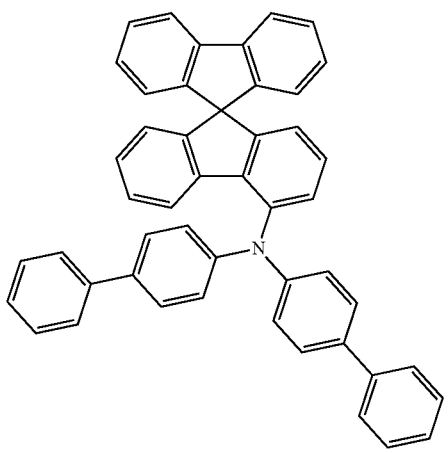
RH-8
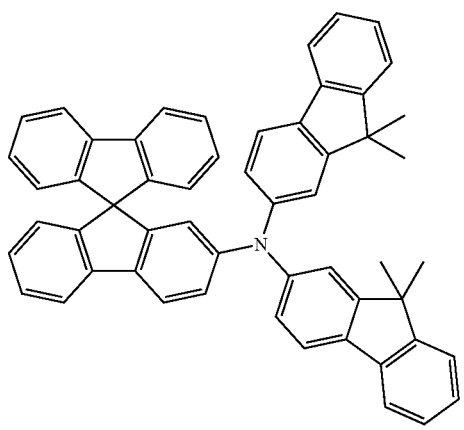
RH-6
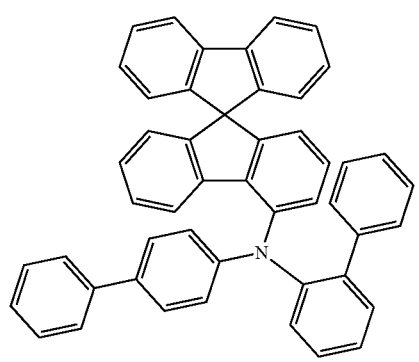
RH-9
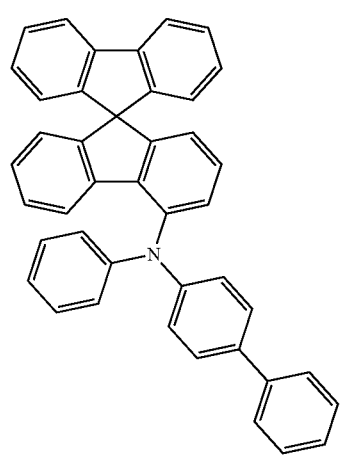
RH-7
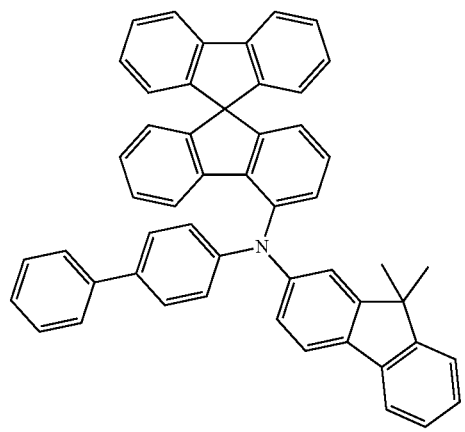
RH-10

RH-11

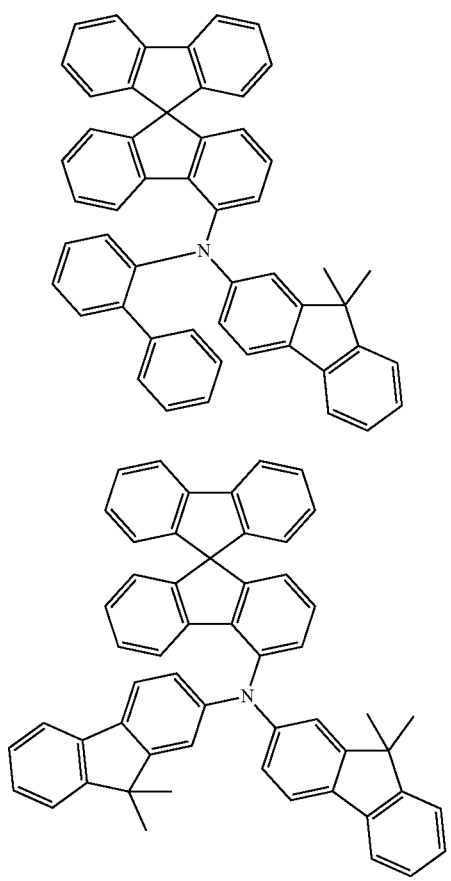

RH-12

The green light-emission layer 23G includes a green host compound and a green phosphorescent dopant. Further, the green host compound includes a mixture of a first green host compound represented by a following Chemical Formula 2 and a second green host compound represented by a following Chemical Formula 3.

<Chemical Formula 2>

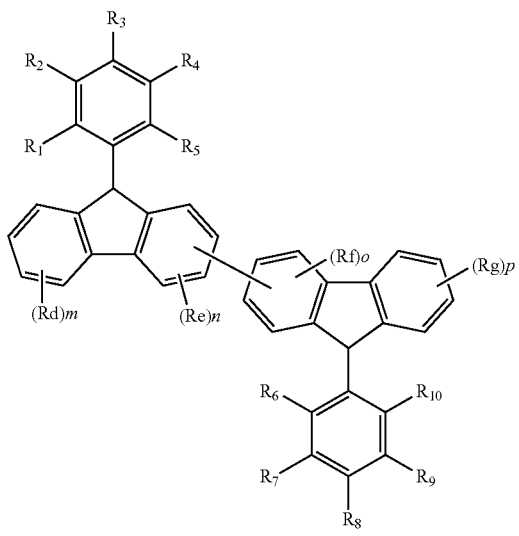

In the Chemical Formula 2, each of Rd, Re, Rf and Rg independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C15 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 2, each of m and p independently denotes an integer of 1 to 4. Each of n and o independently denotes an integer of 1 to 3. In the Chemical Formula 2, each of $R_1$, $R_2$, $R_3$, $R_4$, $R_5$, $R_6$, $R_7$, $R_8$, $R_9$, and $R_{10}$ independently represents one selected from the group consisting of hydrogen, deuterium, halogen, a substituted or unsubstituted C1 to C6 alkyl group, a substituted or unsubstituted C6 to C15 aryl group, a substituted or unsubstituted carbazole group, a substituted or unsubstituted dibenzofuranyl group, and a substituted or unsubstituted dibenzothiophenyl group.

For example, examples of the first green host compound include following GHA-1 to GHA-44. The first green host compound may include at least one of the following GHA-1 to GHA-44.

GHA-1

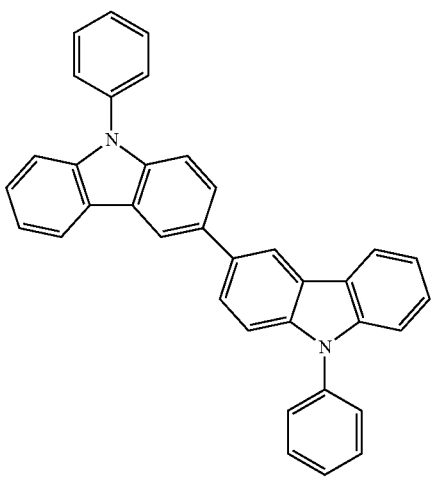

GHA-2
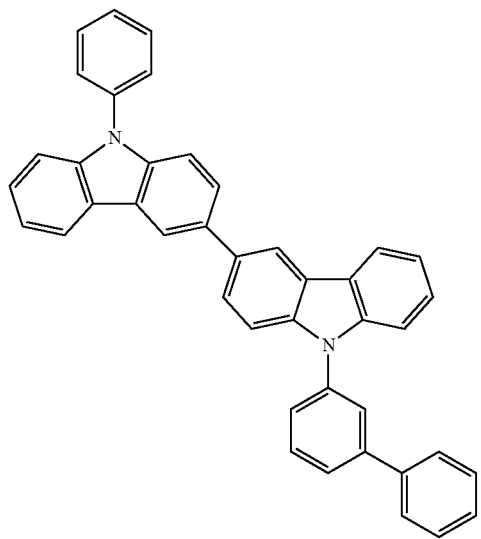
GHA-4
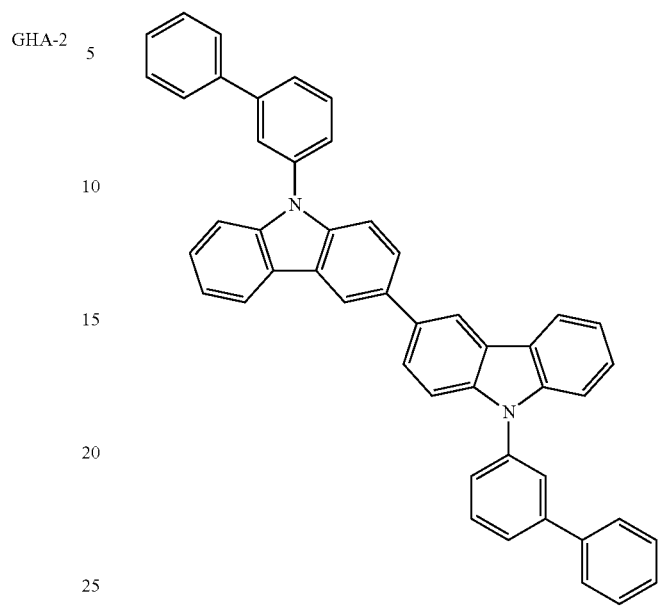
GHA-3
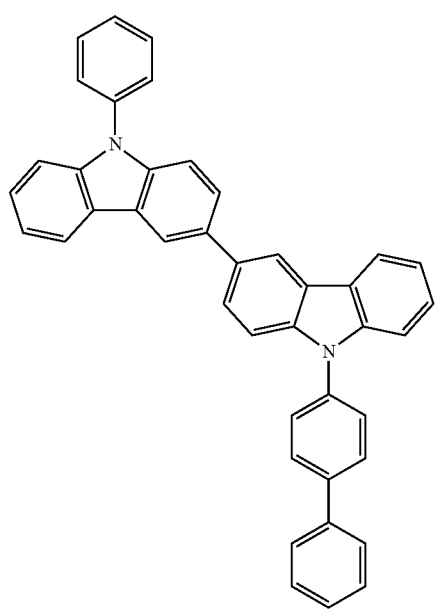
GHA-5
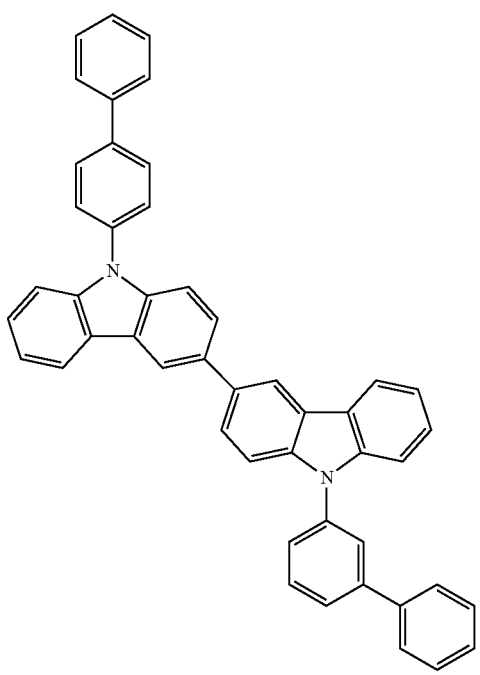

GHA-6
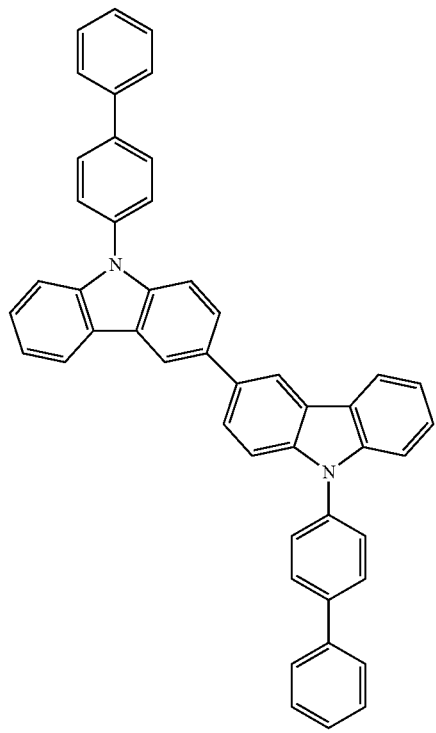
GHA-8
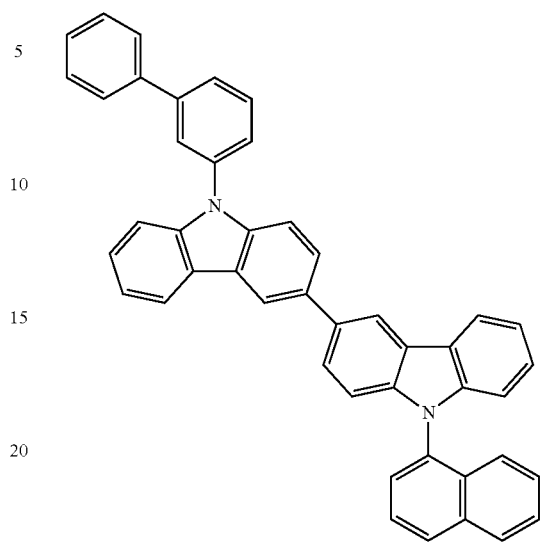
GHA-7
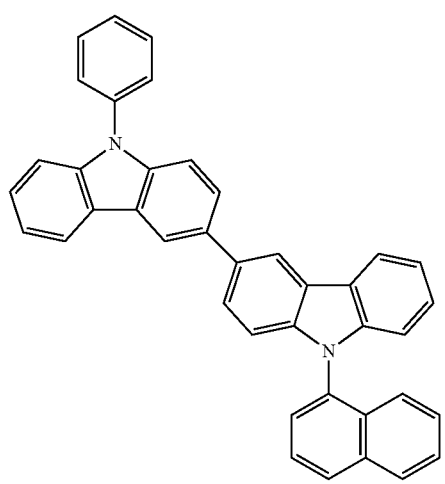
GHA-9
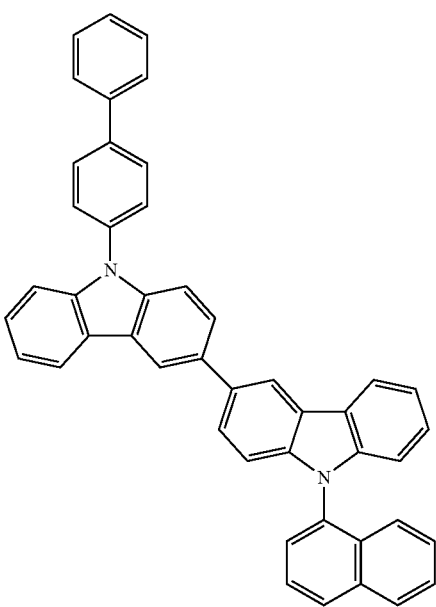

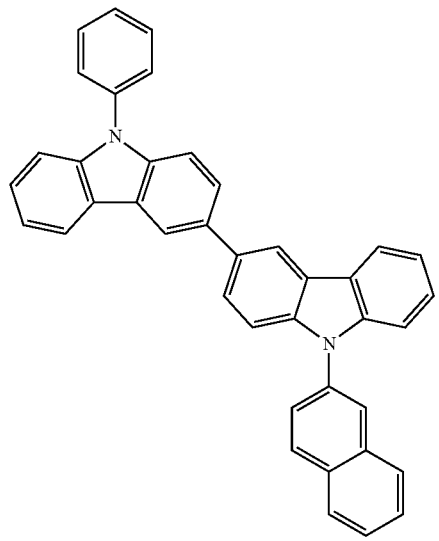
GHA-10
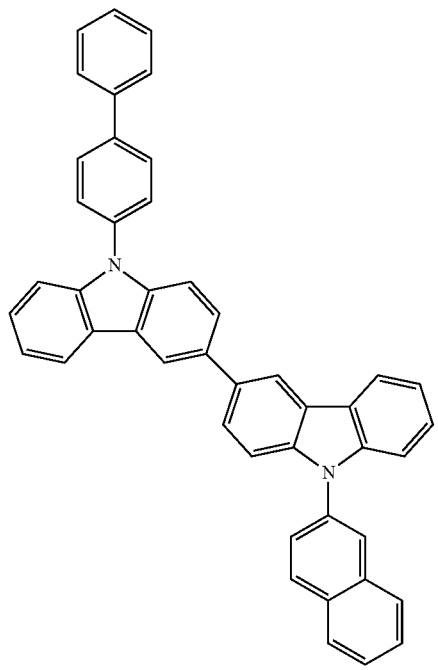
GHA-12
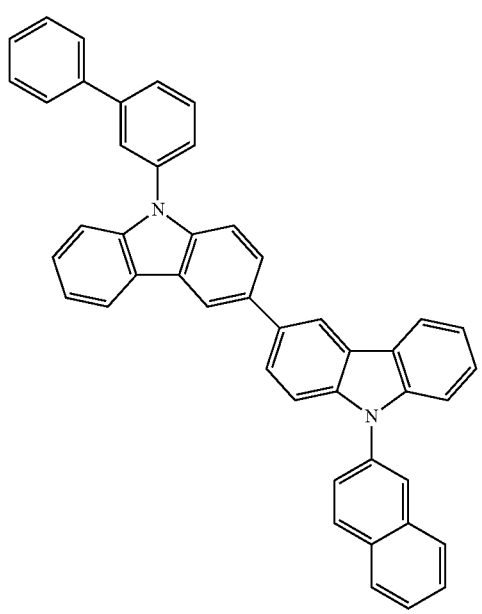
GHA-11
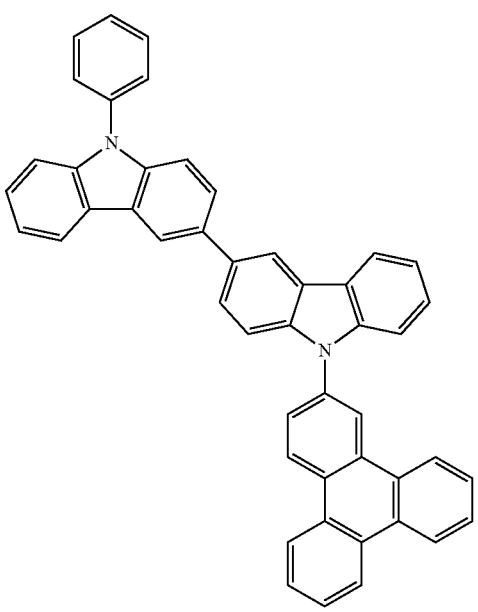
GHA-13

GHA-14
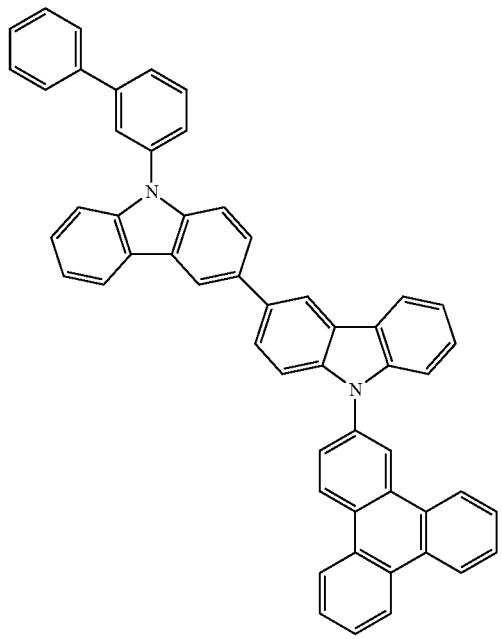
GHA-15
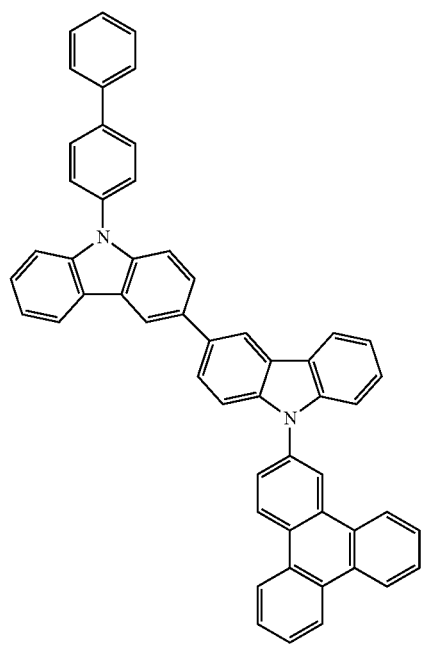
GHA-16
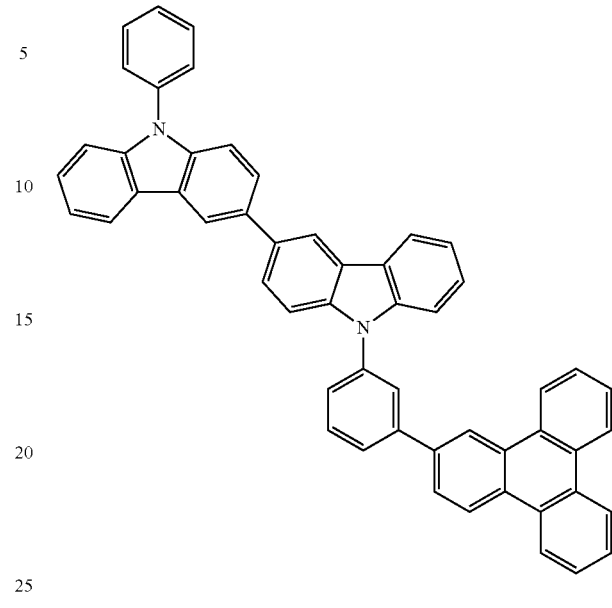
GHA-17
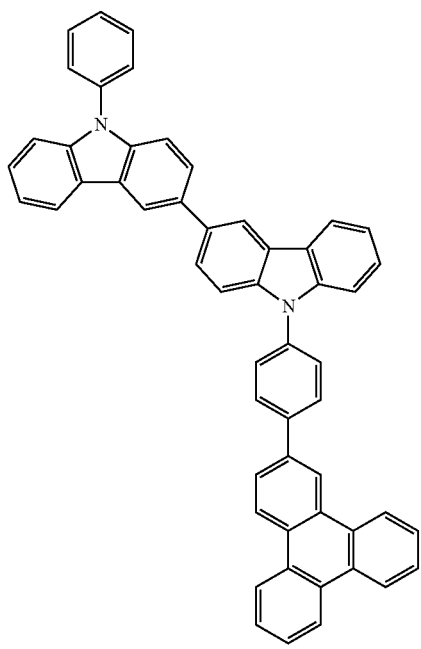

GHA-18
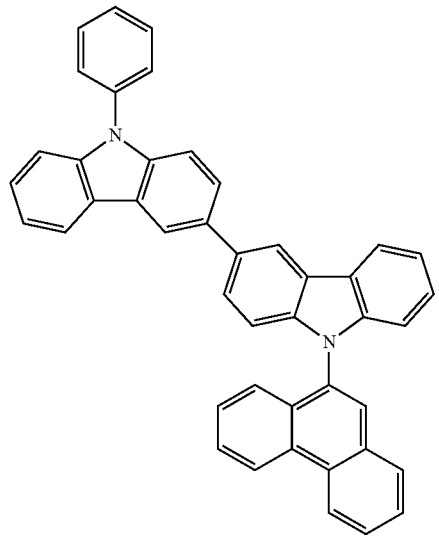
GHA-19
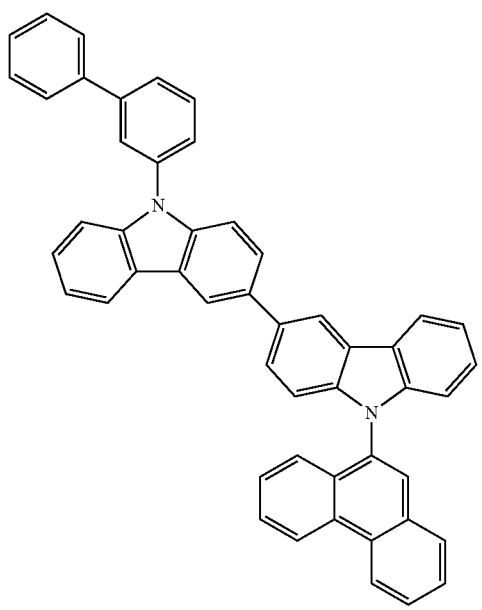
GHA-20
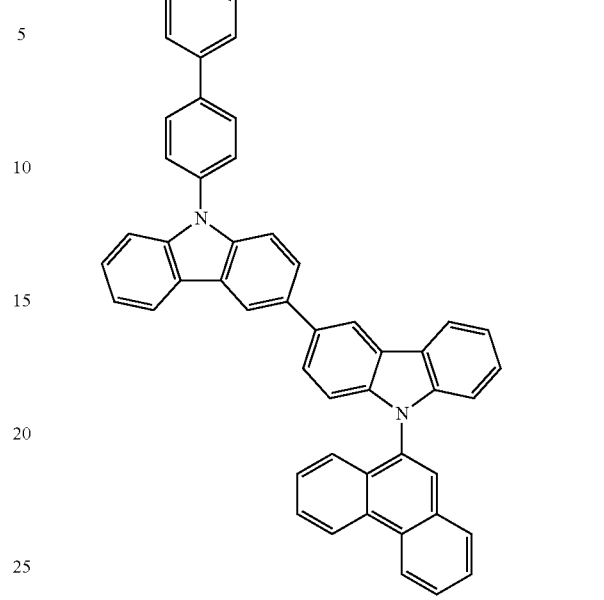
GHA-21

GHA-22
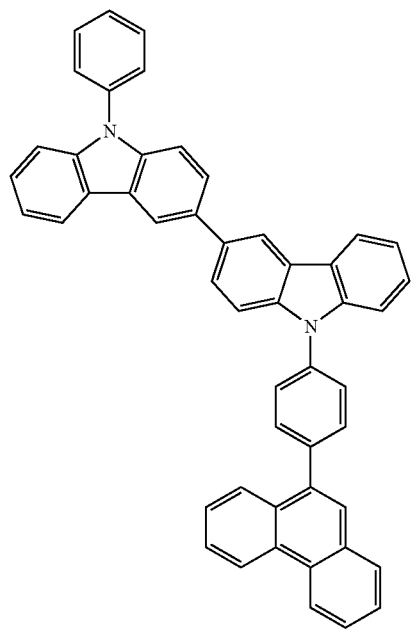
GHA-23
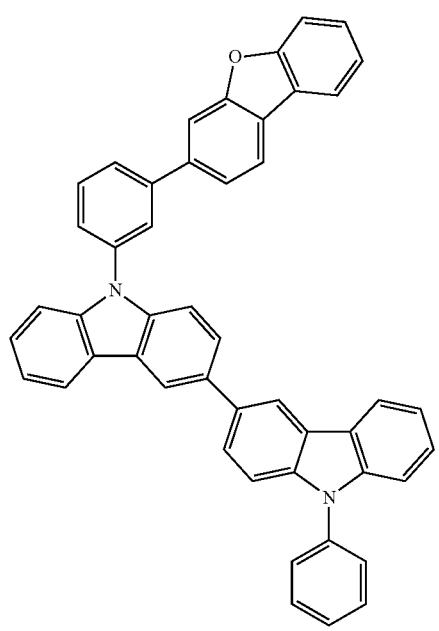
GHA-24
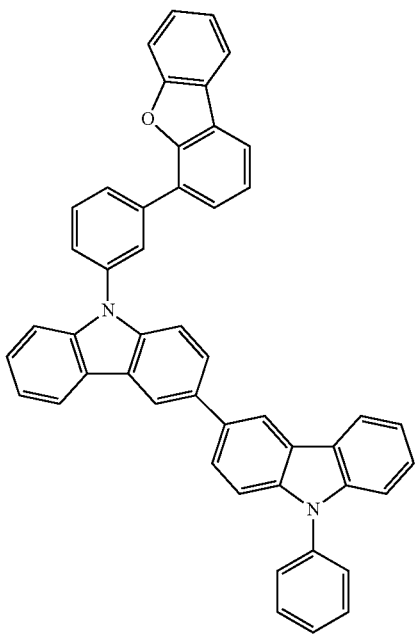
GHA-25
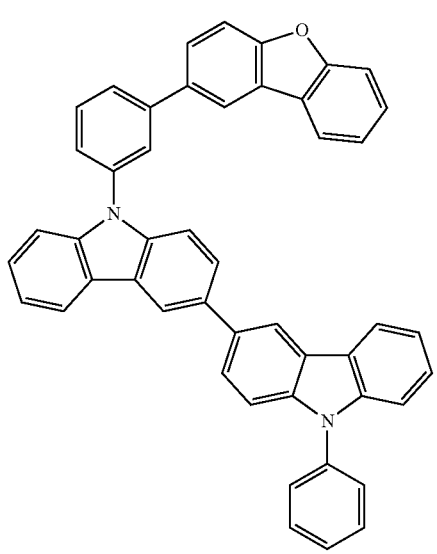

GHA-26
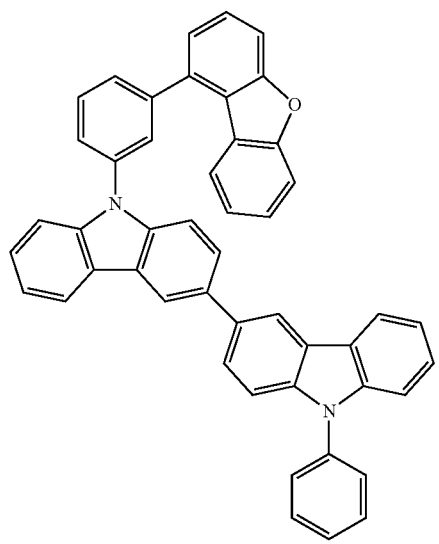
GHA-28
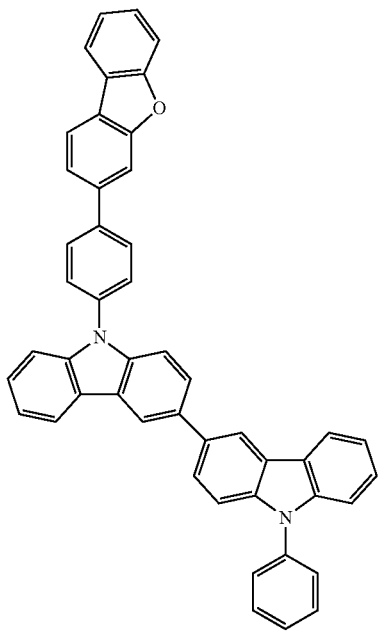
GHA-27
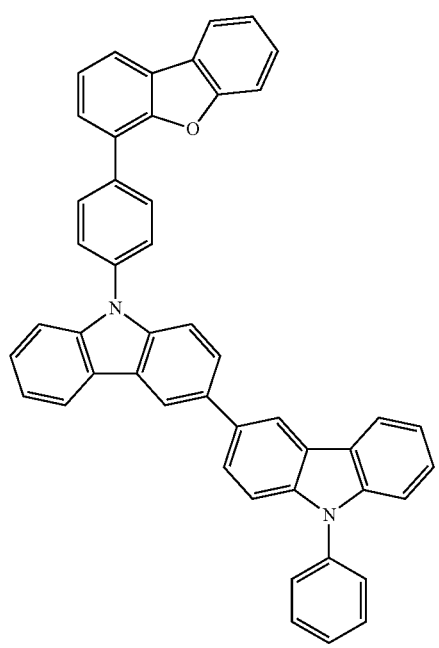
GHA-29
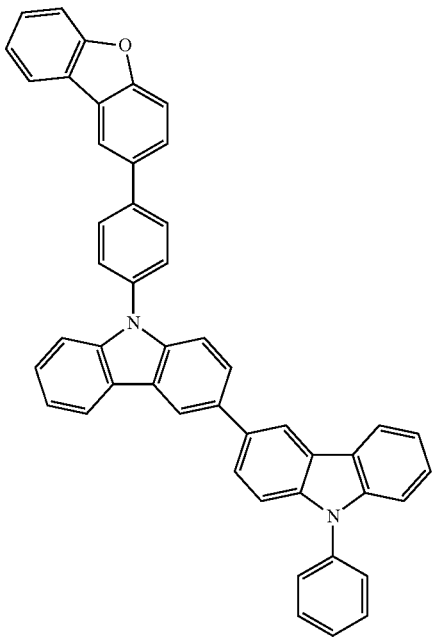

GHA-30
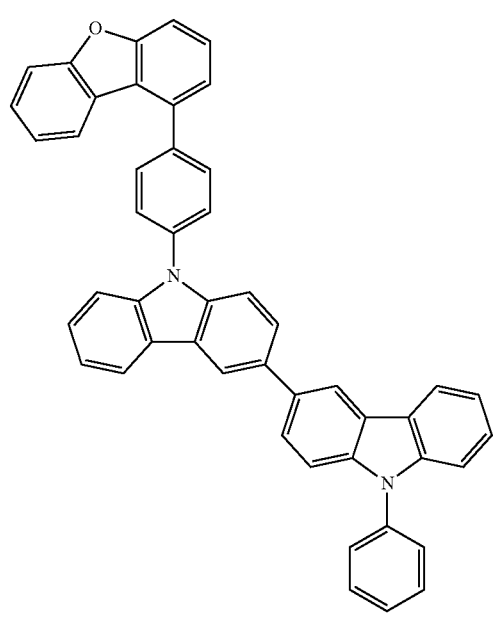
GHA-32
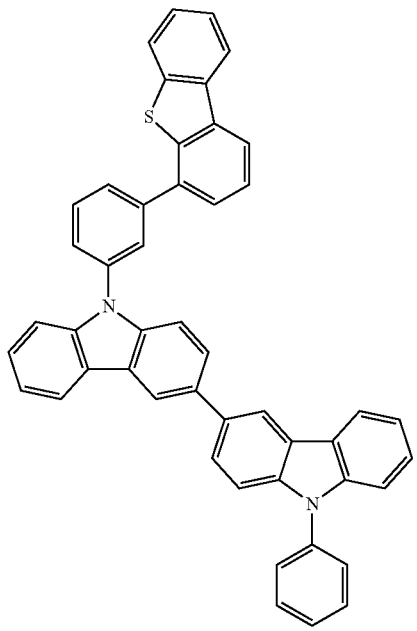
GHA-31
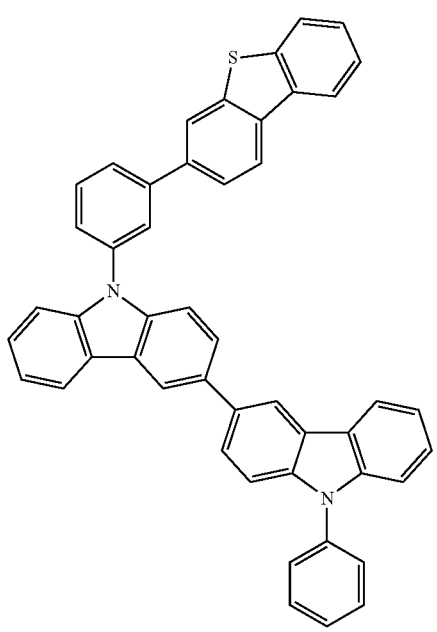
GHA-33
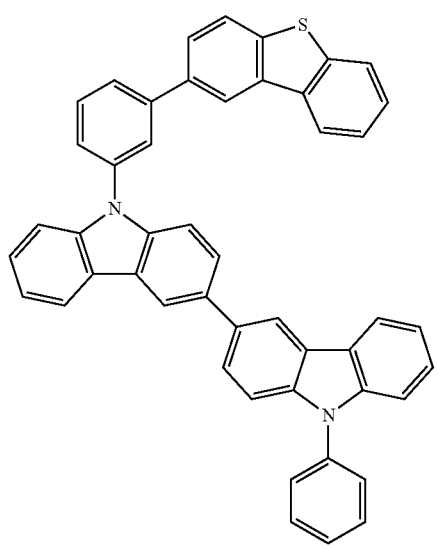

GHA-34
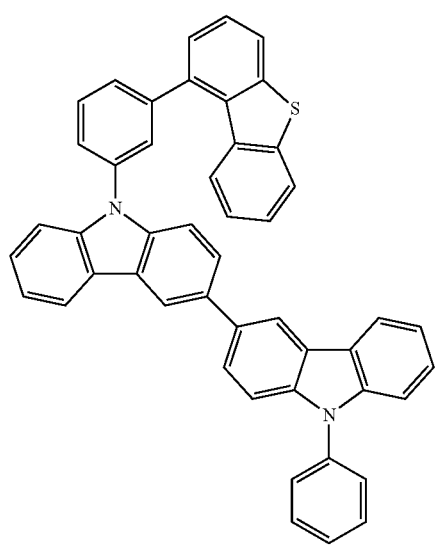
GHA-36
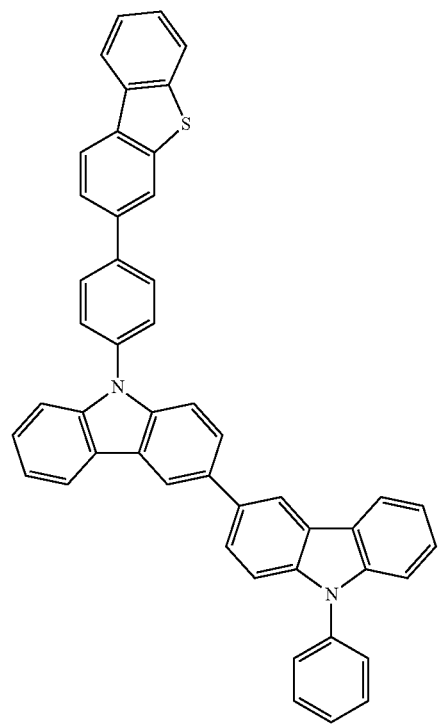
GHA-35
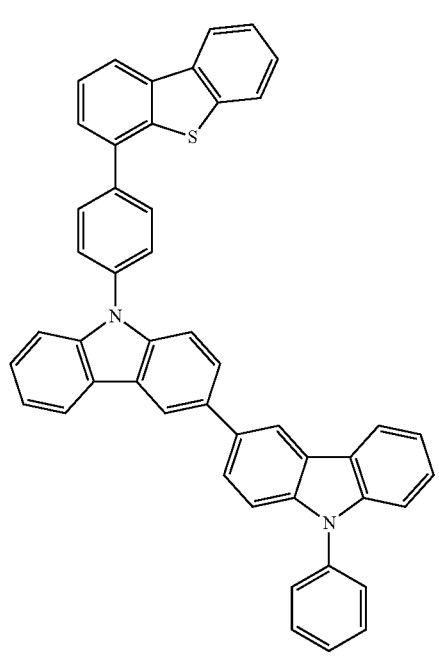
GHA-37
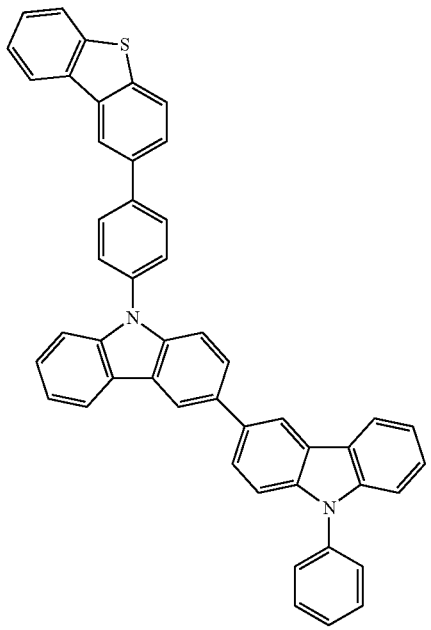

GHA-38
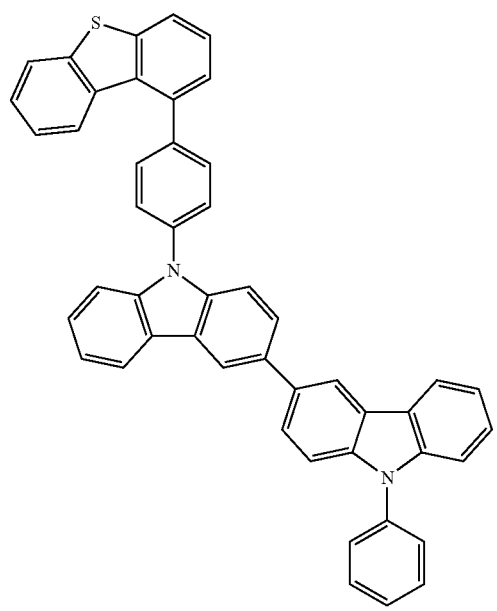
GHA-40
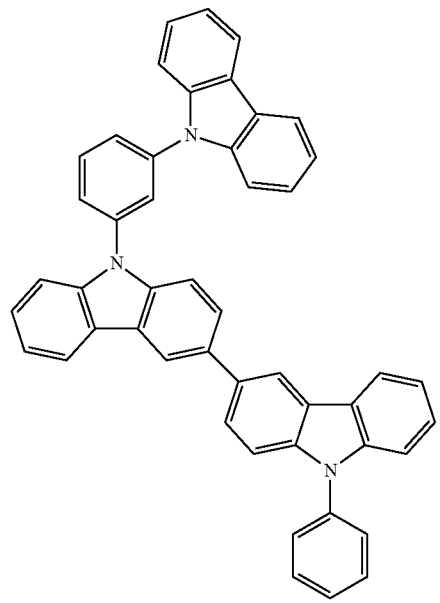
GHA-39
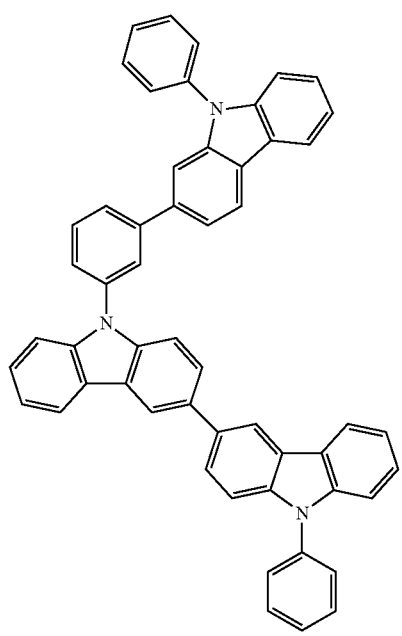
GHA-41
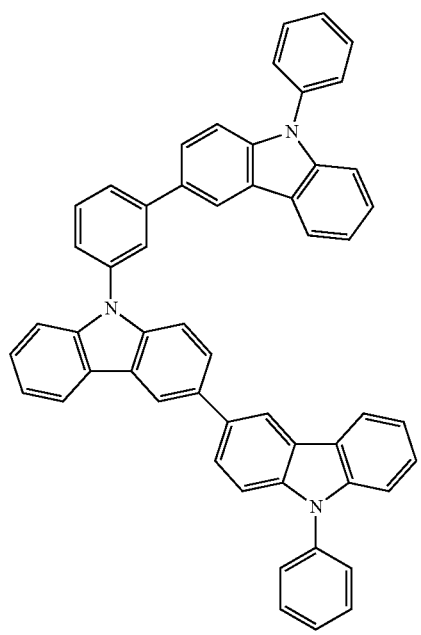

GHA-42

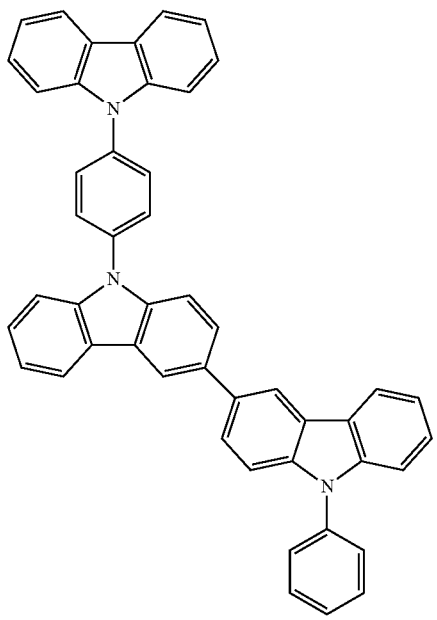

GHA-43

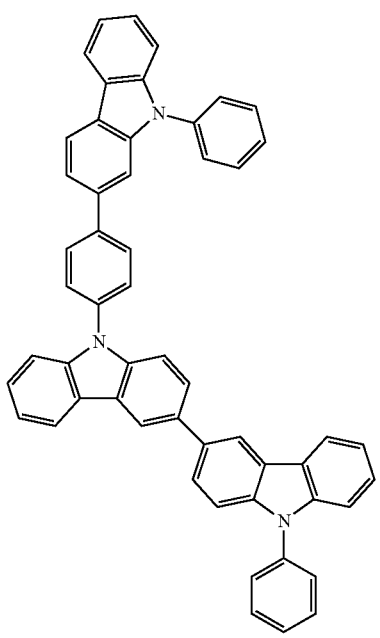

GHA-44

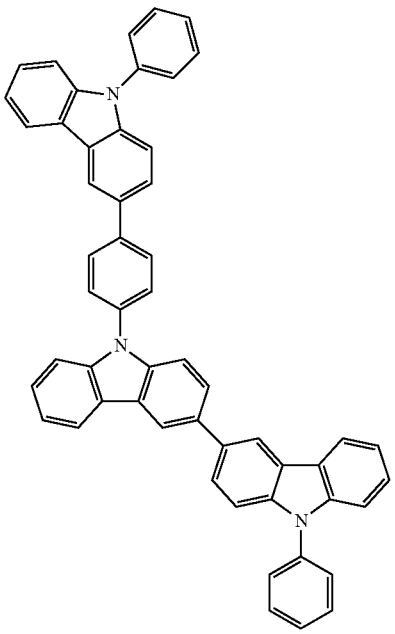

<Chemical Formula 3>

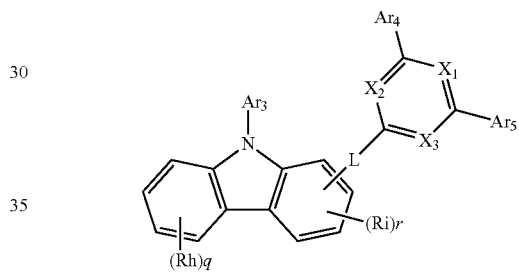

In the Chemical Formula 3, each of Rh and Ri independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C15 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 3, q denotes an integer from 1 to 4, and r denotes an integer from 1 to 3. In the Chemical Formula 3, each of $Ar_3$, $Ar_4$ and $Ar_5$ independently represents one selected from the group consisting of a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted dibenzofuranyl group, and a substituted or unsubstituted dibenzothiophenyl group.

In the Chemical Formula 3, L represents one selected from the group consisting of a single bond, a phenyl group, a naphthyl group, and a pyridyl group.

In the Chemical Formula 3, each of $X_1$, $X_2$, and $X_3$ independently represents N or CH, and at least two of $X_1$, $X_2$, and $X_3$ represent N. For example, examples of the second green host compound include following GHB-1 to GHB-20. The second green host compound may include at least one of the following GHB-1 through GHB-20.
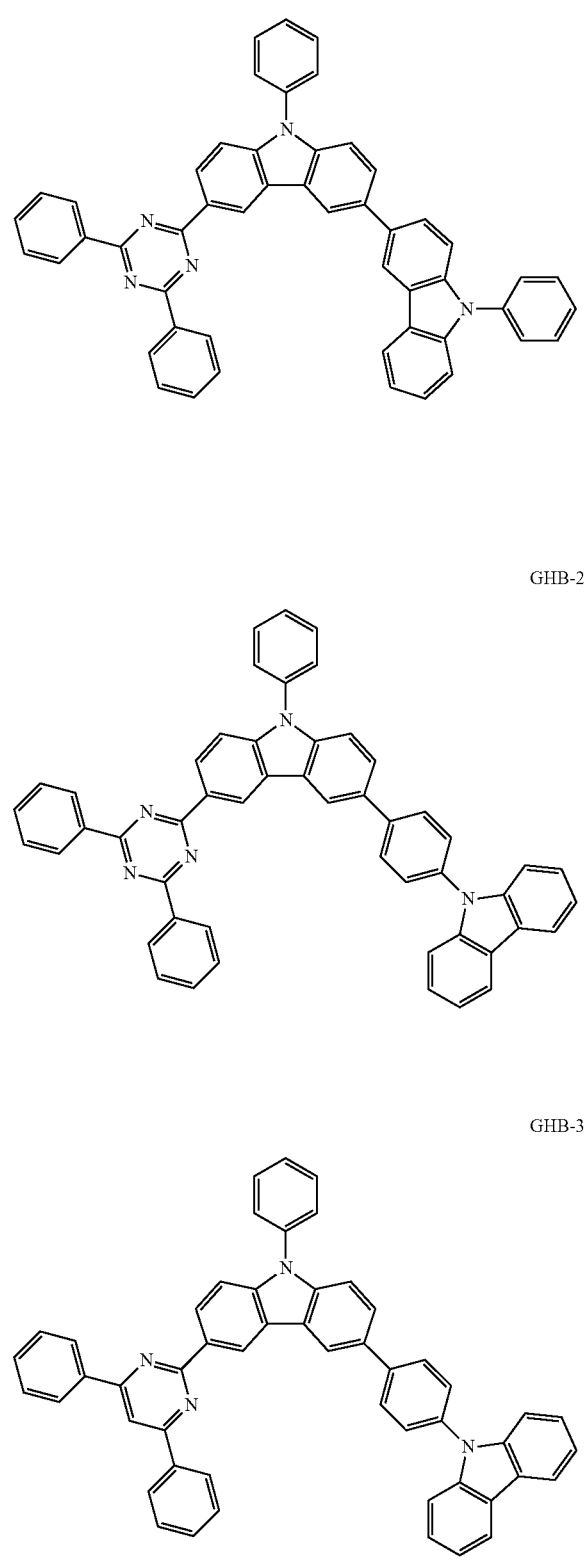
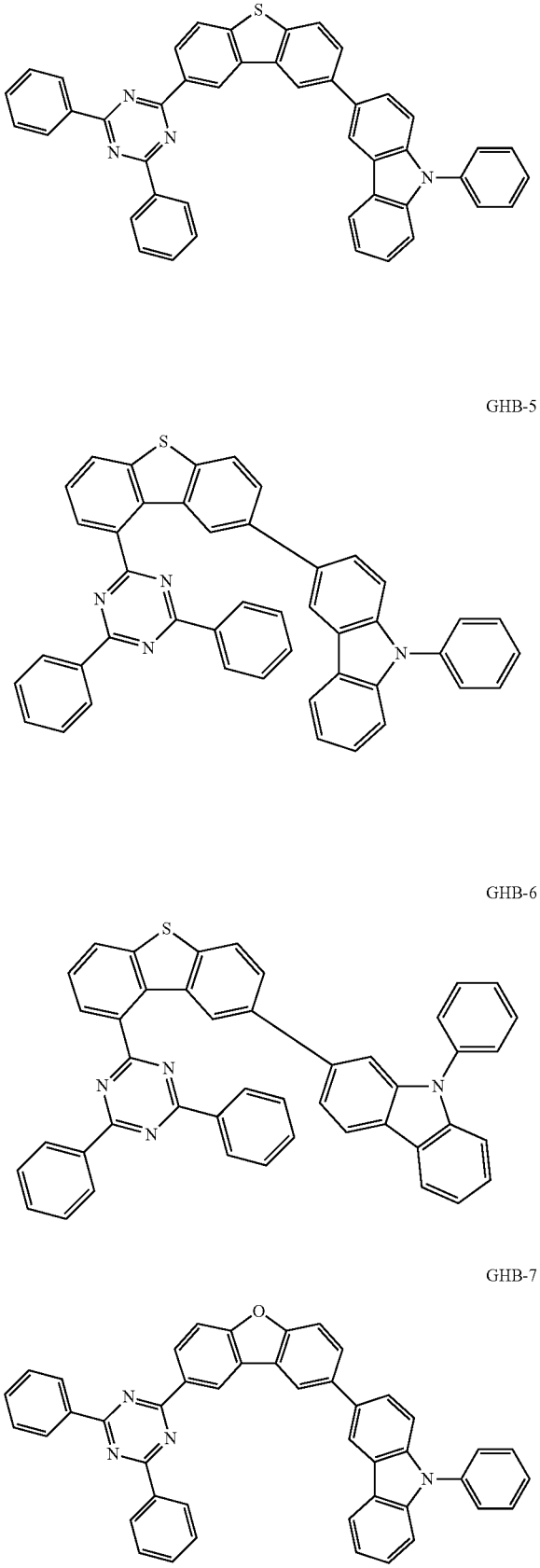

GHB-8
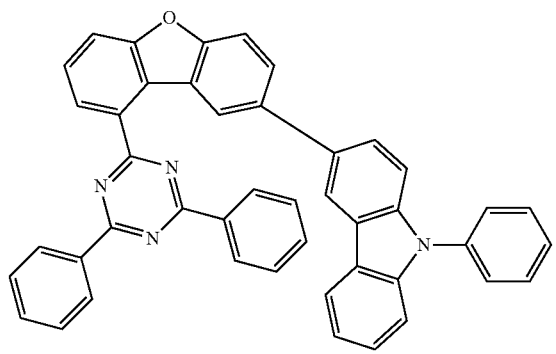
GHB-9
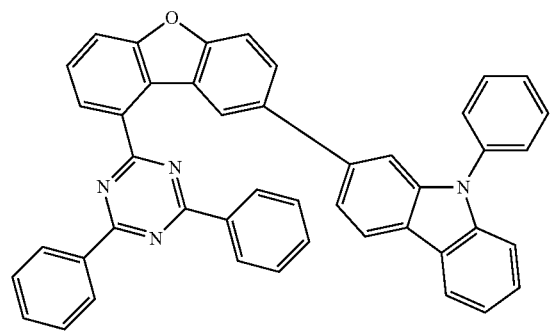
GHB-10
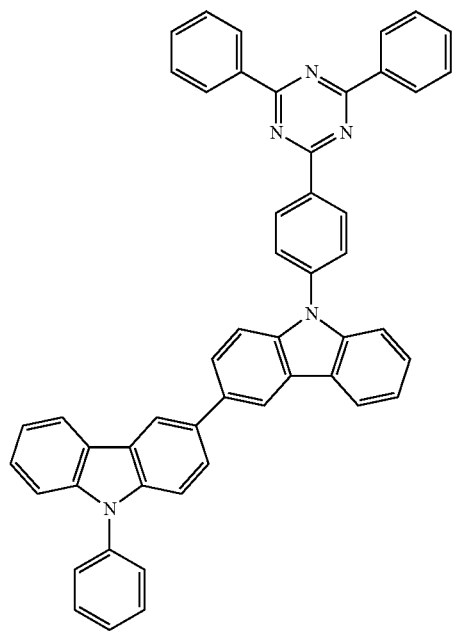
GHB-11
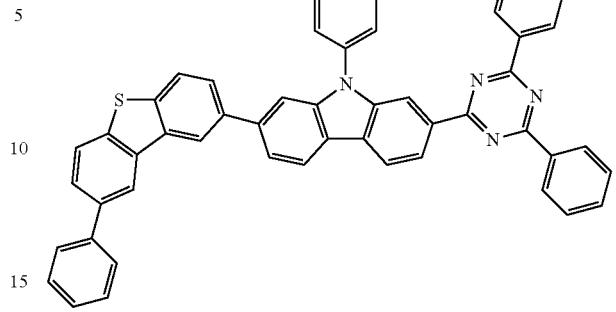
GHB-12
GHB-13
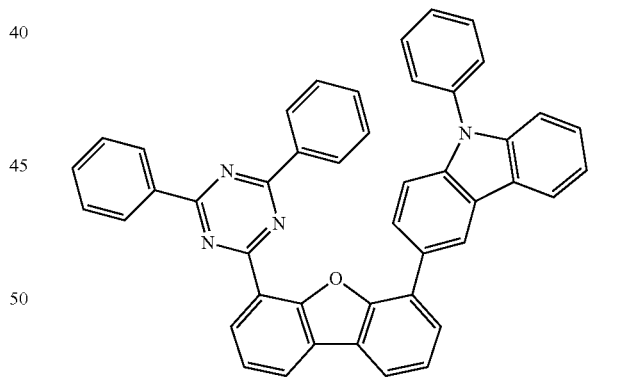
GHB-14
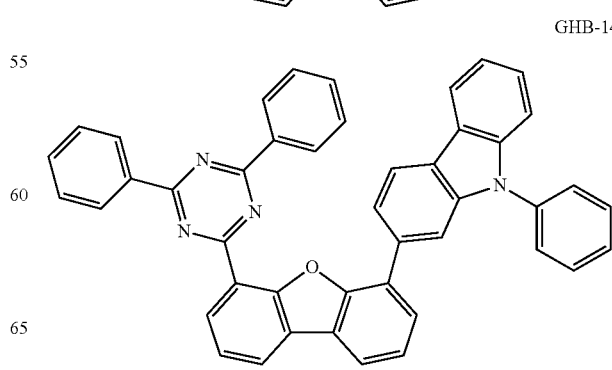

GHB-15

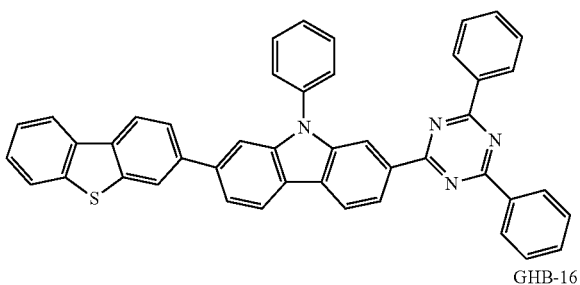

GHB-16

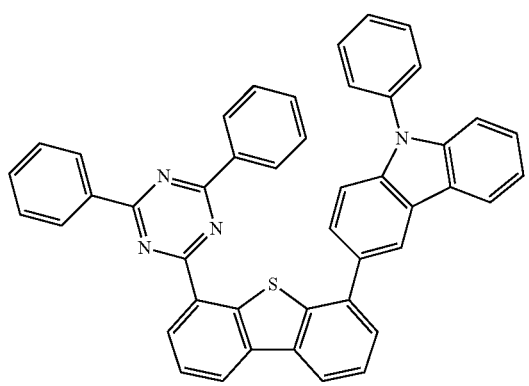

GHB-17

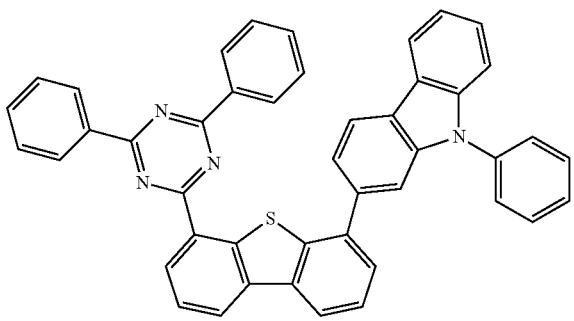

GHB-18

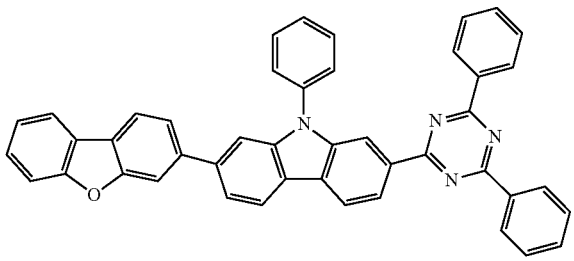

The present inventors have confirmed that when the red light-emission layer 23R does not contain the red host compound (see Comparative Example 1), when the green light-emission layer 23G does not contain the first green host compound (see Comparative Example 2), or when the green light-emission layer 23G does not contain the second green host compound (see Comparative Example 3), the charge balance inside the red/green light concurrent-emission sub-stack 23 is not achieved. As a result, the organic electroluminescence devices according to Comparative Examples could not obtain the desired color coordinate. As a result, the present inventors could not obtain a white-light organic electroluminescence device with high color purity and high color reproducibility using the Comparative Examples.

However, in accordance with one implementation of the present disclosure as described above, the red/green light concurrent-emission sub-stack 23 includes a stack of the red light-emitting layer 23R and the green light-emitting layer 23G in direct contact with each other. The red/green light concurrent-emission sub-stack 23 has a light-emitting region distributed near an interface between the red light-emitting layer 23R and the green light-emitting layer 23G. In this connection, the green light-emitting layer 23G is closer to the cathode C than the red light-emitting layer 23R is. In other words, the green light-emitting layer 23G is disposed between the red light-emitting layer 23R and the cathode C.

Thus, positioning the green light-emitting layer 23G to be closer to the cathode C than the red light-emitting layer 23R allows the hole mobility of the red host compound and the electron mobility of the green host compound to be balanced so that the emission region can be distributed near the interface between the red light-emitting layer 23R and the green light-emitting layer 23G. As a result, the organic electroluminescence device 200 can obtain the desired color coordinate required for the rendering of the white light.

In contrast, when the green light-emitting layer 23G is closer to the anode A than the red light-emitting layer 23R is, in other words, when the green light-emitting layer 23G is disposed between the red light-emitting layer 23R and the anode A, the mobility of the hole and the mobility of the mobility of the electron injected into the red/green light concurrent-emission sub-stack 23 from the anode A and the cathode C becomes unbalanced, such that a luminance level of the red light emission region may be different from a luminance level of the green light emission region. As a result, it is difficult to obtain the appropriate color coordinate required for white light emission from the red/green light concurrent-emission sub-stack 23. In other words, when the green light-emitting layer 23G is disposed between the red light-emitting layer 23R and the anode A, a color of a longer or shorter wavelength than a wavelength of a desired color is emitted, and thus the desired color is not obtained.

In addition, the red phosphorescent dopant may include at least one of a compound represented by a following Chemical Formula 4 and a compound represented by a following Chemical Formula 5.

<Chemical Formula 4>

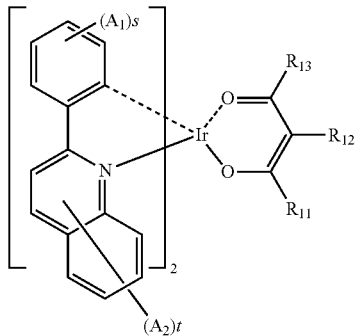

In the Chemical Formula 4, each of $A_1$ and $A_2$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 4, s denotes an integer of 1 to 4, and t denotes an integer from 1 to 6. Further, the Chemical Formula 4, each of $R_{11}$, $R_{12}$, and $R_{13}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{11}$ and $R_{12}$ may be or $R_{12}$ and $R_{13}$ may be connected to each other to form a ring.

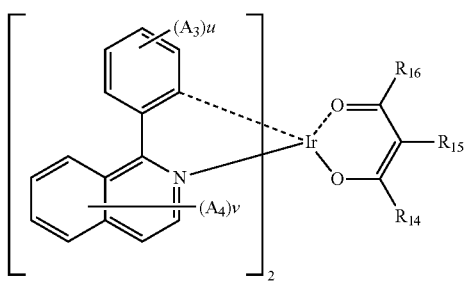

<Chemical Formula 5>

In the Chemical Formula 5, each of $A_3$ and $A_4$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 5, u denotes an integer of 1 to 4, and v denotes an integer from 1 to 6. In addition, in the Chemical Formula 5, each of $R_{14}$, $R_{15}$, and $R_{16}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{14}$ and $R_{15}$ may be or $R_{15}$ and $R_{16}$ may be connected to each other to form a ring.

The green phosphorescent dopant may include at least one of a compound represent by a following Chemical Formula 6 and a compound represent by a following Chemical Formula 7.

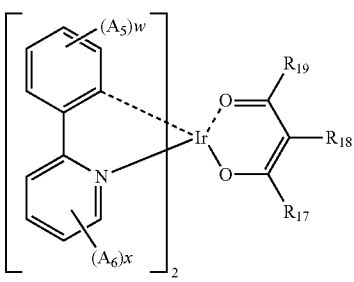

<Chemical Formula 6>

In the Chemical Formula 6, each of $A_5$ and $A_6$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 6, each of w and x independently denotes an integer of 1 to 4. Further, in the Chemical Formula 6, each of $R_{17}$, $R_{18}$, and $R_{19}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{17}$ and $R_{18}$ may be or $R_{18}$ and $R_{19}$ may be connected to each other to form a ring.

<Chemical Formula 7>

In the Chemical Formula 7, each of $A_7$ and $A_8$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group.

In the Chemical Formula 7, y denotes an integer of 1 to 4, z denotes an integer from 1 to 3, and each of $R_{20}$, $R_{21}$, and $R_{22}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{20}$ and $R_{21}$ may be or $R_{21}$ and $R_{22}$ may be connected to each other to form a ring.

In the Chemical Formula 7, each of $Y_1$, $Y_2$, $Y_3$, and $Y_4$ independently represents N or CR'. R' represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, and a substituted or unsubstituted C5 to C9 heteroaryl group.

A maximum emission wavelength band of the red phosphorescent dopant may be in a range of 610 nm to 640 nm. For example, the maximum emission wavelength band of the red phosphorescent dopant may be in a range of 620 nm to 630 nm.

A maximum emission wavelength band of the green phosphorescent dopant may be in a range of 510 nm to 540 nm. For example, the maximum emission wavelength band of the green phosphorescent dopant may be in a range of 525 nm to 535 nm.

The organic electroluminescence device 200 may satisfy at least one of following conditions (i), (ii), and (iii) for improving color purity, color reproducibility, driving characteristics, and driving efficiency.

(i) A mixing ratio of the first green host compound and the second green host compound may be in a range of from 3:7 to 7:3. For example, the mixing ratio of the first green host compound and the second green host compound may be 5:5.

(ii) An ionization potential value of the red host compound may be in a range of −5.1 eV to −5.7 eV. The ionization potential value of the first green host compound may be in a range of −5.1 eV to −5.7 eV. An electron affinity value of the second green host compound may be in a range of −2.5 eV to −3.1 eV.

(iii) A thickness of the red light-emitting layer 23R may be in a range between 5 nm and 30 nm, and a thickness of the green light-emitting layer 23G may be in a range between 5 nm and 40 nm. For example, the thickness of the red light-emitting layer 23R may be in a range between 10 nm and 20 nm, and the thickness of the green light-emitting layer 23G may be in a range between 20 nm and 40 nm. In one example, the thickness of the green light-emitting layer 23G may be larger than the thickness of the red light-emitting layer 23R.

In relation to the (i), the green light-emitting layer 23G contains a mixture between the first green host compound and the second green host compound. A content ratio of the first green host compound and the second green host compound is an important factor in determining the color coordinate of the red/green light concurrent-emission sub-stack 23.

As described above, the color coordinate of the red/green light concurrent-emission sub-stack 23 is determined to achieve the balance of holes and electrons. The first green host compound acts as a hole transportable host compound, while the second green host compound acts as an electron transportable host compound. As the content of the hole transportable host compound is higher than the content of the electron transportable host compound, an exciton-forming region occurs at a position closer to the green light-emitting layer 23G than to the red light-emitting layer 23R around the interface between the red light-emitting layer 23R and the green light-emitting layer 23G. Thus, the color coordinate of the red/green light concurrent-emission sub-stack 23 becomes more greenish (a x coordinate value of the color coordinate becomes smaller). To the contrary, as the content of the hole transportable host compound is lower than the content of the electron transportable host compound, an exciton-forming region occurs at a position closer to the red light-emitting layer 23R than to the green light-emitting layer 23G around the interface between the red light-emitting layer 23R and the green light-emitting layer 23G. Thus, the color coordinate of the red/green light concurrent-emission sub-stack 23 becomes more reddish (an x coordinate value of the color coordinate becomes larger).

In one example, the charge mobility characteristics of the two host materials are considered in controlling the content ratio of the first green host compound and the second green host compound. When considering a general manufacturing process by which the organic electroluminescence device is obtained using vacuum deposition of organic materials, and when one of the two host materials has significantly lower charge mobility characteristics than the other, the content of the host material having the significantly low charge mobility characteristic should be designed to be excessively high. In this case, consumption rates of the two host materials may be significantly different from each other. Thus, there occurs a problem that utilization of a deposition equipment is lowered due to a re-filling process of the exhausted host material. In this connection, the difference between the charge mobilities of the first green host compound and the second green host compound may be small. When the mixing ratio of the first green host compound and the second green host compound is in a range of from 3:7 to 7:3, the utilization of the deposition equipment may not be lowered.

For the charge balance and color balance within the red/green light concurrent-emission sub-stack 23, the mixing ratio of the first green host compound and the second green host compound may be in a range from 3:7 to 7:3. Preferably, the content ratio of the first green host compound and the second green host compound may be 5:5.

In relation to the (ii), amount and mobility of charges (holes and electrons) injected into the light-emission layer are determined by an energy barrier occurring at an interface between adjacent organic thin films.

The energy barrier may occur at an interface between the hole transport layer and the red host compound, an interface between the red host compound and the first green host compound, an interface between the first green host compound and the second green host compound, and an interface between the second green host compound and the electron transport layer.

In this connection, for example, each of a difference between the ionization potential values of the hole transport layer and the red host compound, a difference between the ionization potential values of the red host compound and the first green host compound, and a difference between the electron affinity values of the second green host compound and the electron transport layer may act as the energy barrier.

In accordance with the present disclosure, the energy barrier may be controlled to a value within 0.3 eV to suppress decreases of the amount and mobility of the charges (holes and electrons) injected into the light-emission layer. Thus, the organic electroluminescence device 200 can be driven without a large increase in the driving voltage.

To control the energy barrier to be a value within 0.3 eV, for example, when the ionization potential of the hole transport layer 22 is around −5.4 eV, each of the ionization potentials of the red host compound and the first green host compound is in a range of −5.1 eV to −5.7 eV. Further, in order to control the energy barrier to be a value within 0.3 eV, for example, when the electron transport layer 24 has an electron affinity of about −2.8 eV, the electron affinity value of the second green host compound may be in a range of −2.5 eV to −3.1 eV.

With respect to the (iii), the charge mobility of each host material is dependent on the thickness of the thin film made of the host material. As the thickness of the red light-emitting layer 23R increases, the charge mobility in the red light-emitting layer 23R may decrease. As the thickness of the green light-emission layer 23G increases, the charge mobility in the green light-emission layer 23G may decrease.

When considering the charge mobility characteristics of the red host compound, the thickness of the red light-emitting layer 23R may be in a range between 5 nm and 30 nm in order to balance the charge mobility in the red/green light concurrent-emission sub-stack 23. Preferably, the thickness of the red light-emitting layer 23R may be in a range from 10 nm to 20 nm. When the thickness of the red light-emitting layer 23R is outside of the above defined range, the light emitting efficiency of the organic electroluminescence device 200 may be lowered, and a desired color coordinate of color emitted from the organic electroluminescence device 200 may not be achieved.

Specifically, when the thickness of the red light-emitting layer 23R is smaller than 5 nm, a tunneling effect may cause the charge to pass through the red light-emission layer 23R. In this case, the emission efficiency of the organic electroluminescence device 200 may be lowered. When the thickness of the red light-emitting layer 23R exceeds 30 nm, it may be difficult to obtain the color coordinate of the desired white light because the wavelength of the emitted light is biased to the red color. In order to obtain the luminous efficiency of the organic electroluminescence device 200 and the color coordinate of the desired white light emitted therefrom, preferably, the thickness of the red light-emitting layer 23R may be in a range between 10 nm and 20 nm.

When considering the charge mobility characteristics of the first green host compound and the second green host compound, the thickness of the green light-emitting layer 23G may be in a range between 5 nm and 40 nm in order to balance the charge mobility in the red/green light concurrent-emission sub-stack 23. Preferably, the thickness of the green light-emitting layer 23G may be in a range from 20 nm to 40 nm. When the thickness of the green light-emission layer 23G is outside of the above defined range, the light emitting efficiency of the organic electroluminescence device 200 may be lowered and a desired color coordinate may not be achieved.

Specifically, when the thickness of the green light-emitting layer 23G is smaller than 5 nm, the tunneling effect may cause the charge to pass through the green light-emission layer 23G. In this case, the emission efficiency of the organic electroluminescence device 200 may be lowered. When the thickness of the green light-emitting layer 23G exceeds 40 nm, it may be difficult to obtain the color coordinate of the desired white light since the wavelength of the light as emitted is biased to the green color. In order to obtain the luminous efficiency of the organic electroluminescence device 200 and the color coordinate of the desired white light emitted therefrom, the thickness of the green light-emitting layer 23G may be in a range between 20 nm and 40 nm.

The thicknesses of the red light-emitting layer 23R and the green light-emitting layer 23G may be controlled to be within the above defined ranges, thereby to achieve the charge balance or color balance within the red/green light concurrent-emission sub-stack 23.

Figure 3:
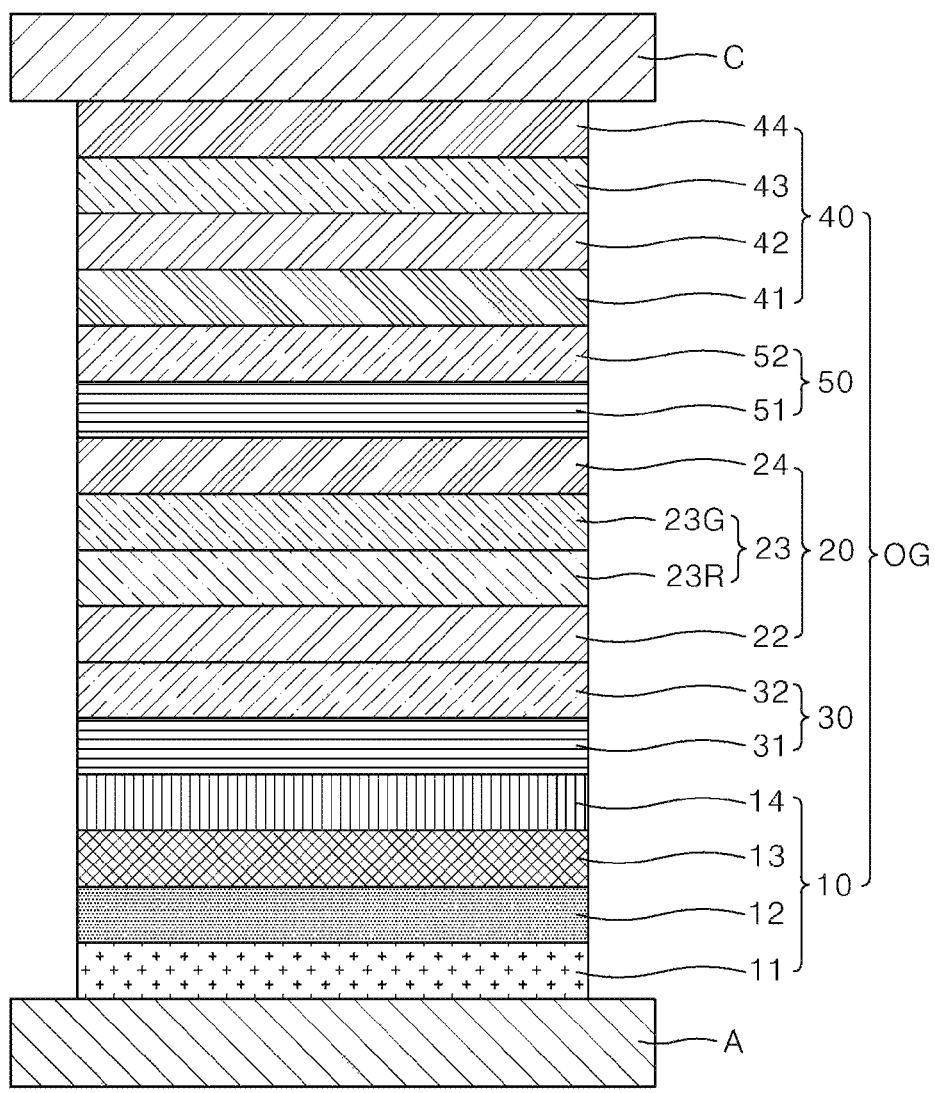
FIG. 3 is a schematic diagram of an embodiment of an organic electroluminescence device having multilayer light emitting structures.

Next, FIG. 3 shows a schematic diagram of an organic electroluminescence device 210 having another exemplary multilayer emission structure. Referring to FIGS. 2 and 3, the organic electroluminescence device 210 differs from the organic electroluminescence device 200 in that the former further includes a third stack 40 disposed between the cathode C and second stack 20. Further, the organic electroluminescence device 210 differs from the organic electroluminescence device 200 in that the former further includes a charge generation layer 50 disposed between the second stack 20 and the third stack 40.

Referring to FIG. 3, the third stack 40 includes a hole transport layer 41, a blue light-emission layer 43, and an electron transport layer 44. The organic electroluminescence device 210 differs from the organic electroluminescence device 200 in that the red/green light concurrent-emission sub-stack 23 is disposed between the blue light-emitting layers 13 and 43 in the organic electroluminescence device 210.

In addition, the third stack 40 may further include a hole injection layer 41 disposed between the charge generation layer 50 and the hole transport layer 42. Further, the third stack 40 may further include a first functional layer having both of a hole injection function and a hole transport function, a second functional layer having both of an electron transport function and an electron injection function, an electron blocking layer, a hole blocking layer, and an electron injection layer. In this case, the first functional layer, the buffer layer and the electron blocking layer are sequentially stacked between the hole transport layer 42 and the blue light-emitting layer 43 and in a direction from the hole transport layer 42 toward the blue light-emission layer 43. Further, the hole blocking layer is disposed between the blue light-emitting layer 43 and the electron transport layer 44. Also, the electron injection layer and the second functional layer are sequentially stacked between the electron transport layer 44 and the cathode C and in a direction from the electron transport layer 44 to the cathode C.

In addition, the charge generation layer 50 serves to regulate the charge balance between the second stack 20 and the third stack 40. Thus, the charge generation layer 50 serves to allow the light emission efficiency of the organic electroluminescence device 300 to be increased and to allow the lifetime of the device 300 to be improved. As shown, the charge generation layer 50 includes an n-type charge generation layer 51 and a p-type charge generation layer 52. The n-type charge generation layer 51 is disposed between the second stack 20 and the third stack 40, while the p-type charge generation layer 52 is disposed between the n-type charge generation layer 51 and the third stack 40.

Figure 4:
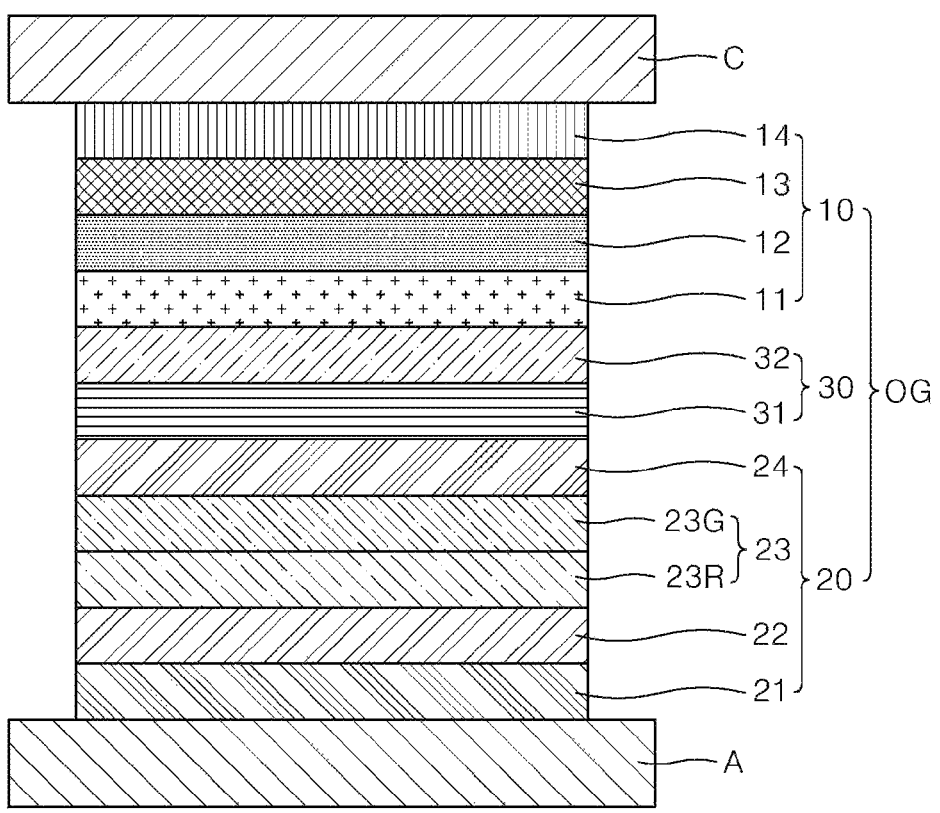
FIG. 4 is a schematic diagram of an embodiment of an organic electroluminescence device having multilayer light emitting structures.
Figure 5:
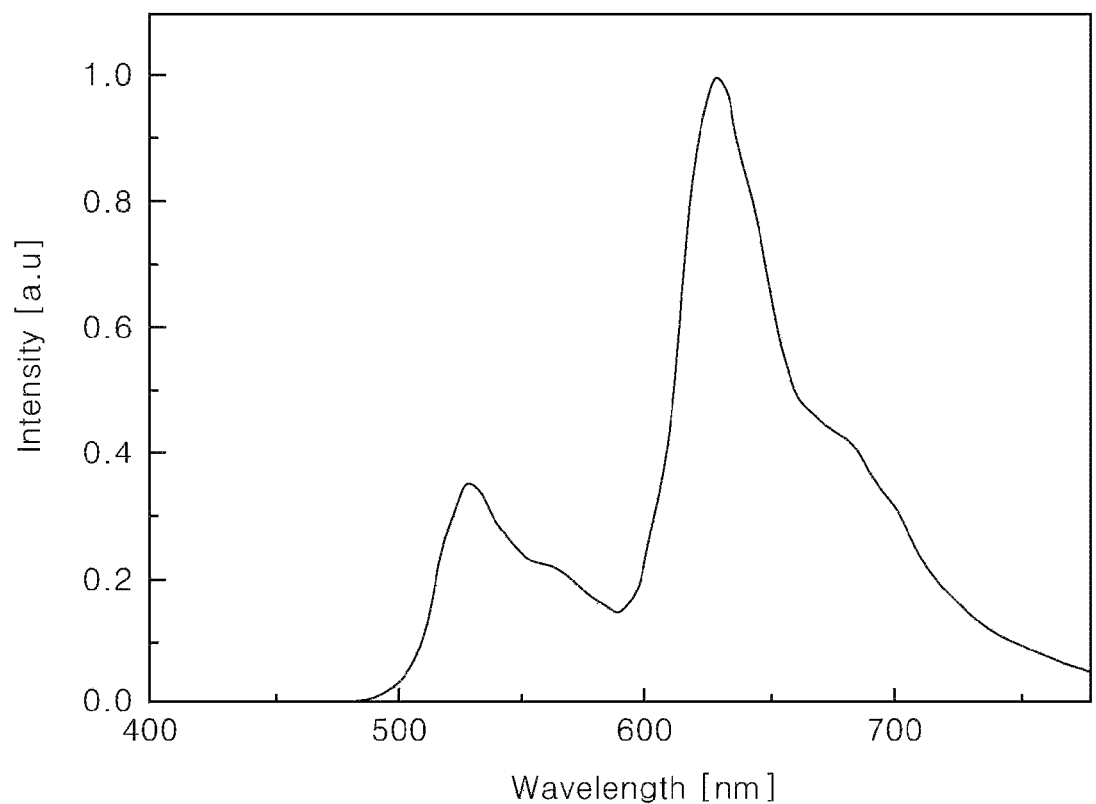
FIG. 5 is an electroluminescence spectral image of an organic electroluminescence device according to Comparative Example 1.
Figure 6:
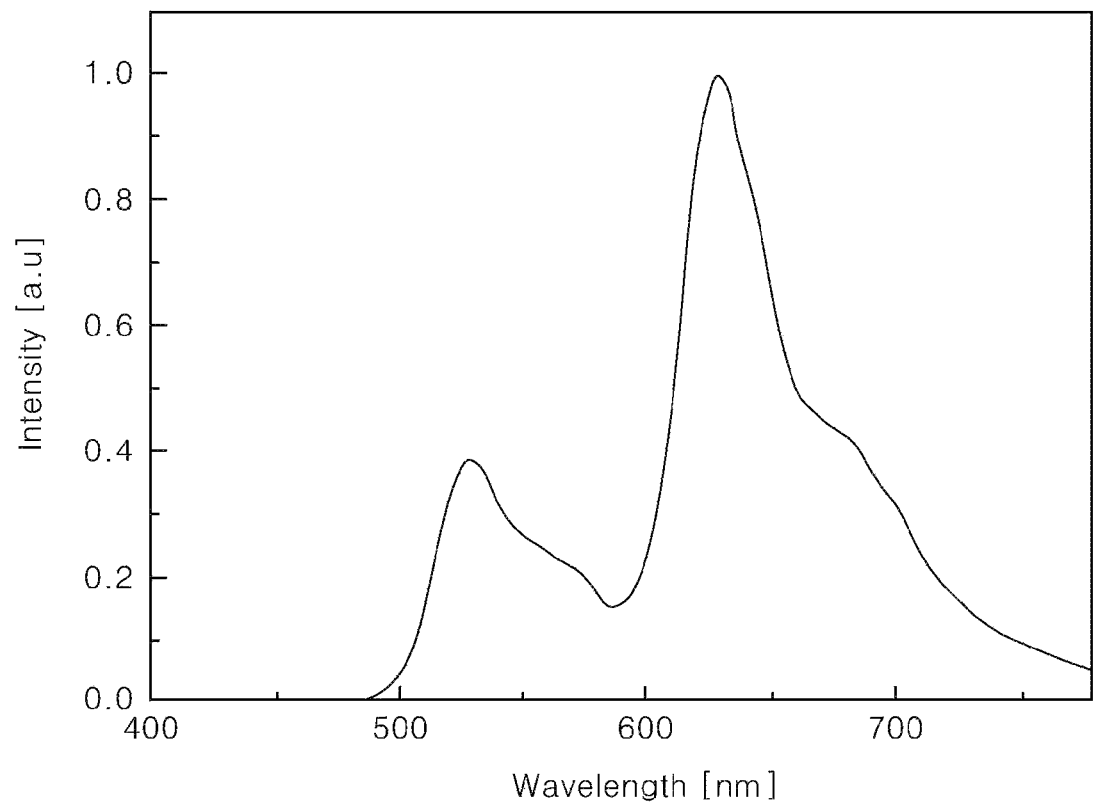
FIG. 6 is an electroluminescence spectral image of an organic electroluminescence device according to Comparative Example 2.
Figure 7:
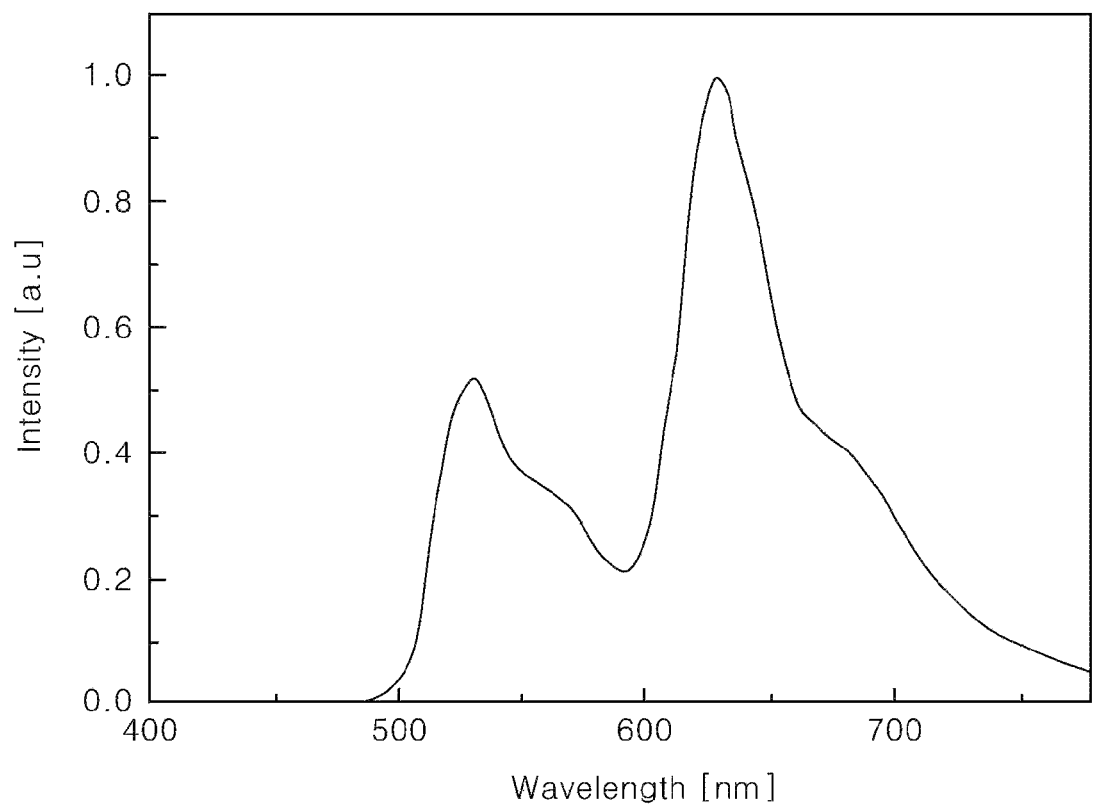
FIG. 7 is an electroluminescence spectral image of an organic electroluminescence device according to Comparative Example 3.
Figure 8:
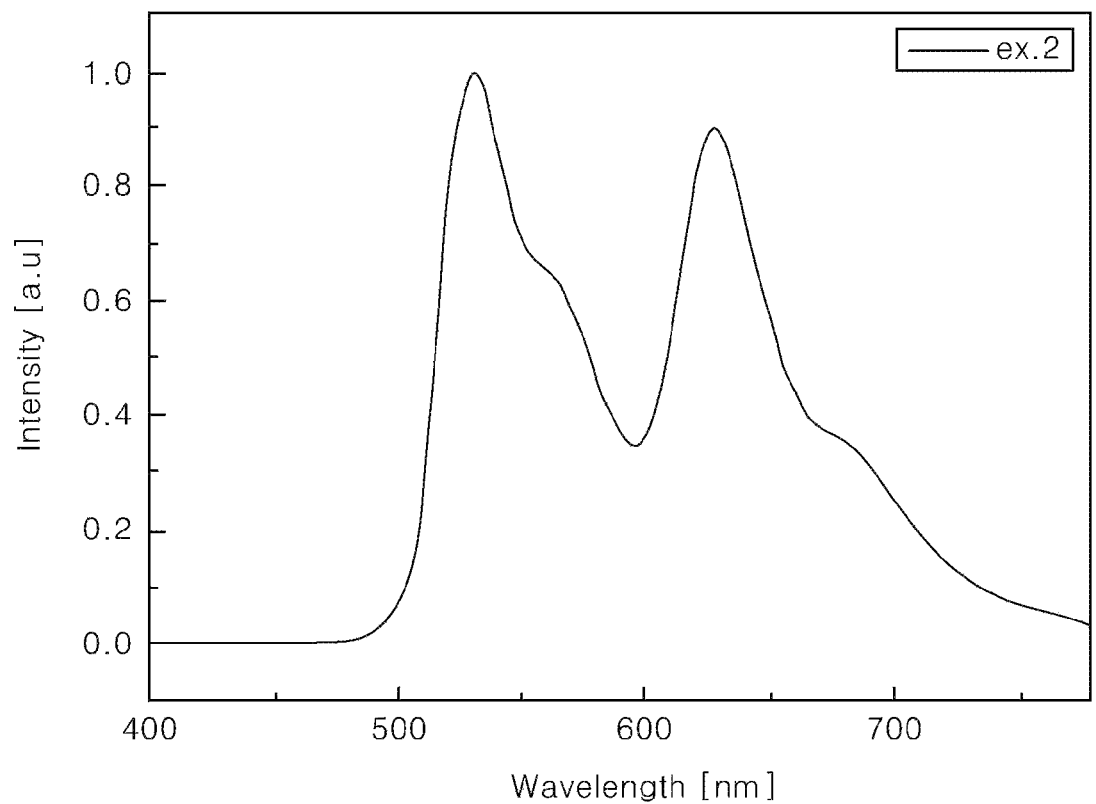
FIG. 8 is an electroluminescence spectral image of an organic electroluminescence device according to Example 1.
Figure 9:
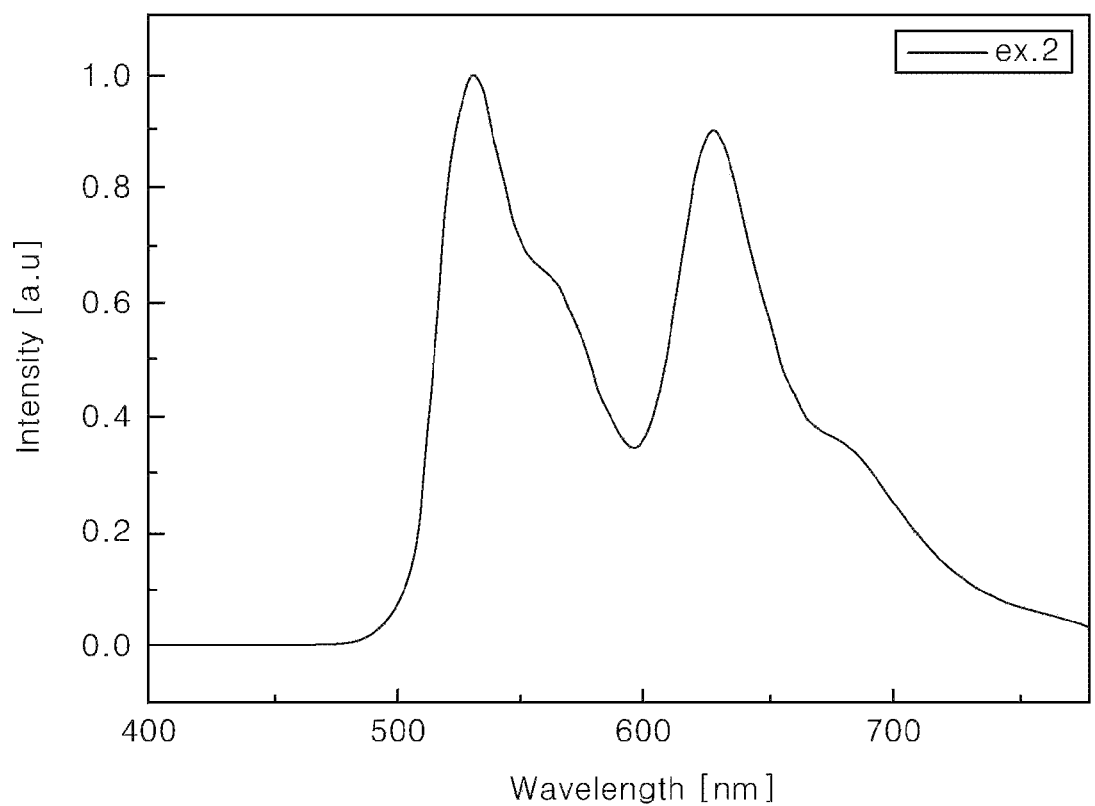
FIG. 9 is an electroluminescence spectral image of an organic electroluminescence device according to Example 2.
Figure 10:
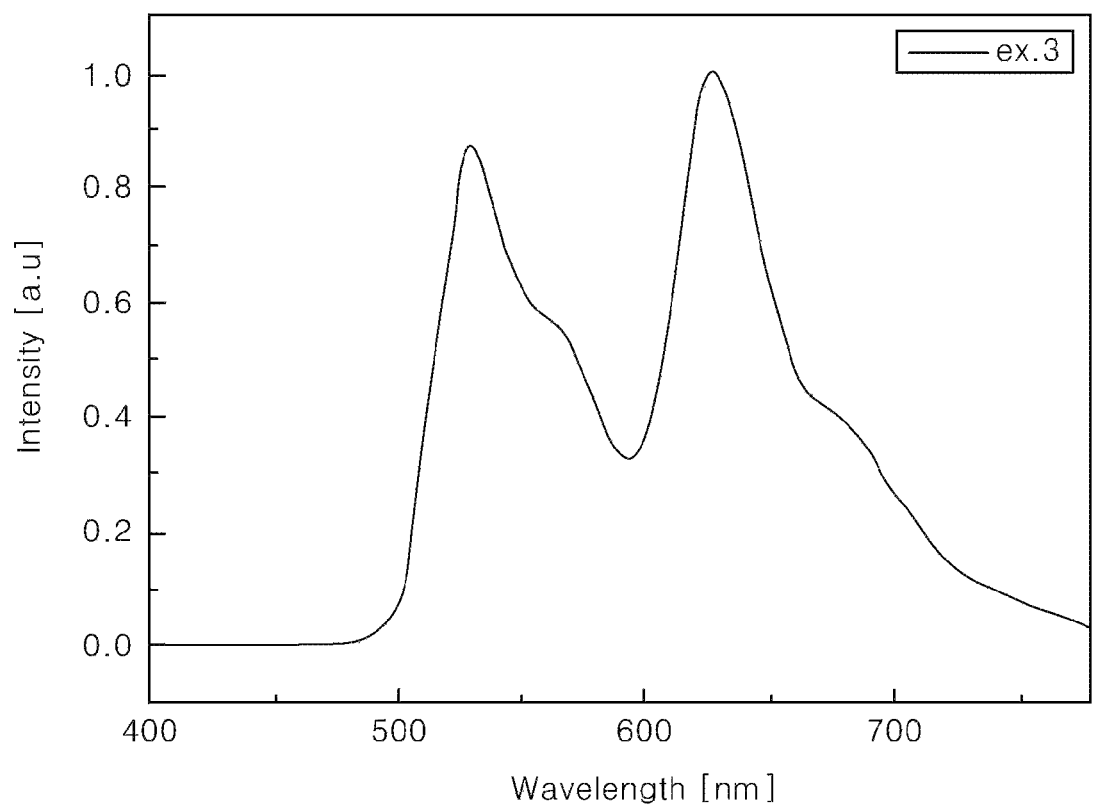
FIG. 10 is an electroluminescence spectral image of an organic electroluminescence device according to Example 3.
Figure 11:
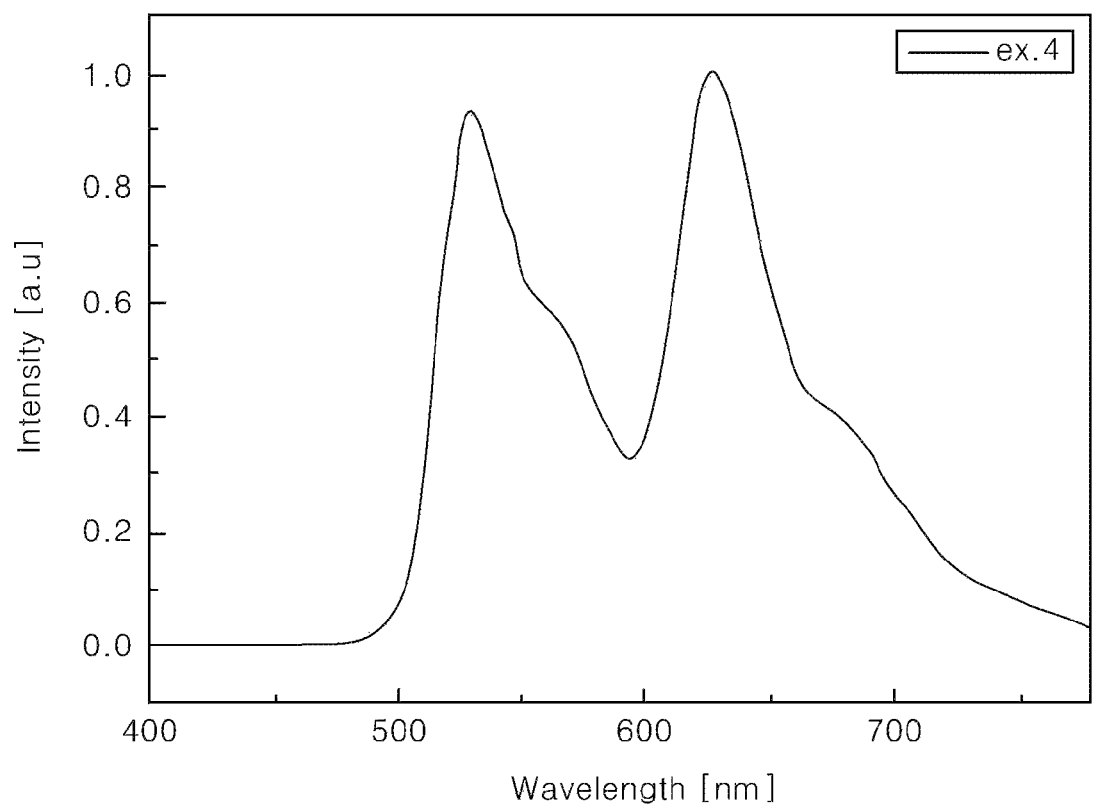
FIG. 11 is an electroluminescence spectral image of an organic electroluminescence device according to Example 4.
Figure 12:
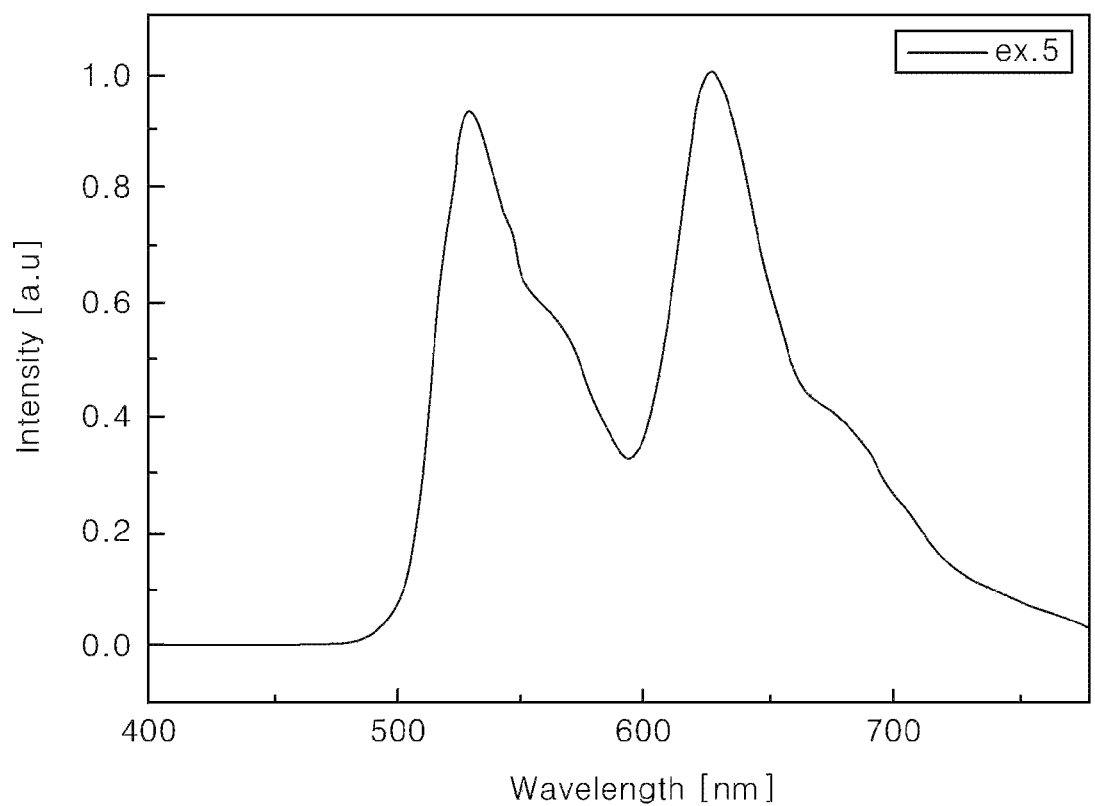
FIG. 12 is an electroluminescence spectral image of an organic electroluminescence device according to Example 5.
Figure 13:
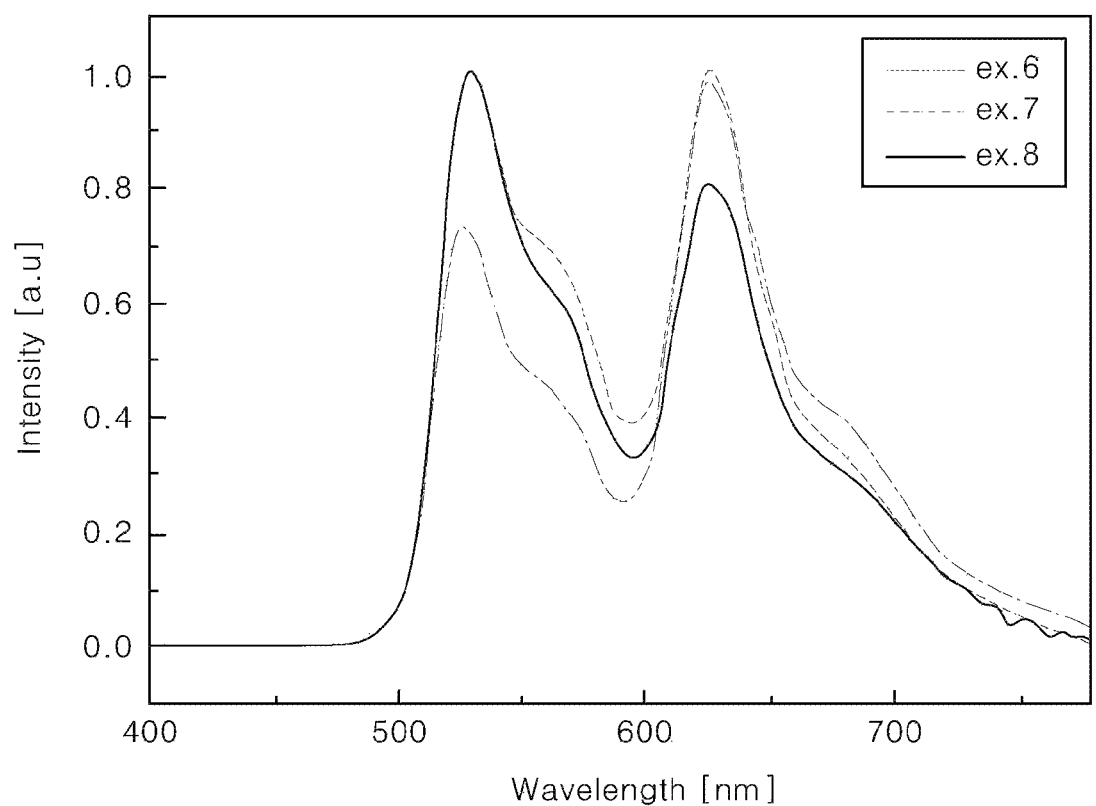
FIG. 13 is an electroluminescence spectral image of organic electroluminescence devices according to Examples 6 to 8.

Next, FIG. 4 shows a schematic diagram of an organic electroluminescence device 220 of another exemplary multilayered light emitting structure. Referring to FIGS. 2 and 4, the organic electroluminescence device 220 differs from the organic electroluminescence device 200 in that, in the former device 220, the first stack 10 is disposed between the charge generation layer 30 and cathode C, and the second stack 20 is located between charge generation layer 30 and anode A.

Referring to FIG. 4, the hole injection layer 21 of the second stack 20 is disposed between the anode A and the charge generation layer 30. the hole transport layer 22 is disposed between the hole injection layer 21 and the charge generation layer 30. The red light-emitting layer 23R is disposed between the hole transport layer 22 and the charge generation layer 30. Further, the green light-emitting layer 23G is disposed between the red light-emitting layer 23R and the charge generation layer 30. The electron transport layer 24 is disposed between the green light-emission layer 23G and the charge generation layer 30.

Further, the hole injection layer 11 of the first stack 20 is disposed between the cathode C and the charge generation layer 30. The hole transport layer 12 is disposed between the hole injection layer 11 and the cathode C. The blue light-emission layer 13 is disposed between the hole transport layer 12 and the cathode C. Further, the electron transport layer 14 is disposed between the blue light-emission layer 13 and the cathode C.

The n-type charge generation layer 31 is disposed between the electron transport layer 24 and the p-type charge generation layer 32. The p-type charge generation layer 32 is disposed between one of the hole injection layer 11 and the hole transport layer 12 and the n-type charge generation layer 31.

Electroluminescence spectra data of FIGS. 5 to 13 and color coordinate data of Table 2 were obtained using organic electroluminescence devices according to Comparative Examples and organic electroluminescence devices according to Examples.

Example 1

A hole injection layer, a hole transport layer, a light-emission layer, an electron transport layer, an electron injection layer, and a cathode were deposited onto an ITO substrate in an order of following (a) to (e), under about $5 \times 10^{-6}$ to $7 \times 10^{-6}$ torr vacuum, via evaporation from a heated boat, thereby to form an organic electroluminescence device (ITO/HIL/HTL/EML/ETL/EIL/Cathode). Then, the device was transferred from a deposition chamber to a drying box and subsequently encapsulated using UV cured epoxy and moisture getter.

The ITO substrate was washed with UV ozone before use and then loaded into an evaporation system. Thereafter, the ITO substrate was transferred into a vacuum deposition chamber in which following (a) to (e) were conducted to deposit the hole injection layer, the hole transport layer, the light-emission layer, the electron transport layer, the electron injection layer and the cathode on the ITO substrate in this order.

(a) hole injection layer (thickness 50 Å): a compound represented by Chemical Formula (I) was used as the hole injection layer material.

(b) hole transport layer (thickness 200 Å): A compound represented by a following Chemical Formula (II) was used as the hole transport layer material.

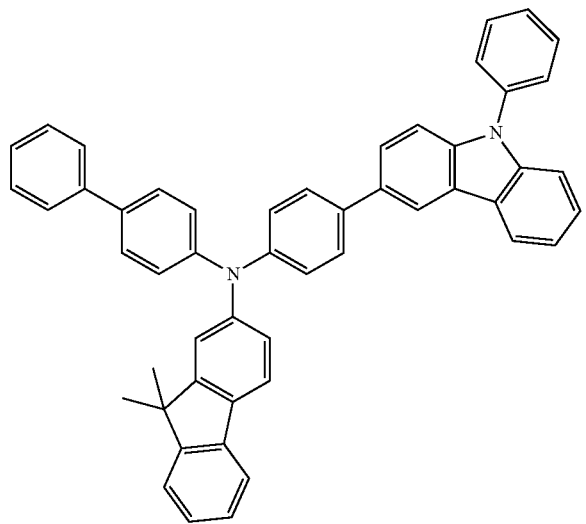

<Chemical Formula (II)>

(c) light-emission layer: a red light-emission layer (thickness 200 Å) and a green light-emission layer (thickness 300 Å) were, sequentially and in this order, deposited on the hole transport layer. In this connection, RH-4 was used as a host material of the red light-emission layer and 3% dopant was doped thereto. A mixture of GHA-2 and GHB-1 in a mixing ratio of 5:5 was used as a host material of the green light-emission layer and 15% dopant was doped thereto.

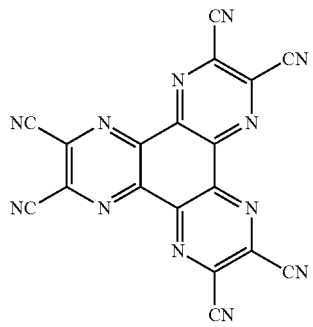

<Chemical Formula (I)>

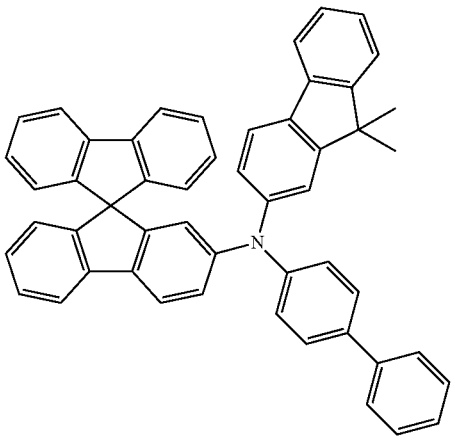

<RH-4>

<GHA-2>

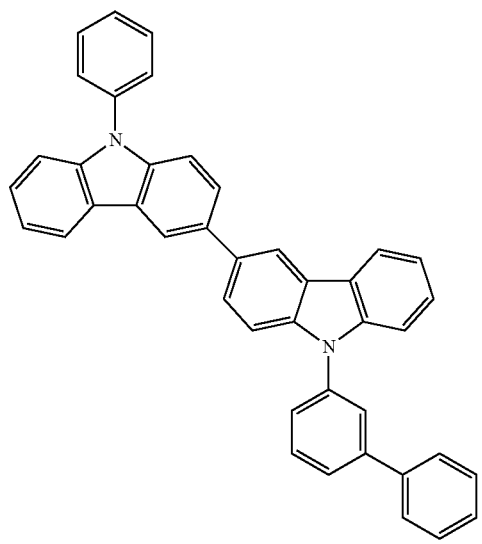

<Chemical Formula (III)>

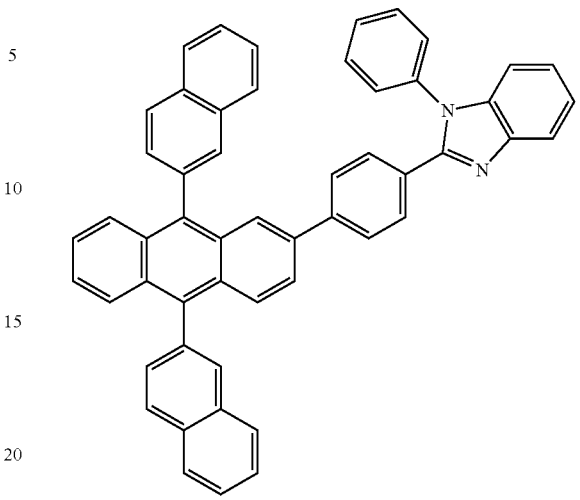

(e) electron injection layer (thickness 10 Å): the electron injection layer material employed LiF.

(f) cathode (thickness 1000 Å): the cathode employed Al.

Example 2

An organic electroluminescence device was fabricated in the same manner as in Example 1, except that RH-10 was used instead of RH-4 used in Example 1.

<GHB-1>

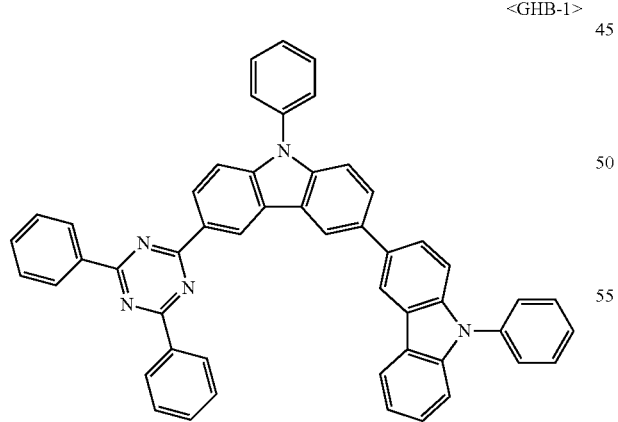

<RH-10>

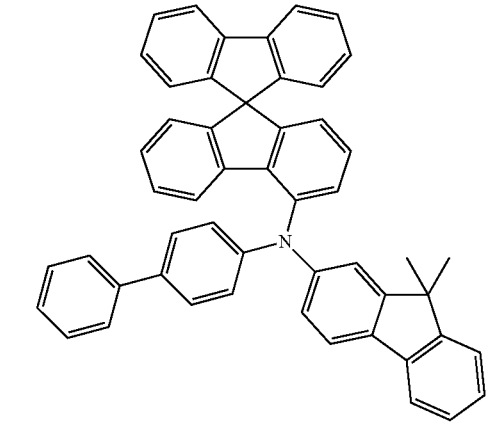

(d) electron transport layer (thickness 200 Å): a compound represented by a following Chemical Formula (III) was used as the electron transport layer material.

Example 3

An organic electroluminescence device was fabricated in the same manner as in Example 1 except that GHA-13 was used instead of GHA-2 used in Example 1.

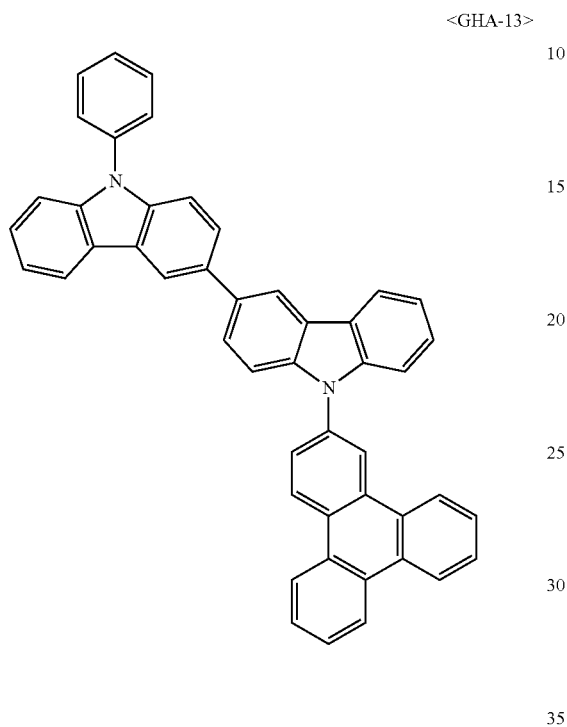

<GHA-13>

Example 4

An organic electroluminescence device was fabricated in the same manner as in Example 1, except that GHB-8 was used instead of GHB-1 used in Example 1.

Example 5

An organic electroluminescence device was fabricated in the same manner as in Example 1, except that GHA-5 and GHB-9 were respectively used instead of GHA-2 and GHB-1 used in Example 1.

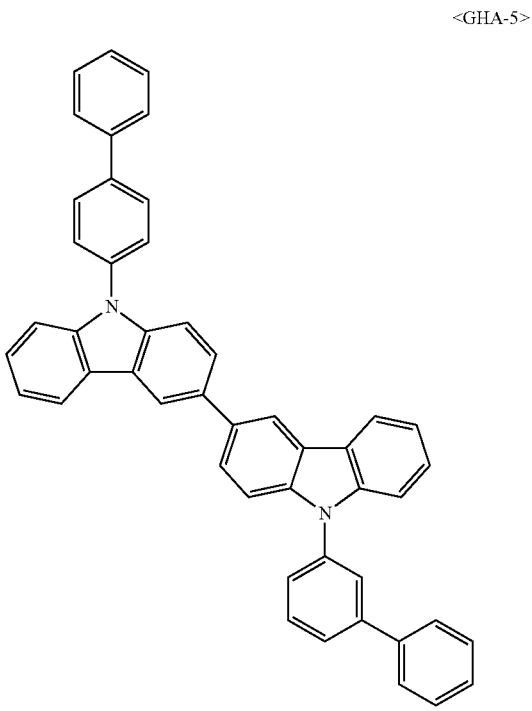

<GHA-5>

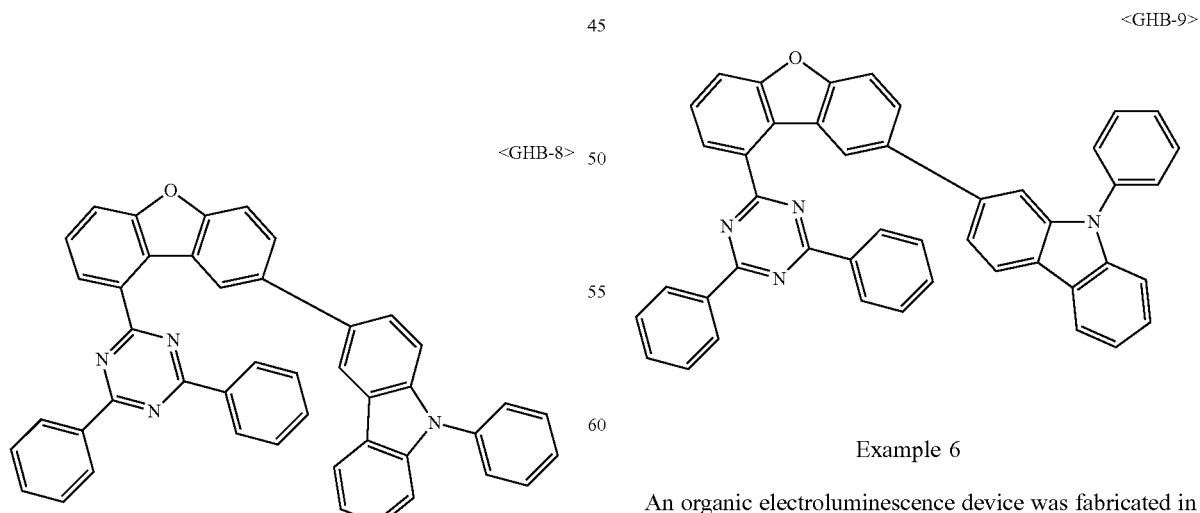

<GHB-8>

<GHB-9>

Example 6

An organic electroluminescence device was fabricated in the same manner as in Example 1 except that GHA-3 and GHB-8 were respectively used instead of GHA-2 and GHB-1 used in Example 1, and a content ratio of GHA-3 and GHB-8 was 3:7.

<GHA-3>

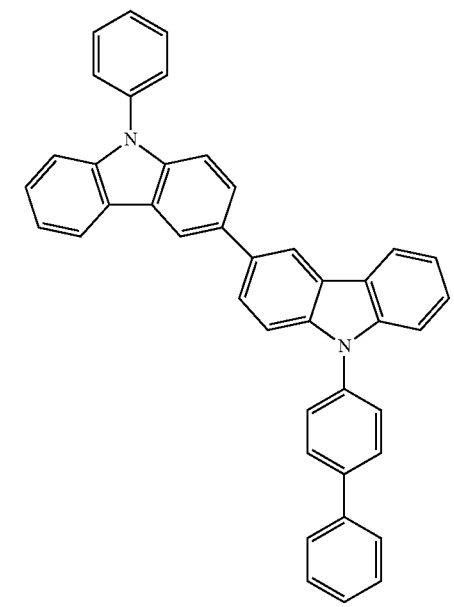

<GHB-8>

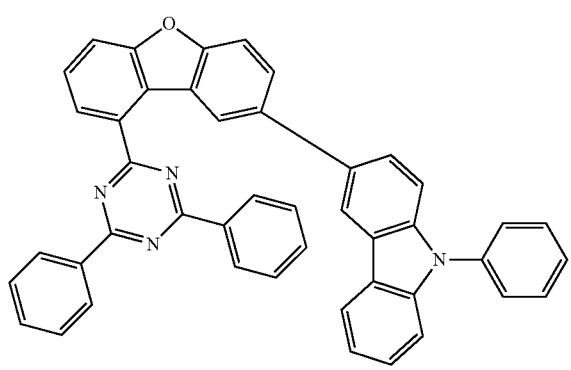

Example 7

An organic electroluminescence device was fabricated in the same manner as in Example 1 except that GHA-3 and GHB-8 were respectively used instead of GHA-2 and GHB-1 used in Example 1, and a content ratio of GHA-3 and GHB-8 was 5:5.

Example 8

An organic electroluminescence device was fabricated in the same manner as in Example 1 except that GHA-3 and GHB-8 were respectively used instead of GHA-2 and GHB-1 used in Example 1, and a content ratio of GHA-3 and GHB-8 was 7:3.

Comparative Example 1

An organic electroluminescence device was fabricated in the same manner as in Example 1, except that a following compound A was used instead of RH-4 used in Example 1.

<Compound A>

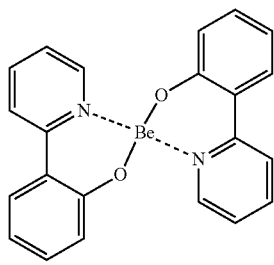

Comparative Example 2

An organic electroluminescence device was fabricated in the same manner as in Example 1, except that a following compound B was used in place of GHA-2 used in Example 1.

<Compound B>

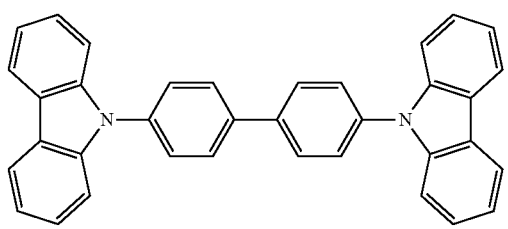

Comparative Example 3

An organic electroluminescence device was fabricated in the same manner as in Example 1 except that a following compound C was used in place of GHB-1 used in Example 1.

<Compound C>

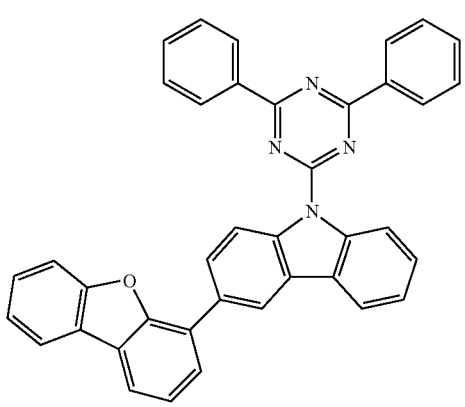

The electroluminescence spectra results of FIGS. 5 to 13 are summarized in Table 1 below.

TABLE 1

|  | Maximum peak intensity in green wavelength band (a.u.) | Maximum peak intensity in red wavelength band (a.u.) | Red/green |
| --- | --- | --- | --- |
| Example 1 | 1.00 | 0.94 | 0.94 |
| Example 2 | 1.00 | 0.9 | 0.90 |
| Example 3 | 0.86 | 1.00 | 1.16 |
| Example 4 | 0.93 | 1.00 | 1.08 |
| Example 5 | 0.95 | 1.00 | 1.05 |
| Example 6 | 0.74 | 1.00 | 1.35 |
| Example 7 | 1.00 | 0.97 | 0.97 |
| Example 8 | 1.00 | 0.81 | 0.81 |
| Comparative Example 1 | 0.35 | 1.00 | 2.86 |
| Comparative Example 2 | 0.39 | 1.00 | 2.56 |
| Comparative Example 3 | 0.53 | 1.00 | 1.89 |

Table 2 below summarizes color coordinate data obtained from the Comparative Examples and the Examples,

TABLE 2

|  | CIEx | CIEy |
| --- | --- | --- |
| Example 1 | 0.448 | 0.537 |
| Example 2 | 0.460 | 0.530 |
| Example 3 | 0.459 | 0.525 |
| Example 4 | 0.465 | 0.517 |
| Example 5 | 0.456 | 0.526 |
| Example 6 | 0.476 | 0.505 |
| Example 7 | 0.453 | 0.530 |
| Example 8 | 0.438 | 0.543 |
| Comparative Example 1 | 0.553 | 0.436 |
| Comparative Example 2 | 0.531 | 0.455 |
| Comparative Example 3 | 0.497 | 0.487 |

Referring to Table 1, the maximum peak intensities in the green wavelength band in the Examples are larger than those in the Comparative Examples. The Comparative Examples show that the maximum peak intensities in the green wavelength band are below 0.6 a.u. (arbitrary unit). Comparative Example 1 and Comparative Example 2 show that the maximum peak intensities in the green wavelength band are below approximately 0.40 a.u. Comparative Example 3 shows that the maximum peak intensity in the green wavelength band is below approximately 0.6 a.u.

In the Comparative Examples, ratios ("red/green" in Table 1) of the maximum peak intensities in the red wavelength band to the maximum peak intensities in the green wavelength band are greater than approximately 1.8.

To the contrary, referring to Table 1, each of the Examples shows that the maximum peak intensity in the green wavelength band is above 0.6 a.u. Examples 1 and 2 show that the maximum peak intensities in green wavelength bands are approximately 1.00 a.u. Example 3 shows that the maximum peak intensity in the green wavelength band is approximately 0.86 a.u.; example 4 shows that the maximum peak intensity in the green wavelength band is approximately 0.93 a.u.; example 5 shows that the maximum peak intensity in the green wavelength band is approximately 0.95 a.u.; example 6 shows that the maximum peak intensity in the green wavelength band is approximately 0.74 a.u.; and each of Examples 7 and 8 shows that each maximum peak intensity in the green wavelength band is 1.00 a.u.

In all of the Examples, the ratios ("red/green" in Table 1) of the maximum peak intensities in the red wavelength band to the maximum peak intensities in the green wavelength band were smaller than about 1.8. In detail, in Examples 1 to 5, the ratios ("red/green" in Table 1) of the maximum peak intensities in the red wavelength band to the maximum peak intensities in the green wavelength band were below approximately 1.2 or were smaller than or equal to approximately 1.16.

Referring again to FIGS. 5 to 13, the present inventors confirmed that, due to the organic combination of the red host compound and green host compound, the devices according to the Examples can emit green light of high emission intensity compared with the devices according to the Comparative Examples. This result suggests that the mobility of the holes injected into the red light-emitting layer and the mobility of electrons injected into the green light-emitting layer are in balance in the devices according to the Examples. Thus, the present inventors achieved color balance.

Further, in all of Examples 6 to 8, the ratios ("red/green" in Table 1) of the maximum peak intensities in the red wavelength band to the maximum peak intensities in the green wavelength band were approximately below 1.5 or were smaller than or equal to approximately 1.35.

Referring to Table 2, in each of the Comparative Examples, an x coordinate value in the CIE color coordinate was greater than 0.490, and a y coordinate value was smaller than 0.490. To the contrary, each of the Examples showed that the x coordinate value in the CIE color coordinate was greater than 0.430 but smaller than 0.480, and the y coordinate value was greater than 0.510 but smaller than 0.540.

Although the comparative examples did not satisfy approximately the CIE (0.45 and 0.54) as a target color coordinate, the Examples 1 to 5 show that the x-coordinate values of the CIE color coordinate were in a range of 0.45 to 0.47, and the y coordinate values of the CIE color coordinate were in a range of 0.52 to 0.54. The Examples 6 to 8 show that the x-coordinate values of the CIE color coordinate were in a range of 0.44 to 0.48, and the y coordinate values of the CIE color coordinate were in a range of 0.51 to 0.54. Thus, all of the Examples satisfied approximately the CIE (0.45 and 0.54) as a target color coordinate.

While the present disclosure has been described with reference to the accompanying drawings and the embodiments, it is to be understood that the present disclosure is not limited to the embodiments, but may be embodied in various forms. Those of ordinary skill in the art to which the present disclosure pertains may understand that the present disclosure may be embodied in other specific forms without departing from the spirit or essential characteristics of the present disclosure. It is therefore to be understood that the embodiments as described above are in all respects illustrative and not restrictive.

What is claimed is:

1. An organic electroluminescence device, comprising:
an anode;
a cathode; and
a light-emission layer disposed between the anode and the cathode,
wherein the light-emission layer includes a stack of a blue light-emission layer, and a red/green light concurrent-emission sub-stack,
wherein the red/green light concurrent-emission sub-stack includes a stack of a red light-emission layer and a green light-emission layer, wherein the green light-emission layer is disposed between the red light-emission layer and the cathode,
wherein the red light-emission layer contains a red host compound and a red phosphorescent dopant compound,
wherein the green light-emission layer contains a green host compound and a green phosphorescent dopant compound,
wherein a maximum emission wavelength band of the red phosphorescent dopant compound is in a range of 610 nm to 640 nm,
wherein a maximum emission wavelength band of the green phosphorescent dopant compound is in a range of 510 nm to 540 nm,
wherein the green host compound includes a mixture of a first green host compound and a second green host compound,
wherein a content ratio of the first green host compound to the second green host compound is 1:1,
wherein a thickness of the red light-emitting layer is in a range of 10 nm to 20 nm, wherein the green light-emitting layer has a thickness in a range of 20 nm to 40 nm,
wherein, in an electroluminescence spectrum of the device, a ratio of a maximum peak intensity in a red wavelength band to a maximum peak intensity in a green wavelength band is smaller than 1.8,
wherein the red phosphorescent dopant compound comprises at least one compound represented by Chemical Formula 4 or a compound represented by Chemical Formula 5,
wherein the green phosphorescent dopant includes at least one of a compound represented by Chemical Formula 6 or a compound represented by Chemical Formula 7:

<Chemical Formula 4>

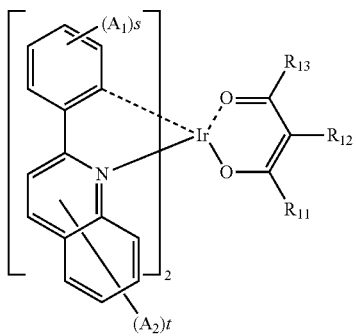

wherein, in the Chemical Formula 4, each of $A_1$ and $A_2$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group,
wherein, in the Chemical Formula 4, s denotes an integer of 1 to 4, t denotes an integer from 1 to 6, and each of $R_{11}$, $R_{12}$, and $R_{13}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{11}$ and $R_{12}$ are or $R_{12}$ and $R_{13}$ are connected to each other to form a ring, <Chemical Formula 5>

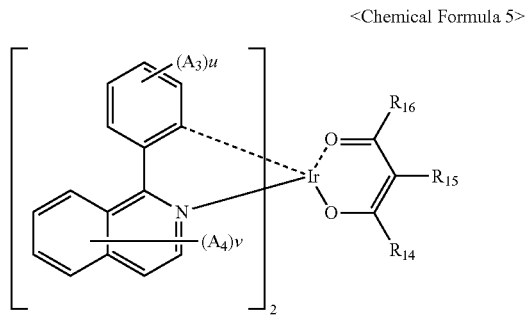

wherein, in the Chemical Formula 5, each of $A_3$ and $A_4$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group,
wherein, in the Chemical Formula 5, u denotes an integer of 1 to 4, v denotes an integer from 1 to 6, and each of $R_{14}$, $R_{15}$, and $R_{16}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{14}$ and $R_{15}$ are or $R_{15}$ and $R_{16}$ are connected to each other to form a ring, <Chemical Formula 6>

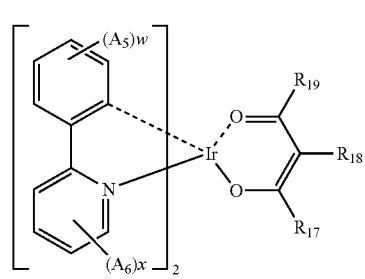

wherein, in the Chemical Formula 6, each of $A_5$ and $A_6$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 6, each of w and x independently denotes an integer of 1 to 4, and each of $R_{17}$, $R_{18}$, and $R_{19}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{17}$ and $R_{18}$ are or $R_{18}$ and $R_{19}$ are connected to each other to form a ring,

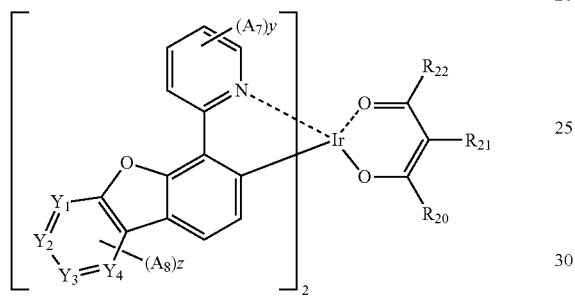

Chemical Formula 7 wherein, in the Chemical Formula 7, each of $A_7$ and $A_8$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 7, y denotes an integer of 1 to 4, z denotes an integer from 1 to 3, and each of $R_{20}$, $R_{21}$, and $R_{22}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{20}$ and $R_{21}$ are or $R_{21}$ and $R_{22}$ are connected to each other to form a ring, and wherein, in the Chemical Formula 7, each of $Y_1$, $Y_2$, $Y_3$, and $Y_4$ independently represents N or CR', wherein R' represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, and a substituted or unsubstituted C5 to C9 heteroaryl group, wherein the red light-emission layer contains a red host compound represented by at least one of the following compounds:

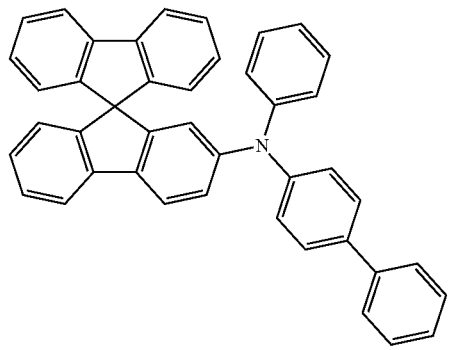

RH-1

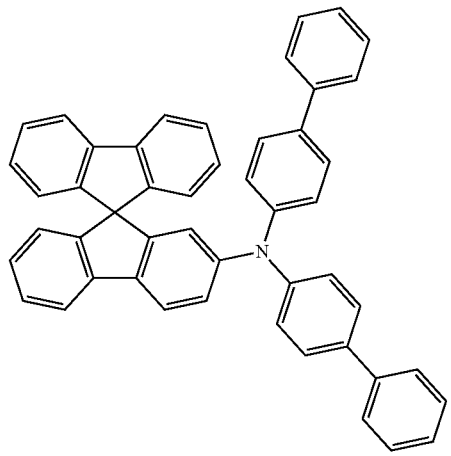

RH-2

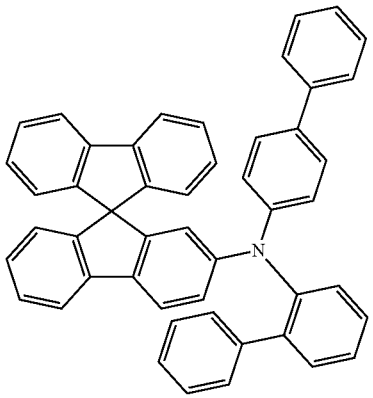

RH-3

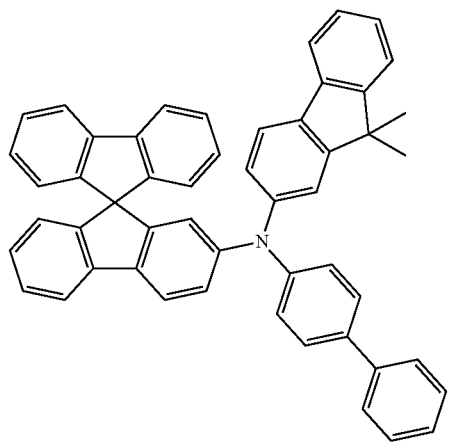

RH-4

RH-6
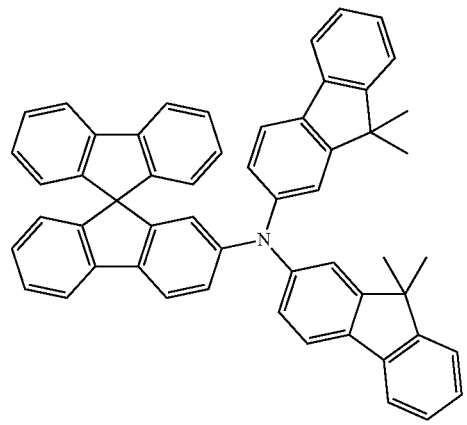
RH-9
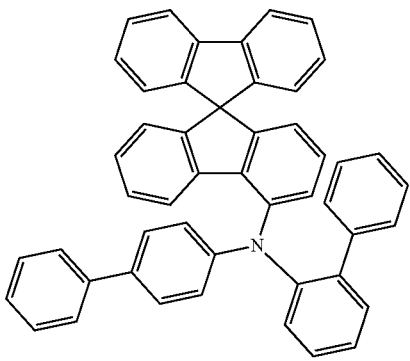
RH-7
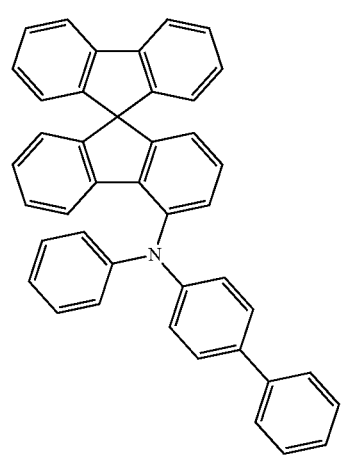
RH-10
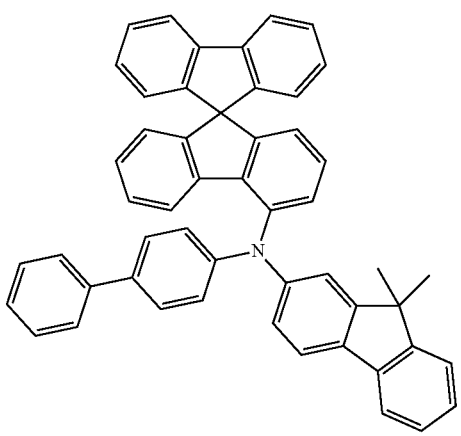
RH-8
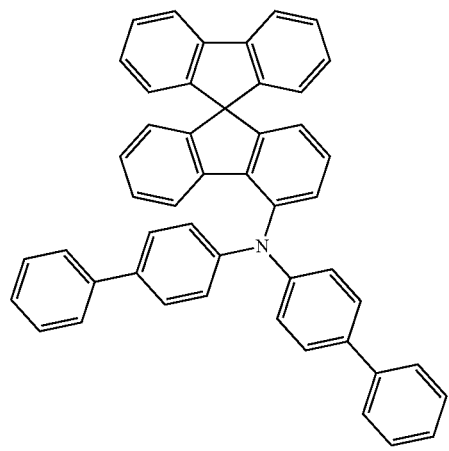
RH-11
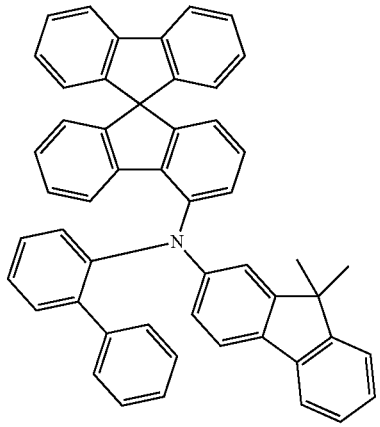

RH-12
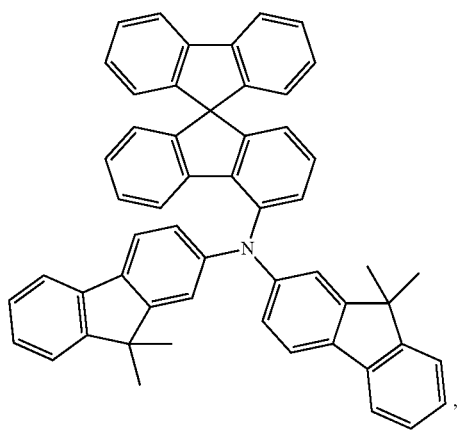
wherein the first green host compound is a compound represented by at least one of the following compounds:
GHA-1
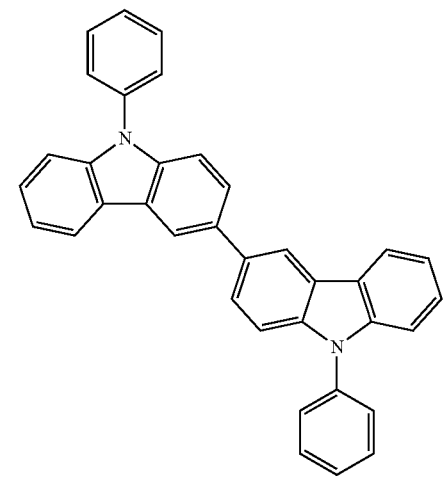
GHA-2
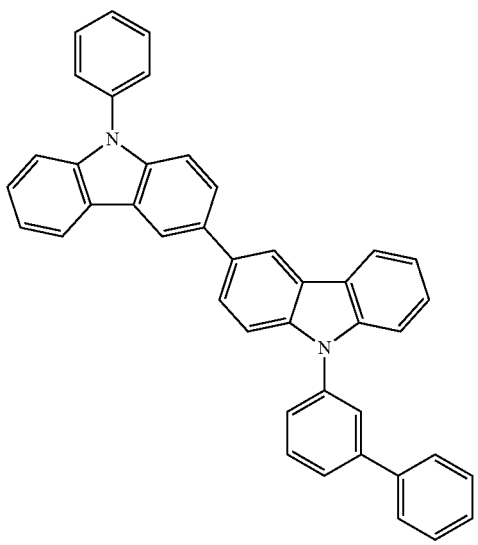
GHA-3
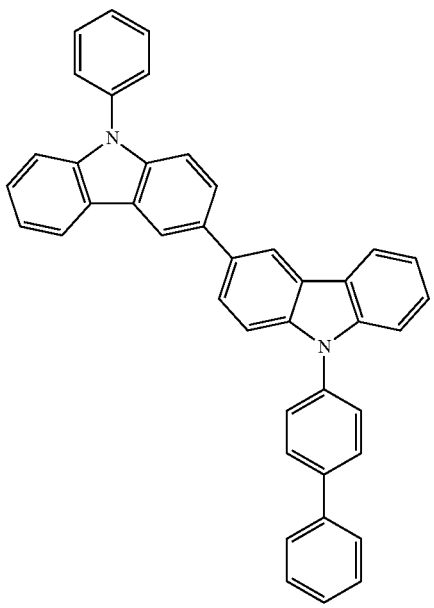
GHA-4
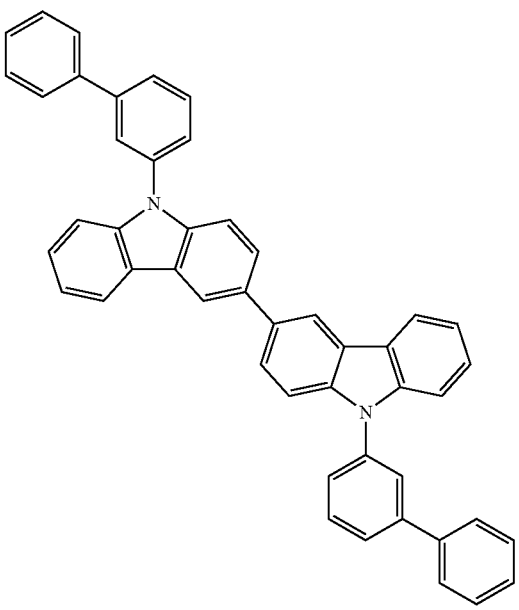

-continued
GHA-5
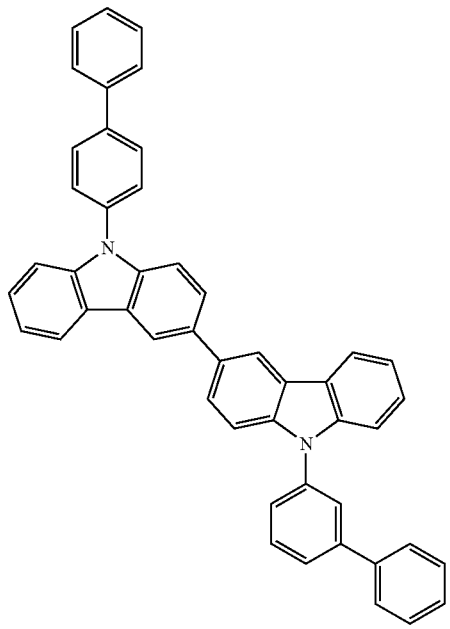
GHA-7
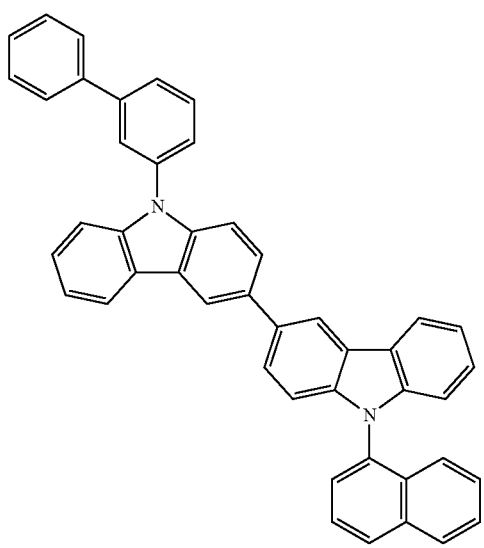
GHA-8
-continued
GHA-9
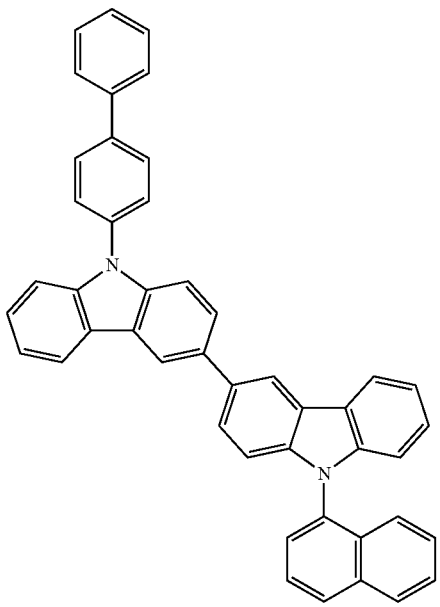
GHA-10
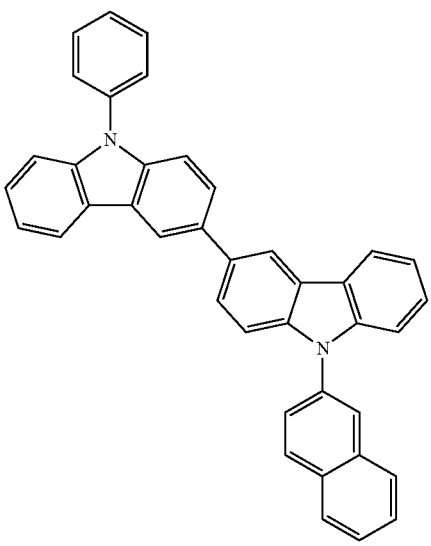

GHA-11
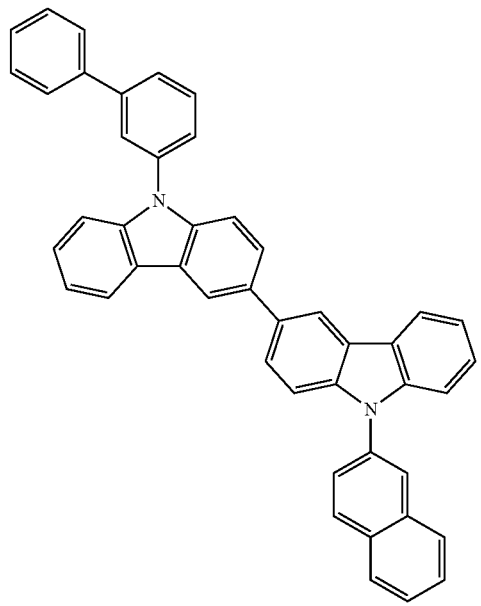
GHA-13
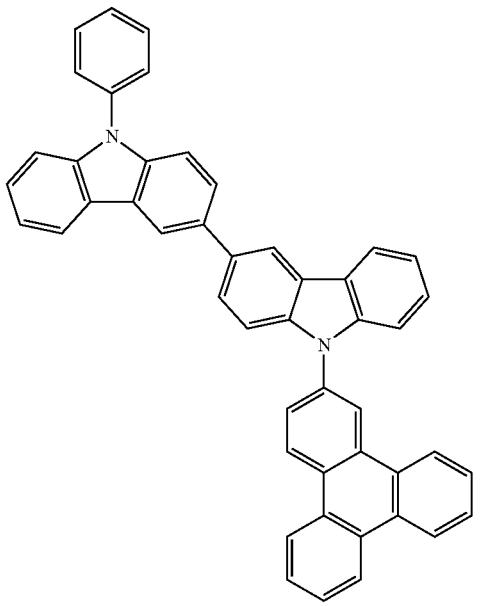
GHA-12
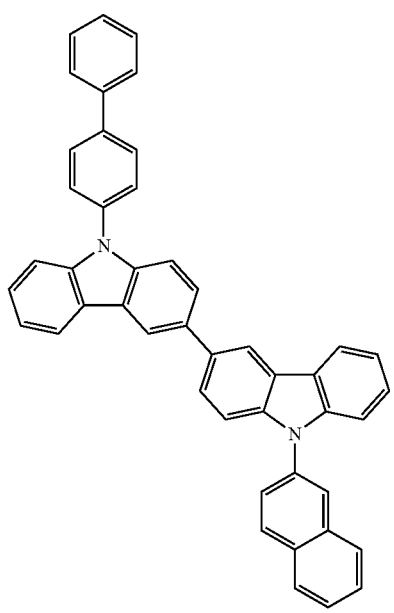
GHA-14
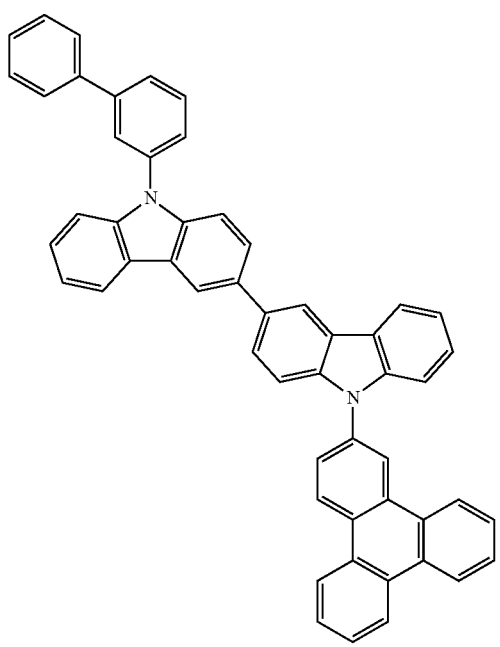

GHA-15
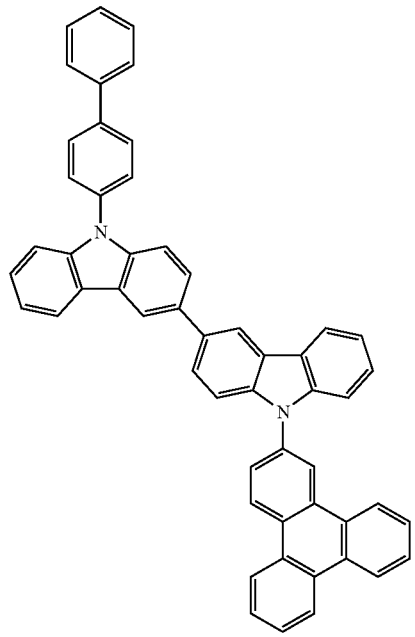
GHA-17
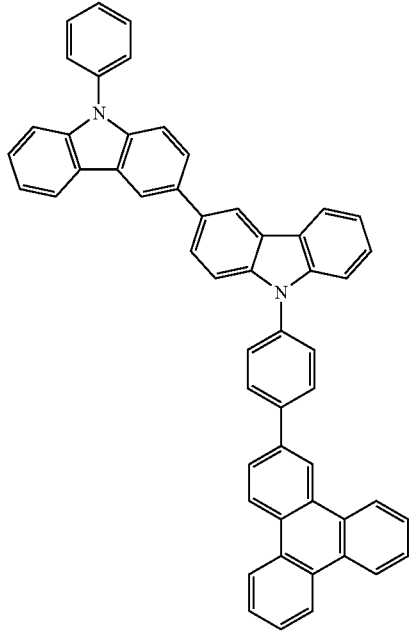
GHA-16
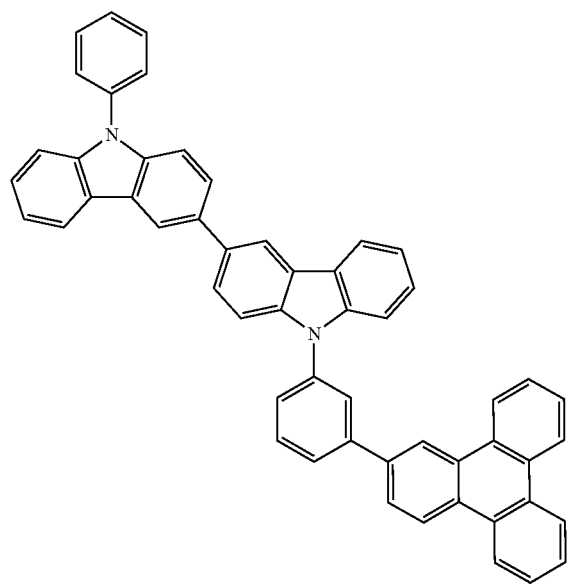
GHA-18
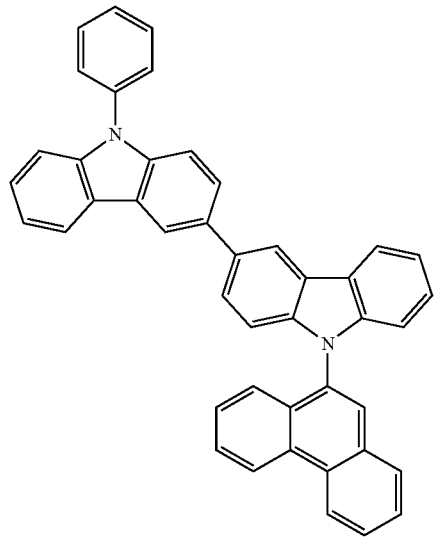

-continued
GHA-19
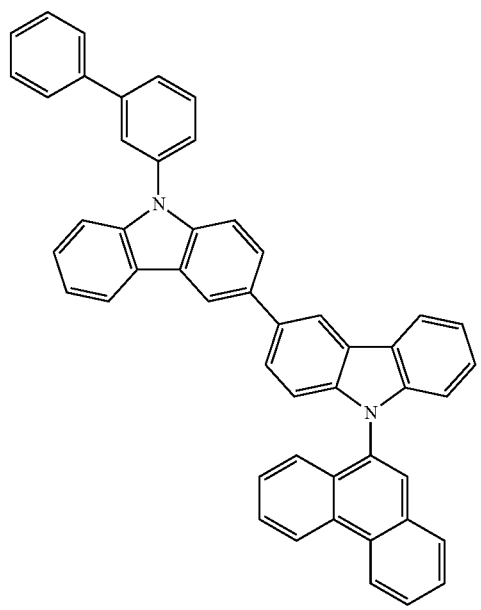
GHA-21
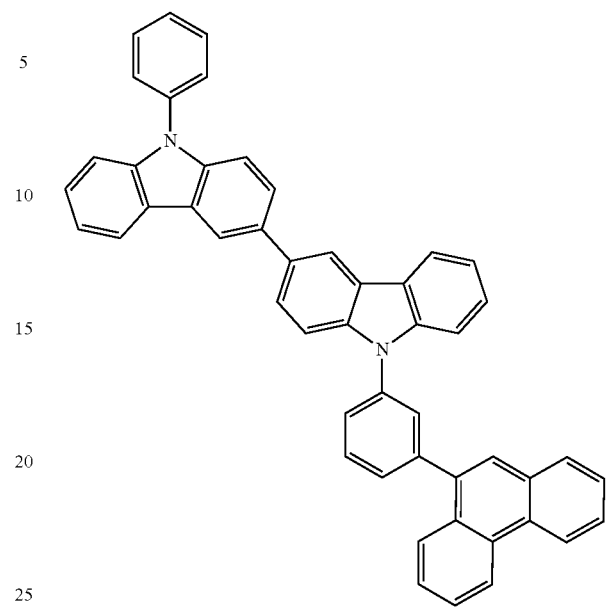
GHA-20
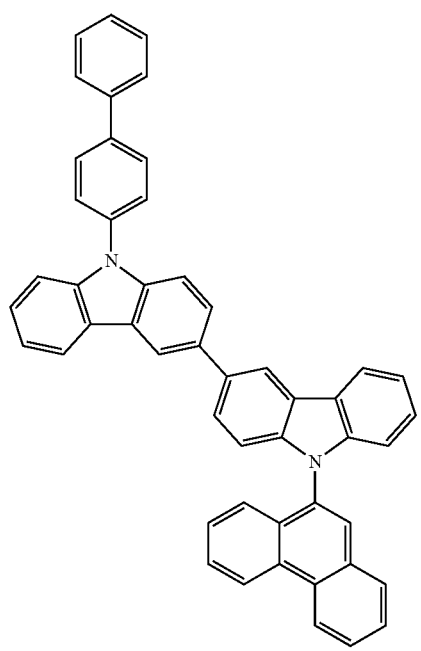
GHA-22
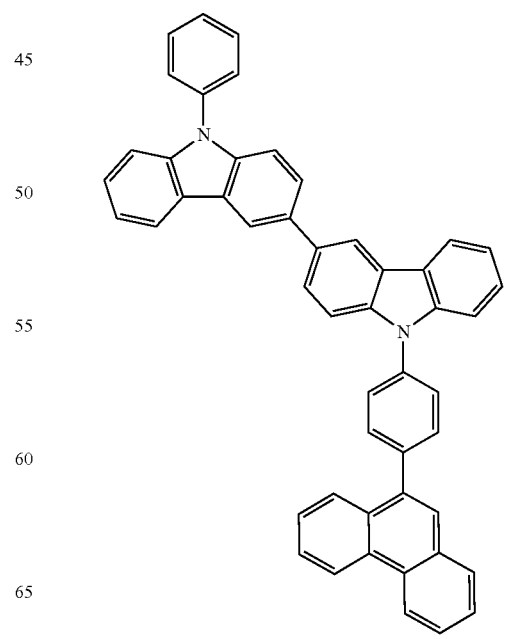

GHA-23
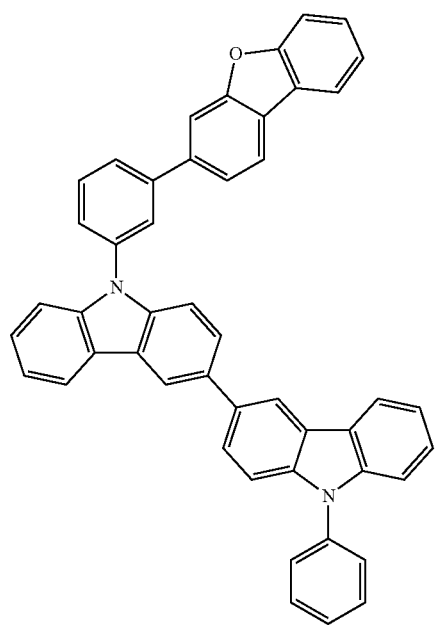
GHA-24
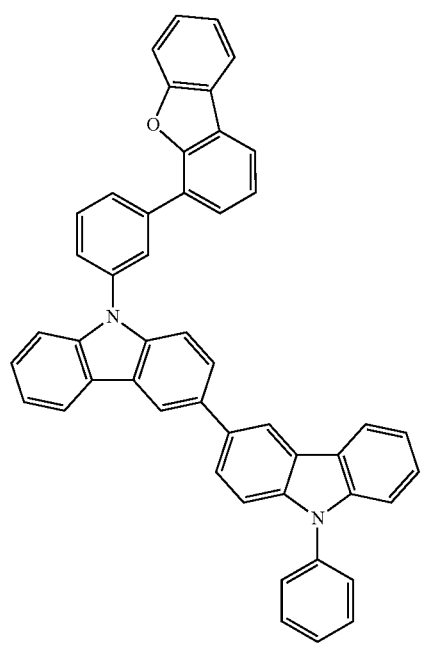
GHA-25
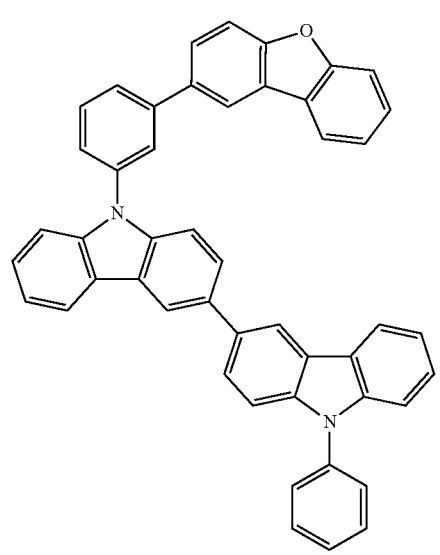
GHA-26
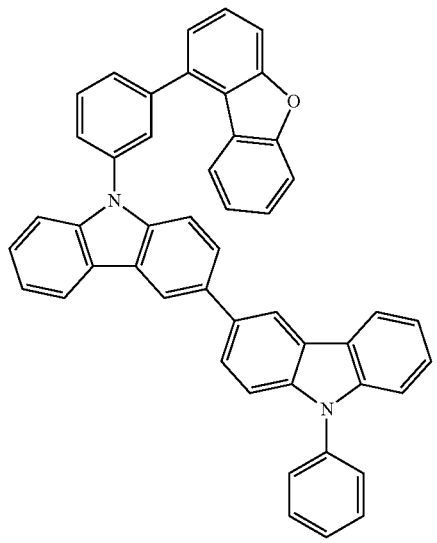

GHA-27
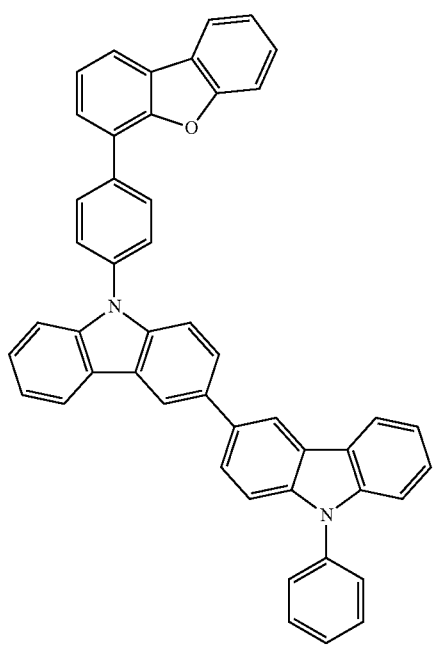
GHA-28
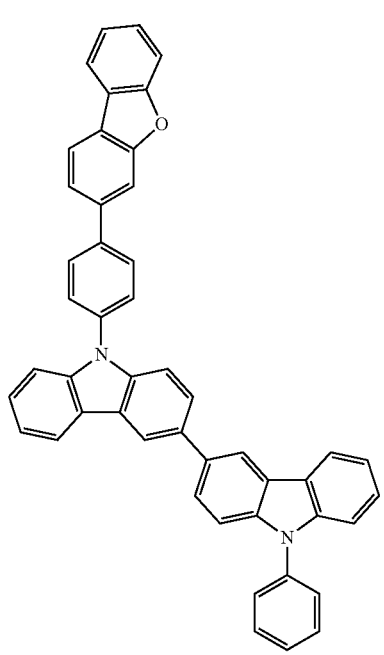
GHA-29
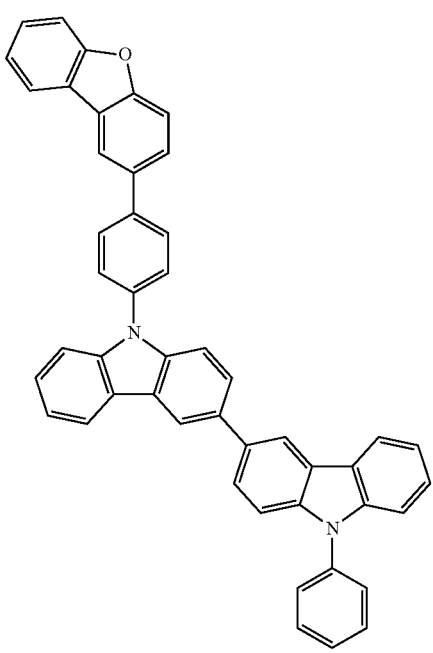
GHA-30
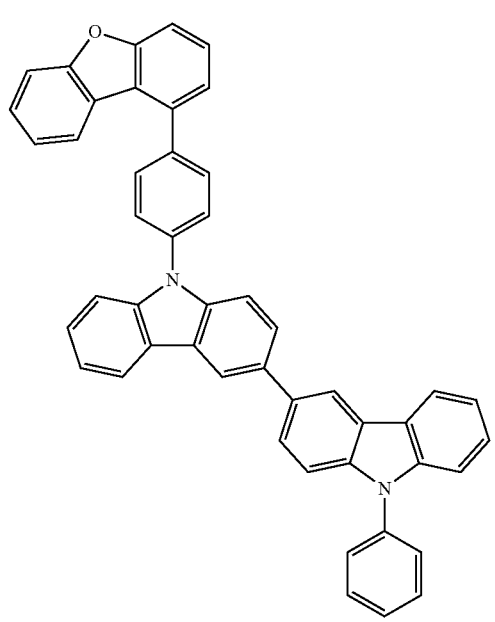

GHA-31
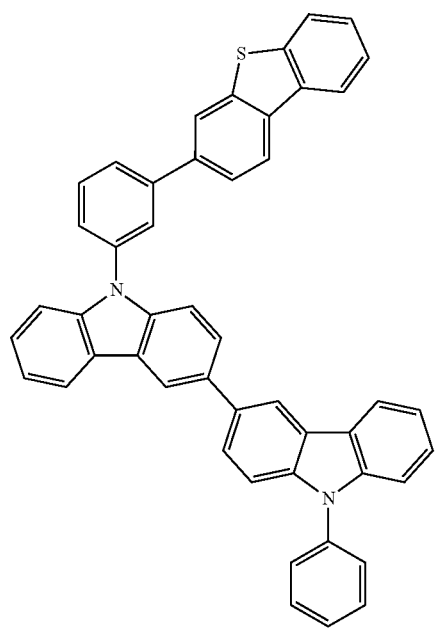
GHA-32
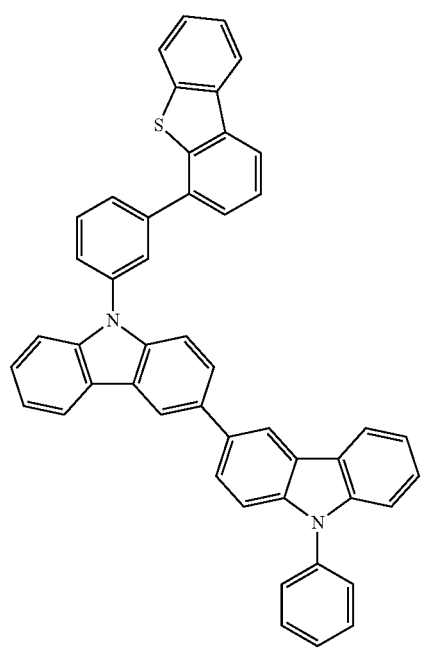
GHA-33
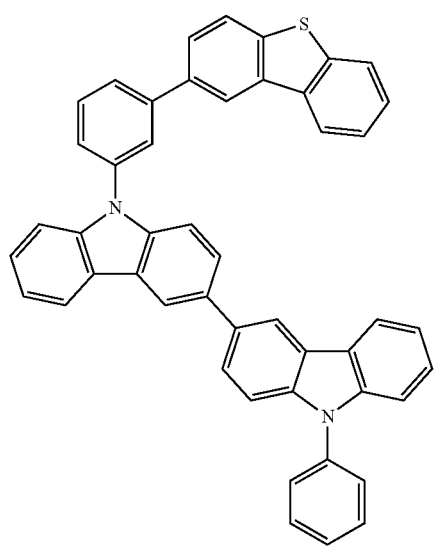
GHA-34
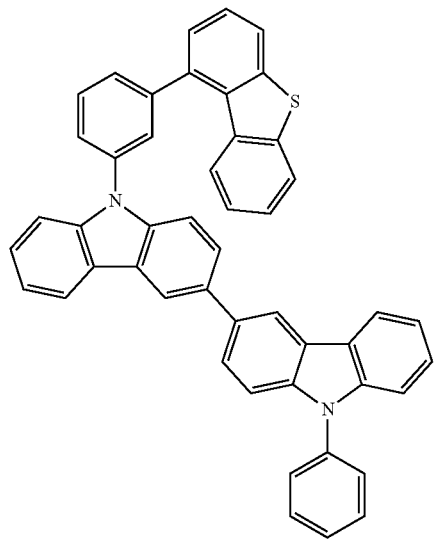

-continued
GHA-35
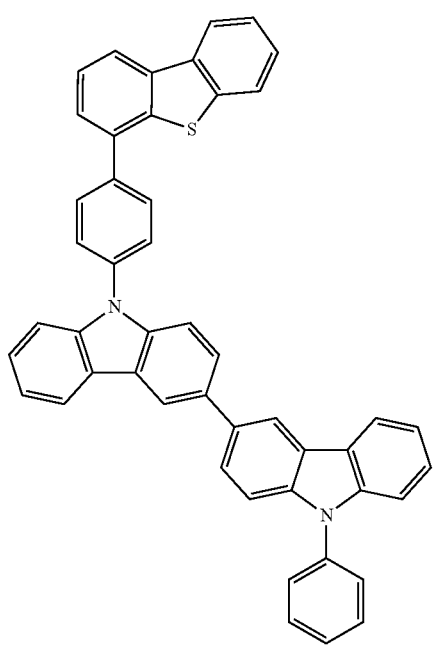
GHA-36
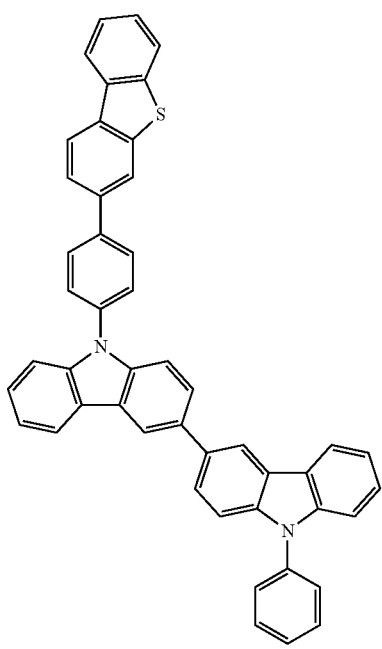
GHA-37
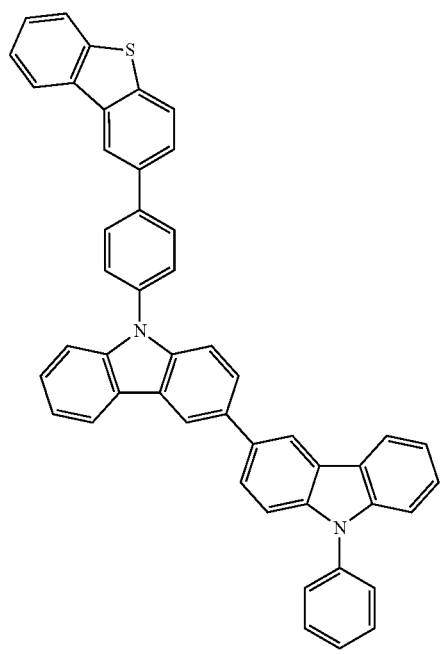
GHA-38
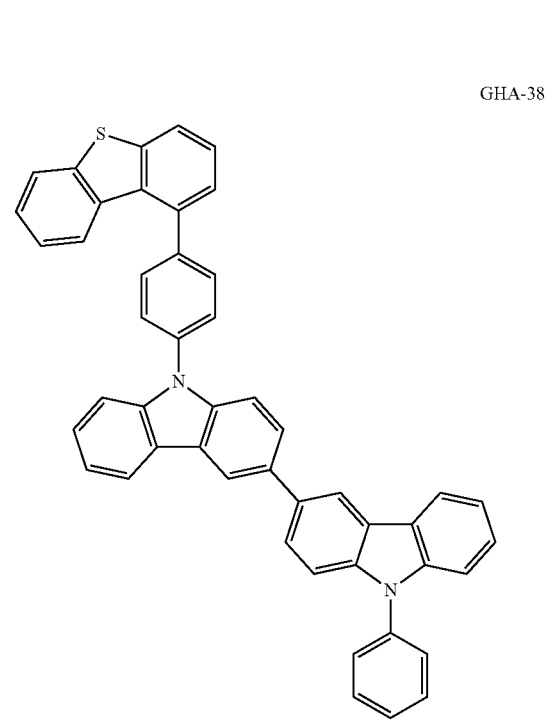

GHA-39
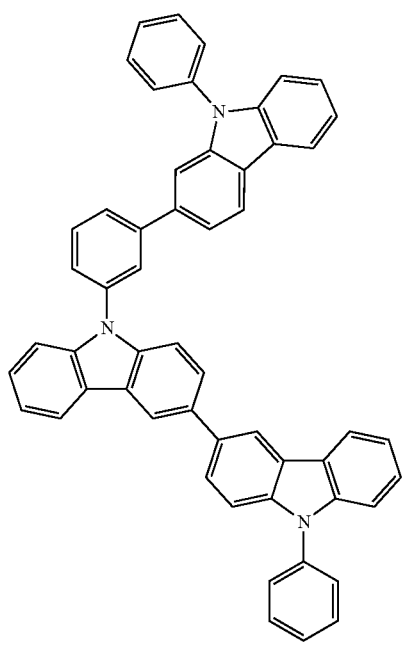
GHA-41
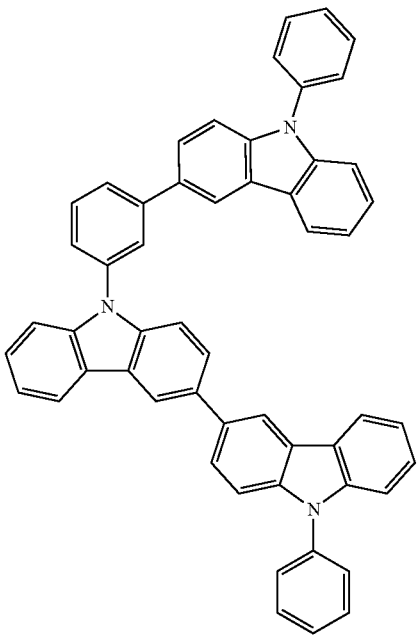
GHA-40
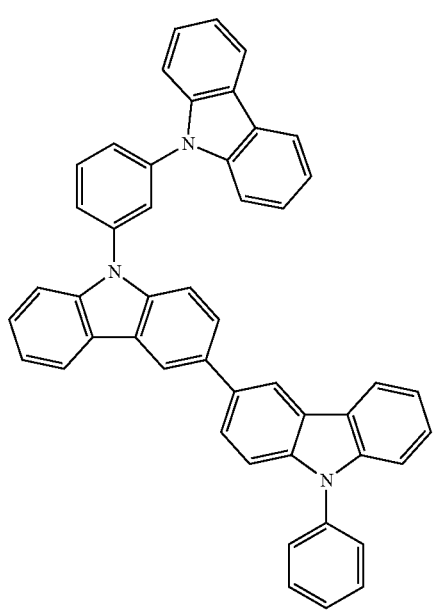
GHA-42
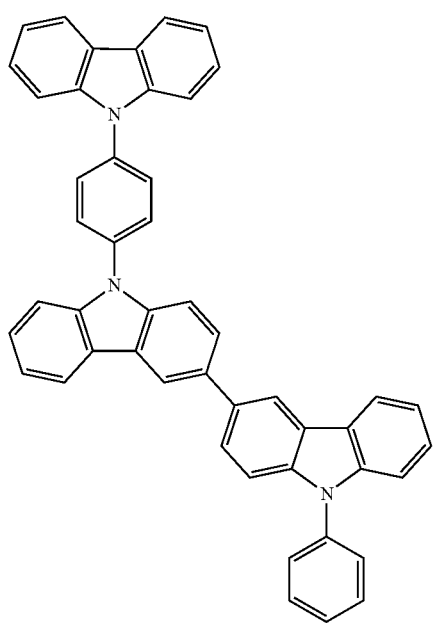

GHA-43
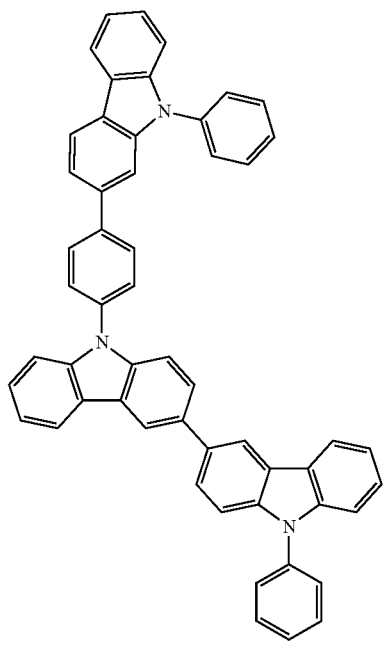
GHB-2
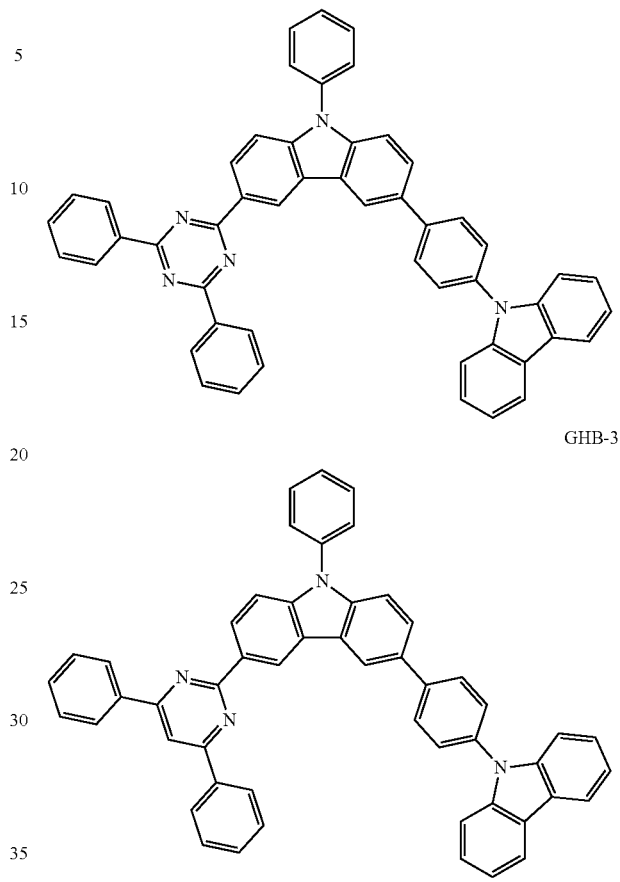
GHB-3
GHA-44
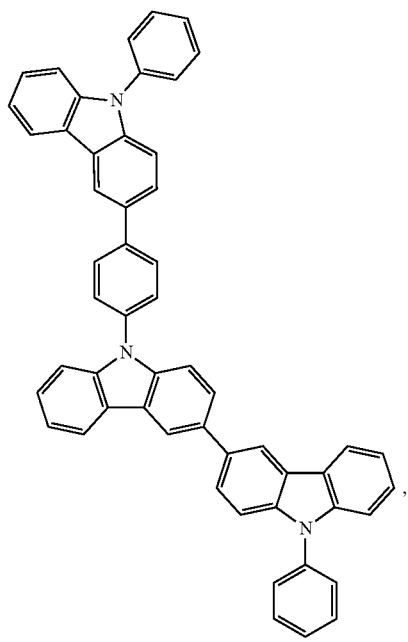
GHB-4
GHB-5
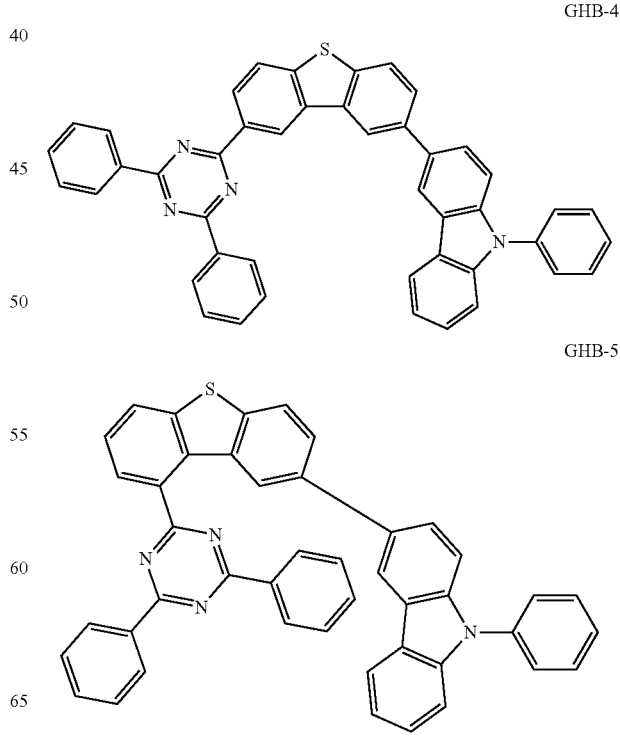
wherein the second green host compound is a compound represented by at least one of the following compounds:

-continued
GHB-6
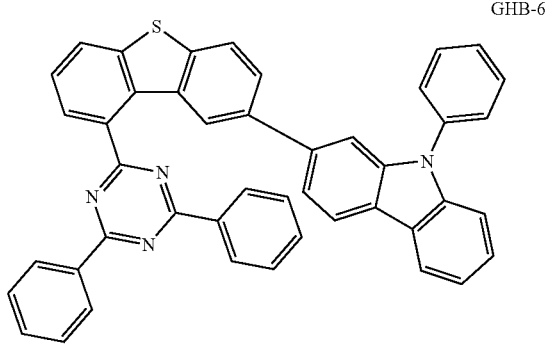
GHB-7
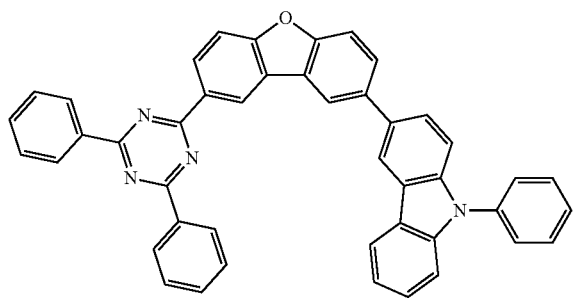
GHB-8
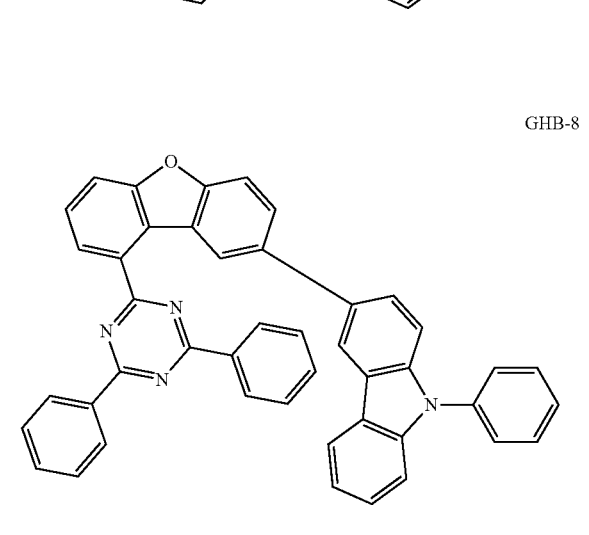
GHB-9
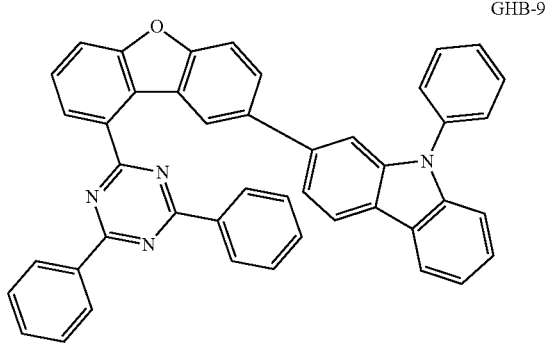
-continued
GHB-10
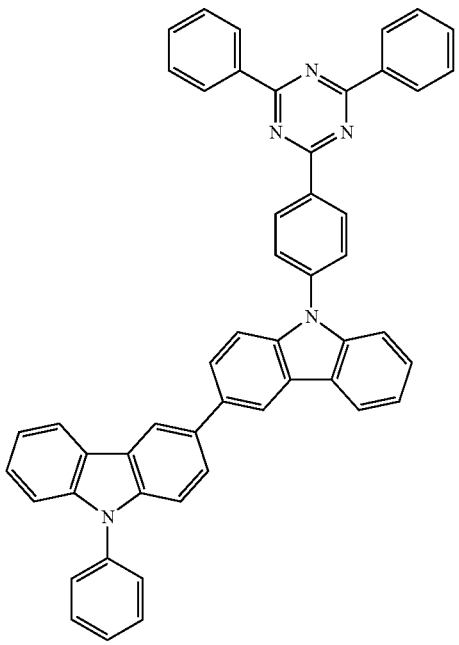
GHB-11
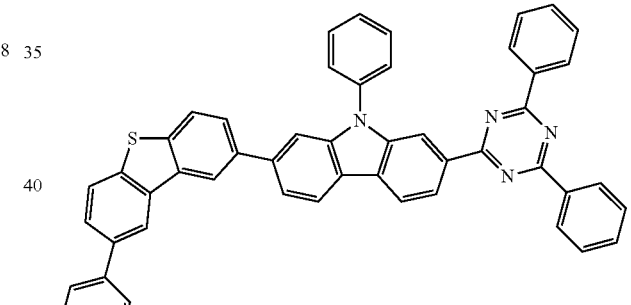
GHB-12
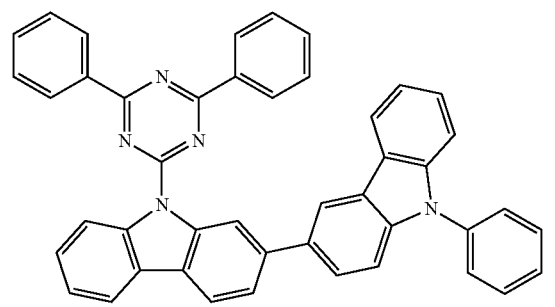

GHB-13
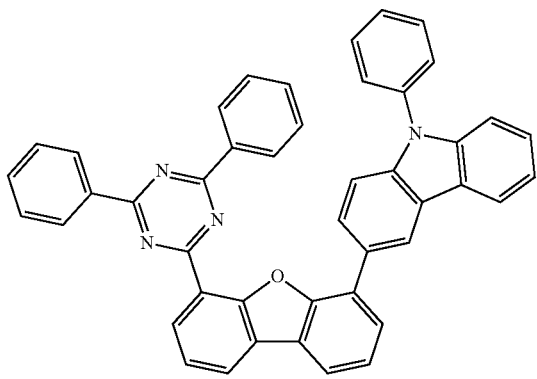
GHB-14
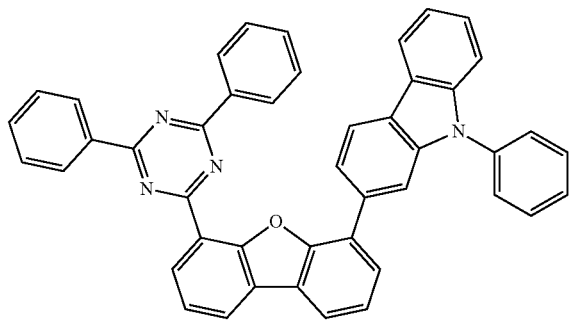
lp;2p
GHB-15
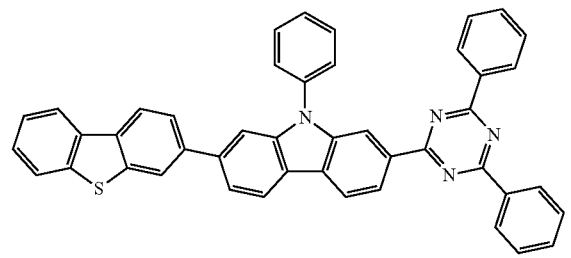
GHB-16
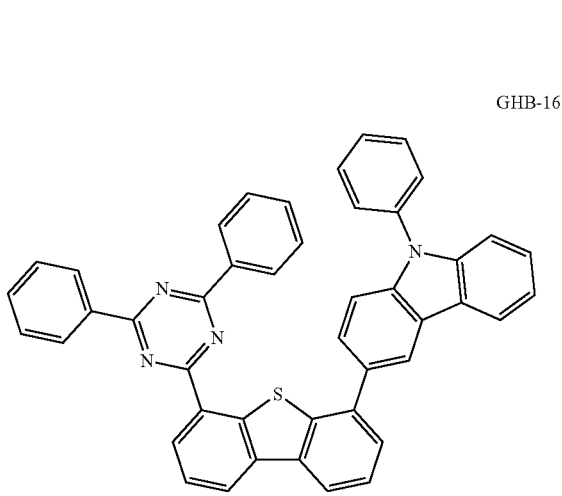
GHB-17
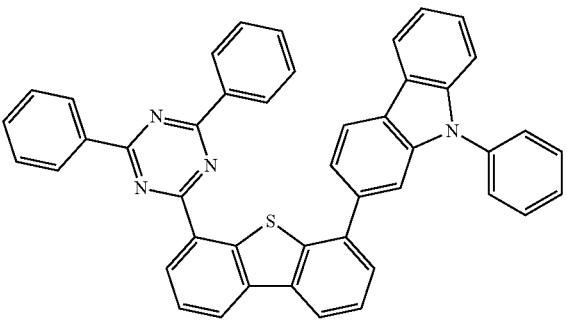
GHB-18
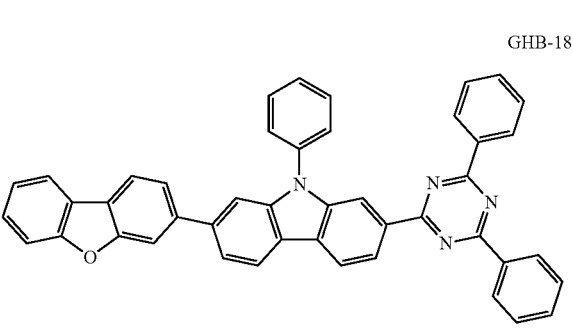
GHB-19
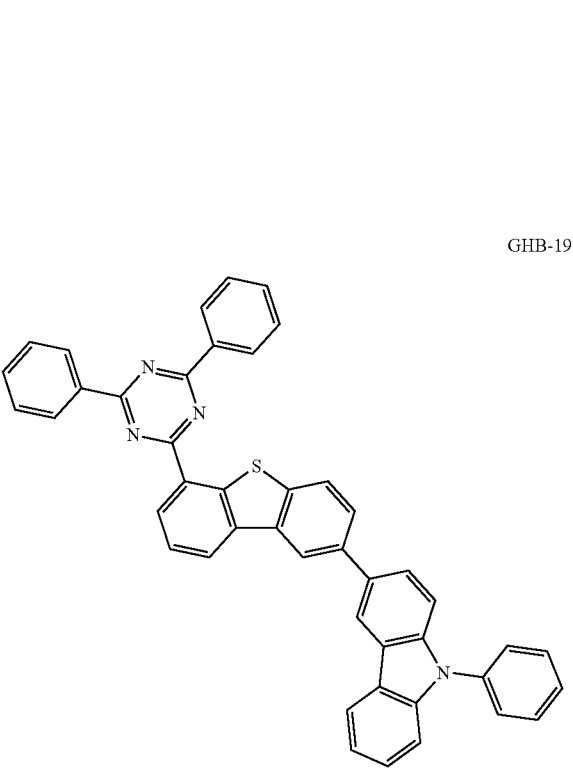

GHB-20

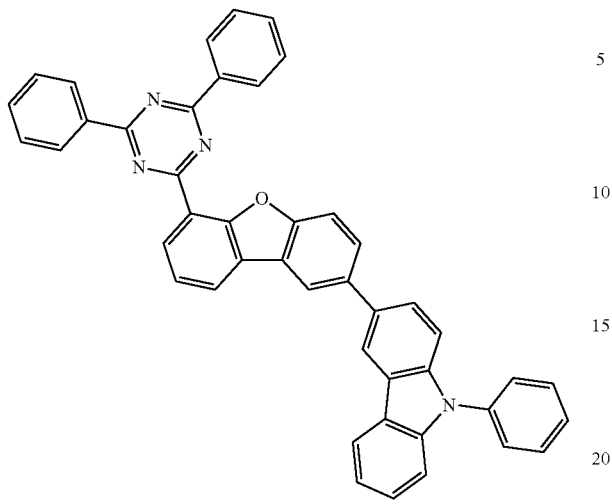

2. The organic electroluminescence device of claim 1, wherein, in an electroluminescence spectrum of the device, a ratio of a maximum peak intensity in a red wavelength band to a maximum peak intensity in a green wavelength band is smaller than 1.5.

3. An organic electroluminescence device, comprising:
an anode;
a cathode; and
a light-emission layer disposed between the anode and the cathode,
wherein the light-emission layer includes a stack of a blue light-emission layer, and a red/green light concurrent-emission sub-stack,
wherein the red/green light concurrent-emission sub-stack includes a stack of a red light-emission layer and a green light-emission layer,
wherein the green light-emission layer is disposed between the red light-emission layer and the cathode,
wherein the red light-emission layer contains a red host compound and a red phosphorescent dopant compound,
wherein the green light-emission layer contains a green host compound and a green phosphorescent dopant compound,
wherein the green host compound includes a mixture of a first green host compound and a second green host compound,
wherein a maximum emission wavelength band of the red phosphorescent dopant compound is in a range of 610 nm to 640 nm,
wherein a maximum emission wavelength band of the green phosphorescent dopant compound is in a range of 510 nm to 540 nm,
wherein a content ratio of the first green host compound to the second green host compound is in a range of 3:7 to 7:3,
wherein a thickness of the red light-emitting layer is in a range of 10 nm to 20 nm, wherein the green light-emitting layer has a thickness in a range of 20 nm to 40 nm,
wherein, in an electroluminescence spectrum of the device, a ratio of a maximum peak intensity in a red wavelength band to a maximum peak intensity in a green wavelength band is smaller than 1.8, wherein the red host compound is selected from the group consisting of:

<RH-4>

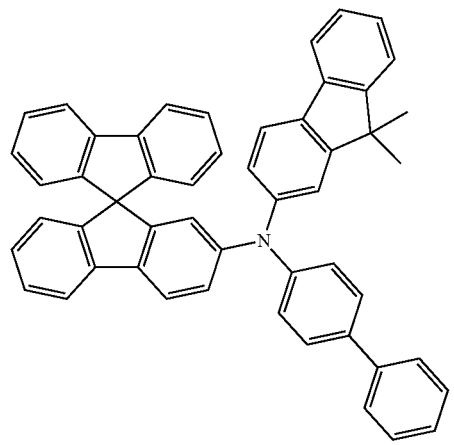

and

<RH-10>

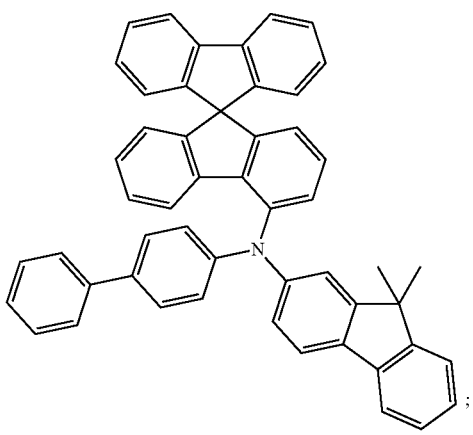

the first green host compound is selected from the group consisting of:

<GHA-2>

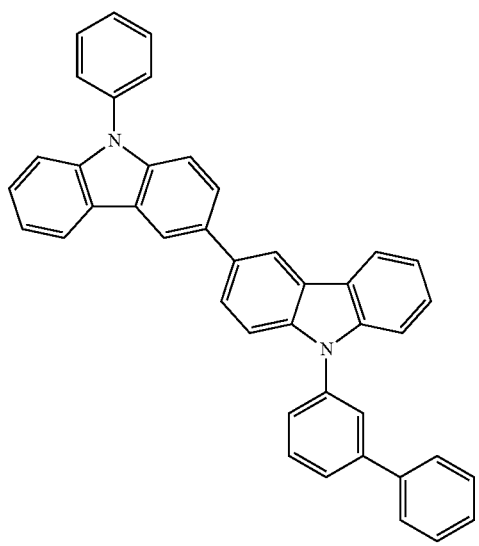

<GHA-3>

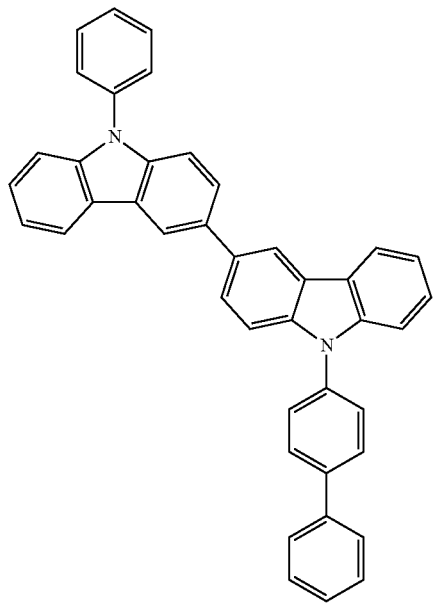

<GHA-13>

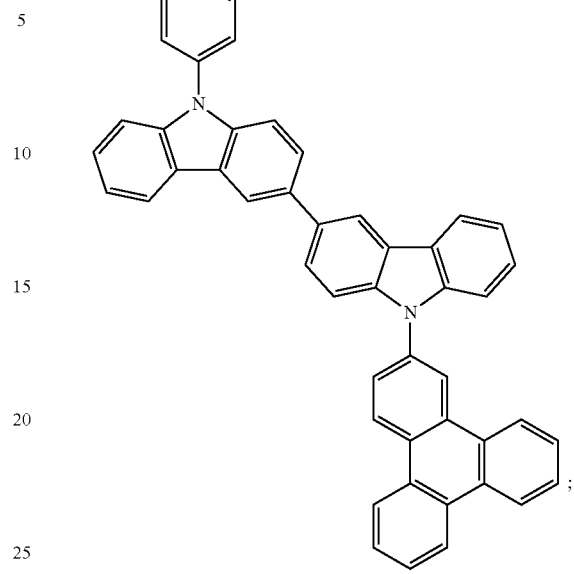

and the second green host compound is selected from the group consisting of:

<GHB-8>

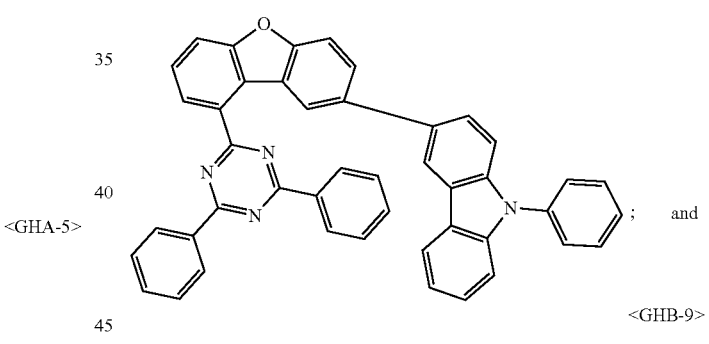

and

<GHB-9>

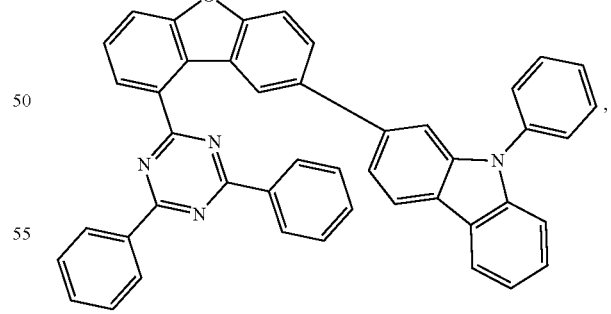

,

<GHA-5>

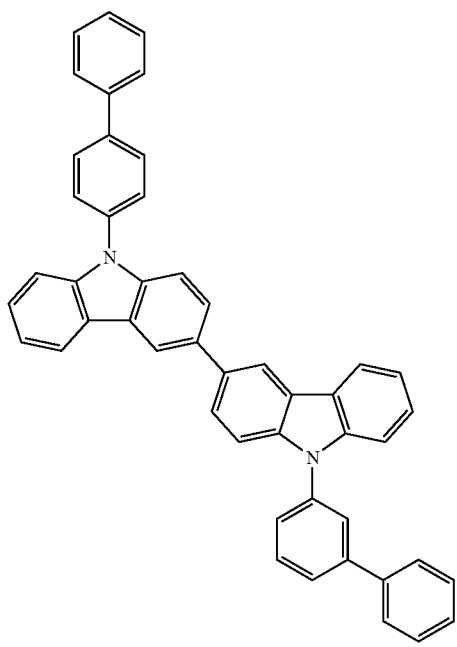

and wherein the red phosphorescent dopant compound comprises at least one compound represented by Chemical Formula 4 or a compound represented by Chemical Formula 5, wherein the green phosphorescent dopant includes at least one of a compound represented by Chemical Formula 6 or a compound represented by Chemical Formula 7:

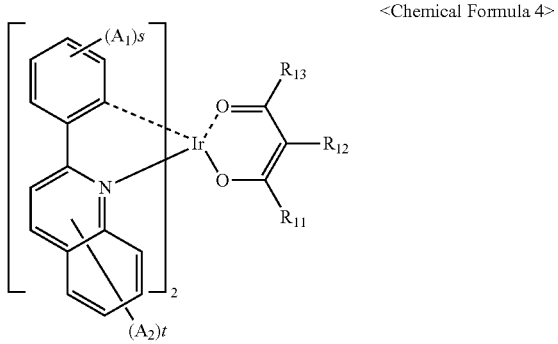

<Chemical Formula 4> wherein, in the Chemical Formula 4, each of $A_1$ and $A_2$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 4, s denotes an integer of 1 to 4, t denotes an integer from 1 to 6, and each of $R_{11}$, $R_{12}$, and $R_{13}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{11}$ and $R_{12}$ are or $R_{12}$ and $R_{13}$ are connected to each other to form a ring,

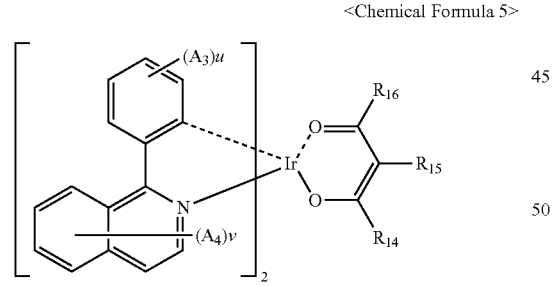

<Chemical Formula 5> wherein, in the Chemical Formula 5, each of $A_3$ and $A_4$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 5, u denotes an integer of 1 to 4, v denotes an integer from 1 to 6, and each of $R_{14}$, $R_{15}$, and $R_{16}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{14}$ and $R_{15}$ are or $R_{15}$ and $R_{16}$ are connected to each other to form a ring,

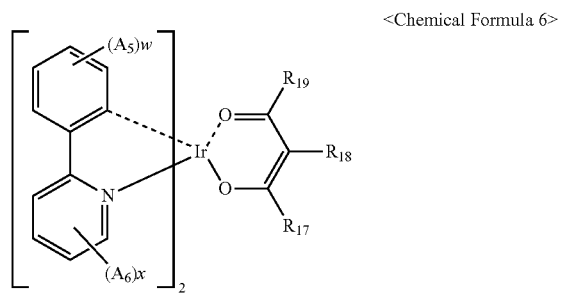

<Chemical Formula 6> wherein, in the Chemical Formula 6, each of $A_5$ and $A_6$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 6, each of w and x independently denotes an integer of 1 to 4, and each of $R_{17}$, $R_{18}$, and $R_{19}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{17}$ and $R_{18}$ are or $R_{18}$ and $R_{19}$ are connected to each other to form a ring,

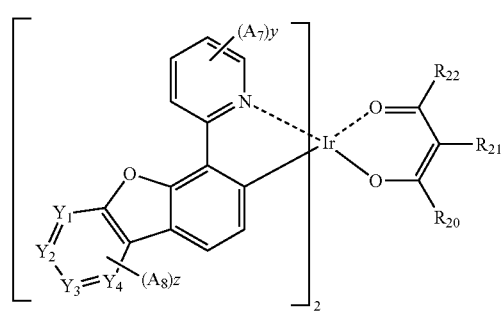

wherein, in the Chemical Formula 7, each of $A_7$ and $A_8$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 7, y denotes an integer of 1 to 4, z denotes an integer from 1 to 3, and each of $R_{20}$, $R_{21}$, and $R_{22}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{20}$ and $R_{21}$ are or $R_{21}$ and $R_{22}$ are connected to each other to form a ring, and wherein, in the Chemical Formula 7, each of $Y_1$, $Y_2$, $Y_3$, and $Y_4$ independently represents N or CR', wherein R' represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, and a substituted or unsubstituted C5 to C9 heteroaryl group.

4. The organic electroluminescence device of claim 3, further comprising an electron transport layer, and wherein the electron transport layer comprises a compound of Chemical Formula (III):

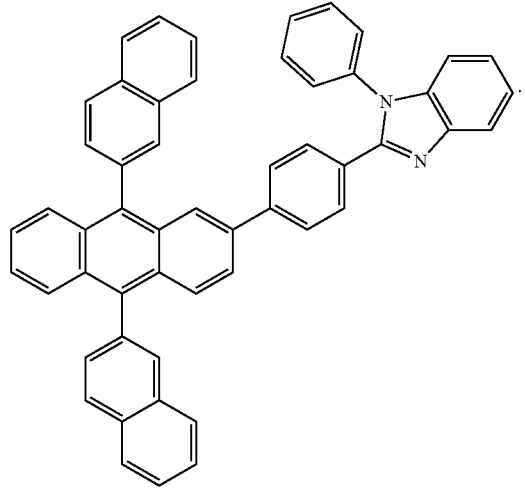 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

5. The organic electroluminescence device of claim 3, further comprising a hole transport layer, and wherein the hole transport layer comprises a compound of Chemical Formula (II):

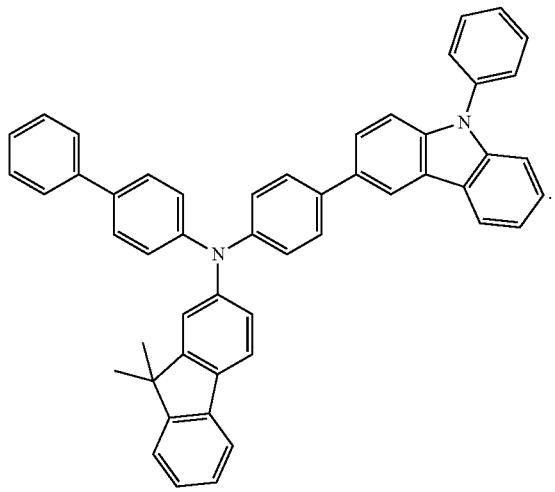 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

6. The organic electroluminescence device of claim 3, wherein the blue light-emission layer comprises a blue host compound and a blue dopant compound.

7. The organic electroluminescence device of claim 6, wherein the blue host compound comprises an anthracene based compound.

8. The organic electroluminescence device of claim 6, wherein the blue dopant compound comprises a pyrene based dopant compound or a boron-containing dopant compound.

9. The organic electroluminescence device of claim 3, wherein the stack of the blue light-emission layer further comprises a hole transport layer and an electron transport layer,
wherein the hole transport layer, the blue light-emission layer, and the electron transport layer are sequentially stacked.

10. The organic electroluminescence device of claim 3, wherein the red/green light concurrent-emission sub-stack further comprises a hole transport layer and an electron transport layer, and
wherein the hole transport layer, the red/green light concurrent-emission sub-stack, and the electron transport layer are sequentially stacked.

11. An organic electroluminescence device, comprising:
an anode;
a cathode; and
a light-emission layer disposed between the anode and the cathode,
wherein the light-emission layer includes a stack of a blue light-emission layer, and a red/green light concurrent-emission sub-stack,
wherein the red/green light concurrent-emission sub-stack includes a stack of a red light-emission layer and a green light-emission layer,
wherein the green light-emission layer is disposed between the red light-emission layer and the cathode,
wherein the red light-emission layer contains a red host compound and a red phosphorescent dopant compound,
wherein the green light-emission layer contains a green host compound and a green phosphorescent dopant compound,
wherein a maximum emission wavelength band of the red phosphorescent dopant compound is in a range of 610 nm to 640 nm, wherein a maximum emission wavelength band of the green phosphorescent dopant compound is in a range of 510 nm to 540 nm, wherein a content ratio of the first green host compound to the second green host compound is in a range of 3:7 to 7:3, wherein, in an electroluminescence spectrum of the device, a ratio of a maximum peak intensity in a red wavelength band to a maximum peak intensity in a green wavelength band is smaller than 1.8, wherein the green host compound includes a mixture of a first green host compound and a second green host compound;

wherein the red light-emission layer contains a red host compound represented by at least one of the following compounds:

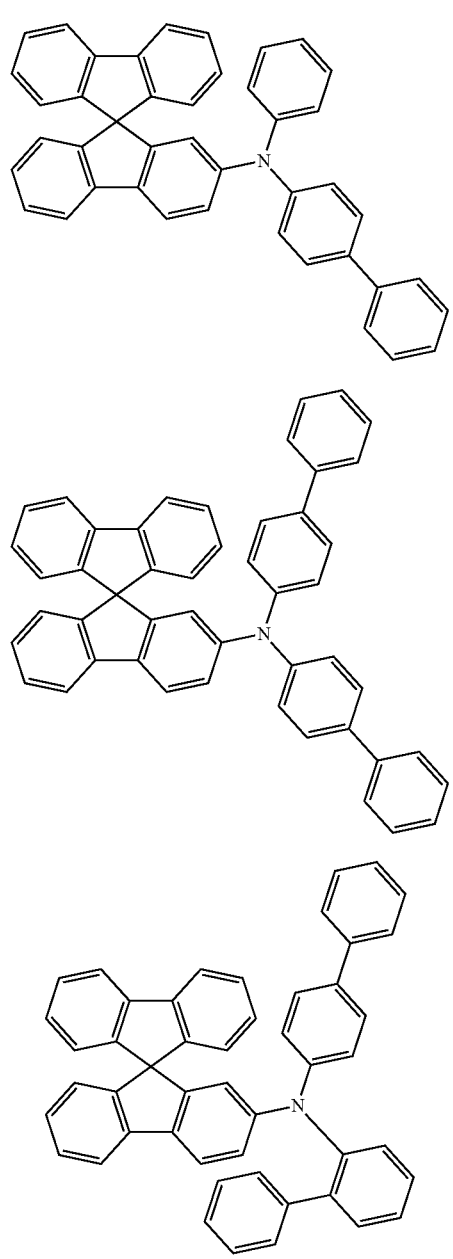

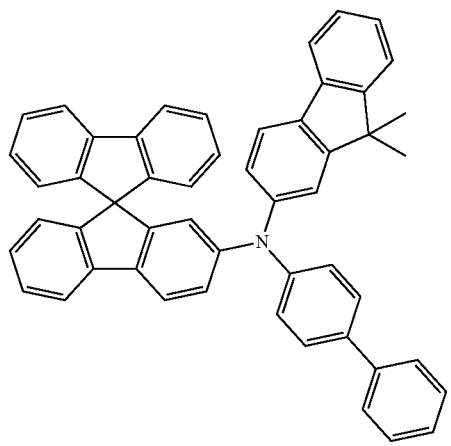

-continued
RH-8
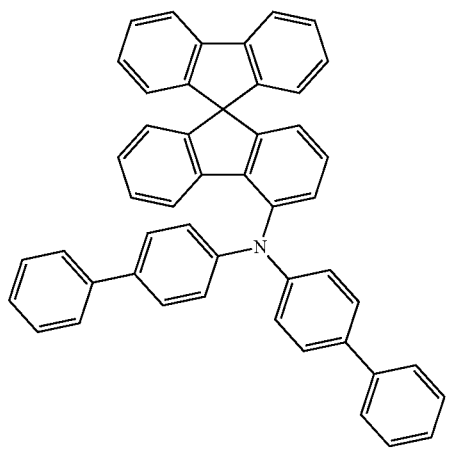
RH-9
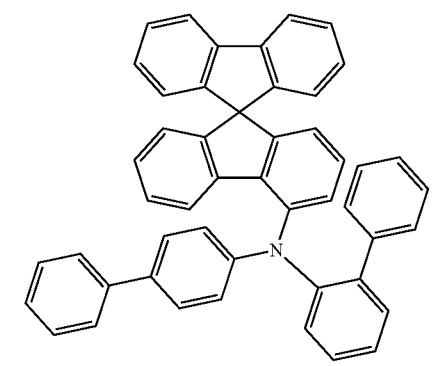
RH-10
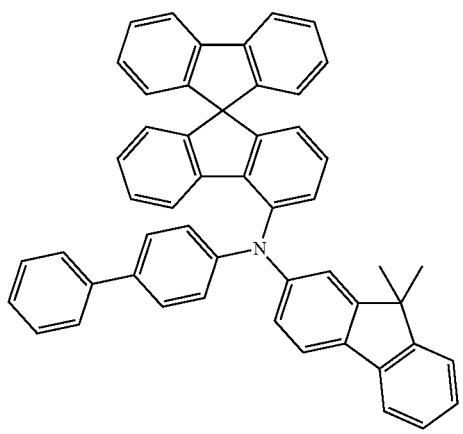
-continued
RH-11
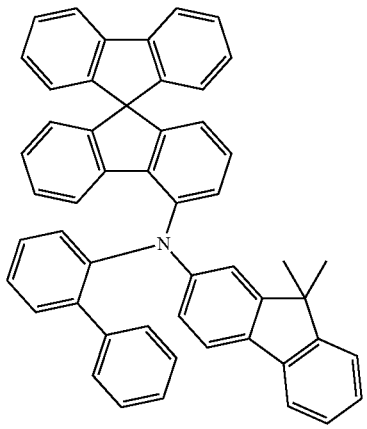
RH-12
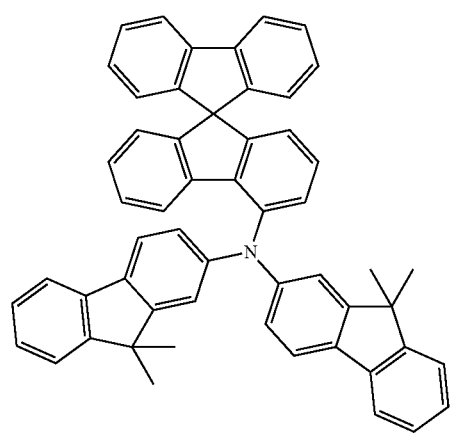
wherein the first green host compound is a compound represented by at least one of the following compounds:
GHA-1
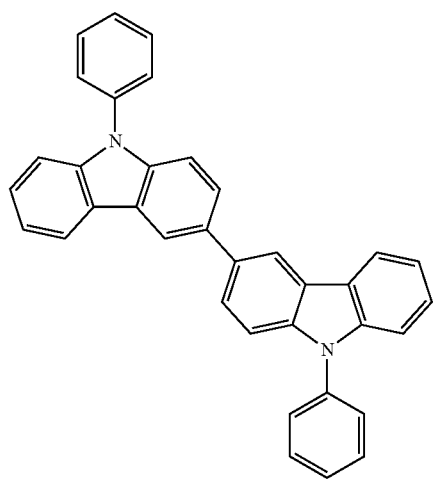

GHA-2
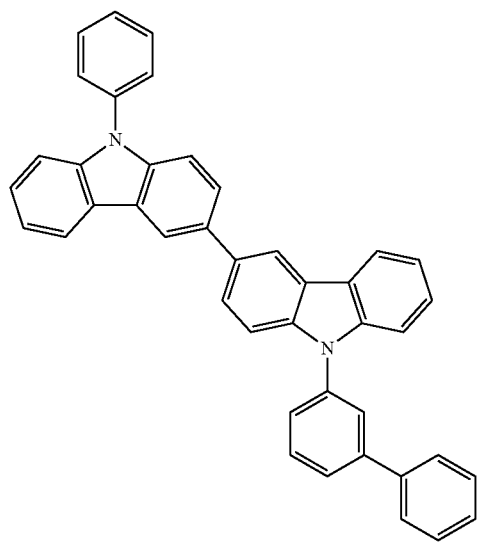
GHA-4
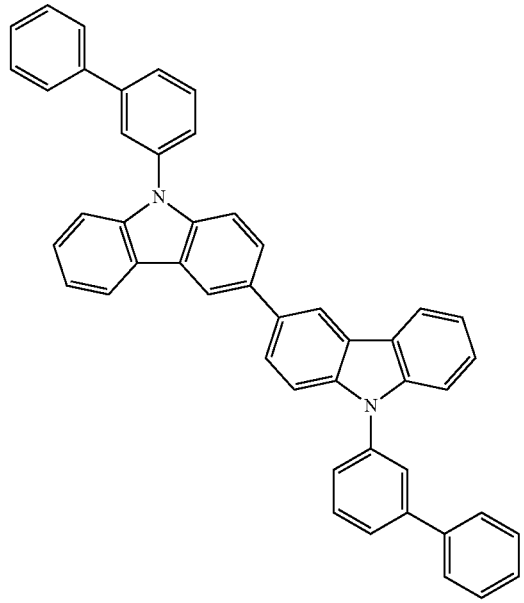
GHA-3
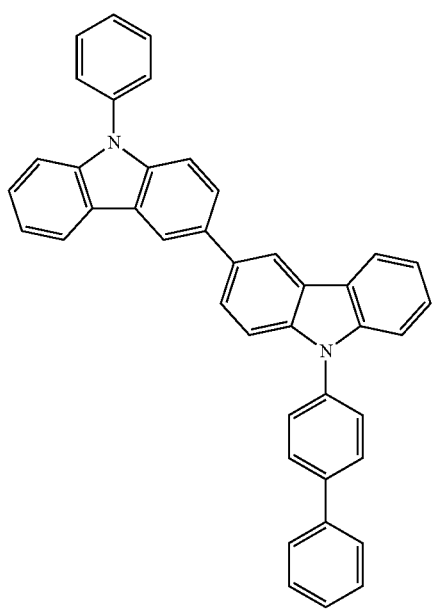
GHA-5
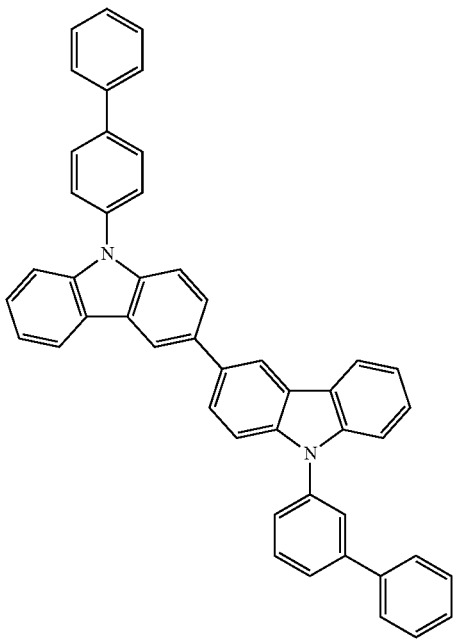

GHA-7
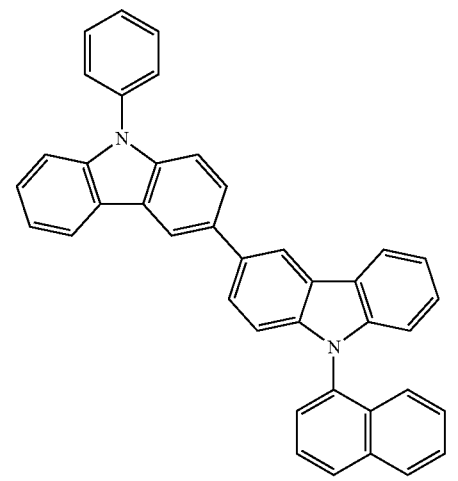
GHA-10
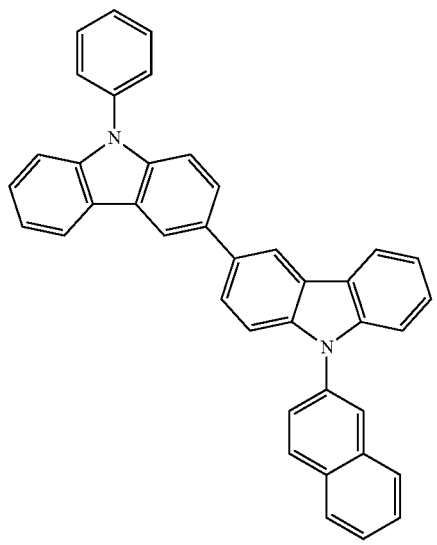
GHA-8
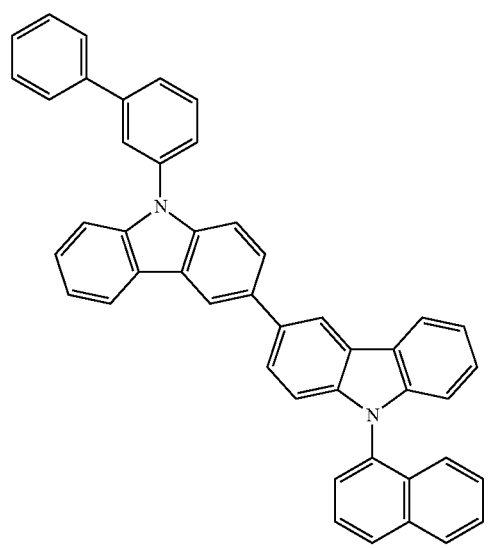
GHA-9
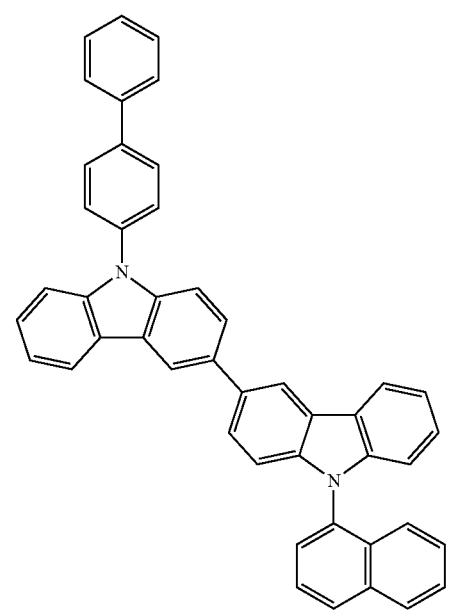
GHA-11

GHA-12
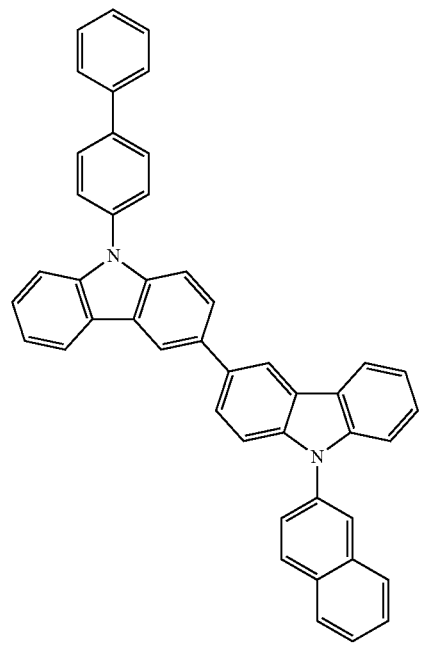
GHA-14
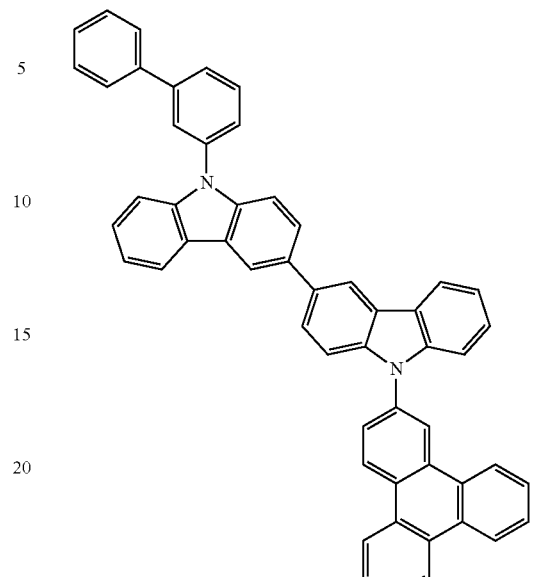
GHA-13
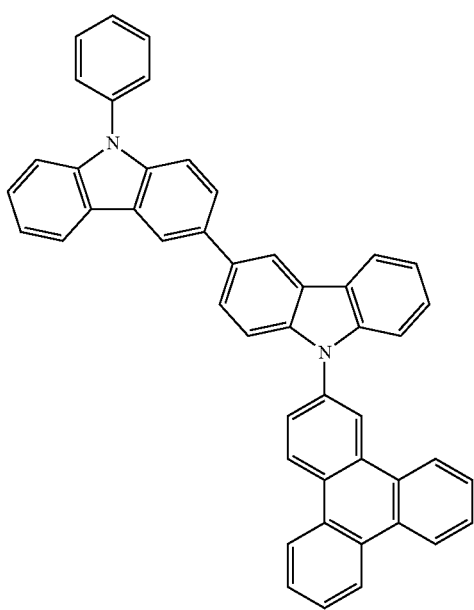
GHA-15
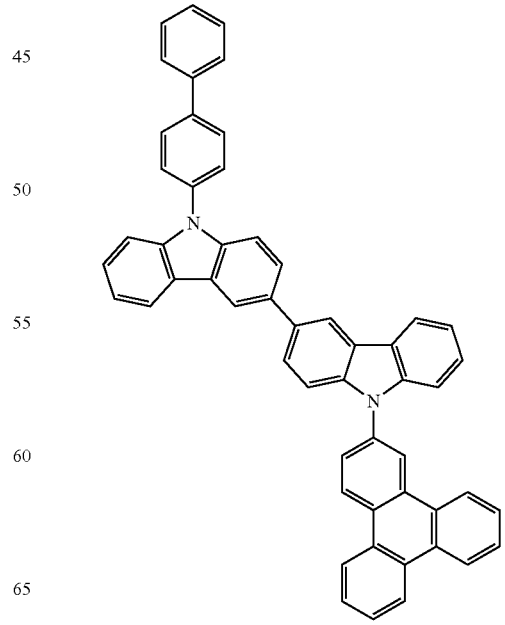

GHA-16
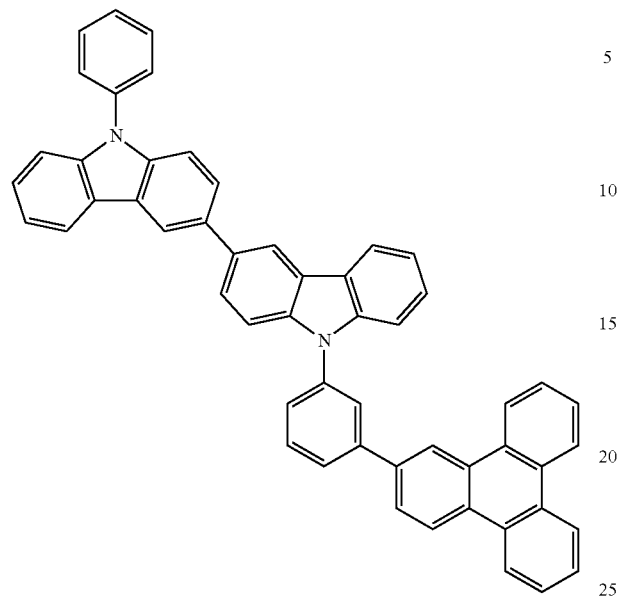
GHA-17
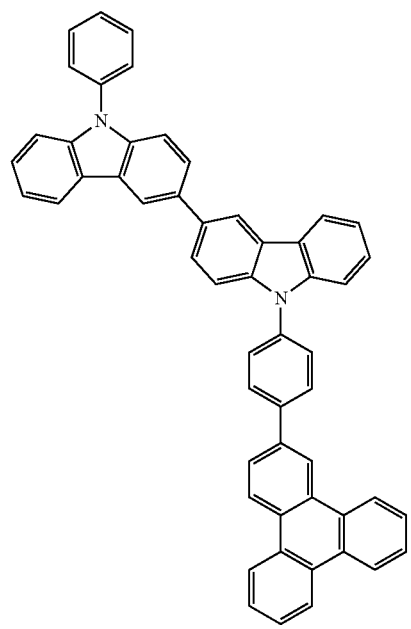
GHA-18
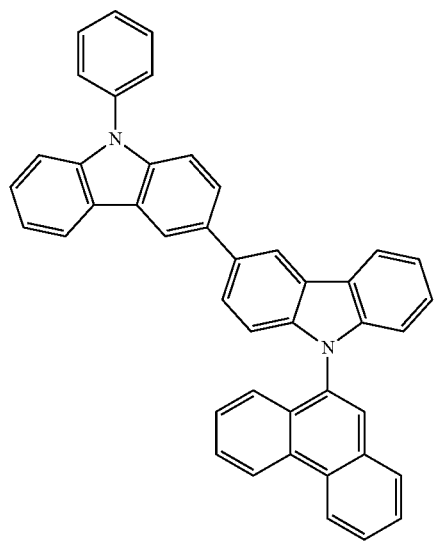
GHA-19
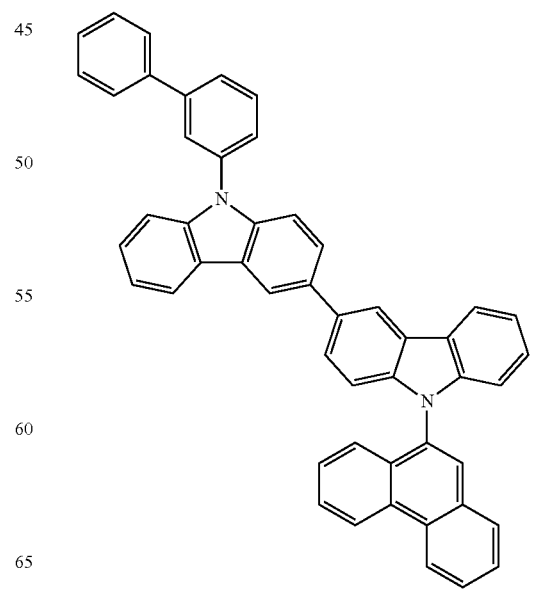

GHA-20
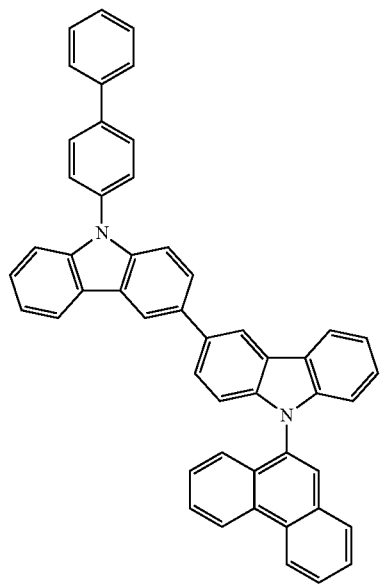
GHA-21
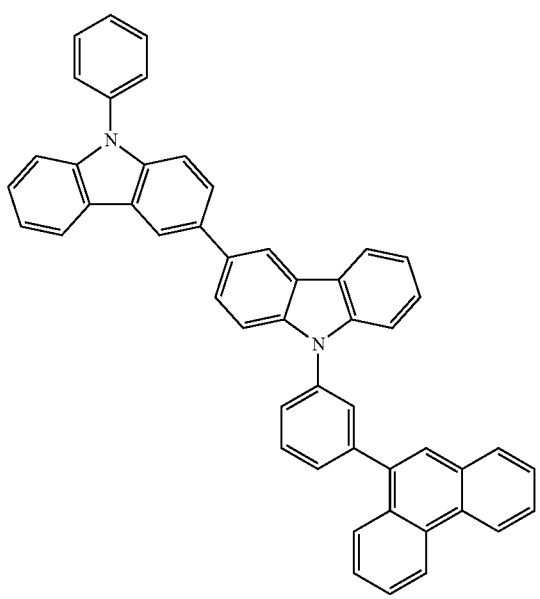
GHA-22
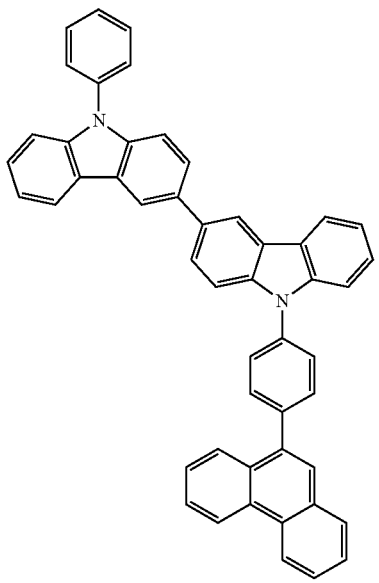
GHA-23
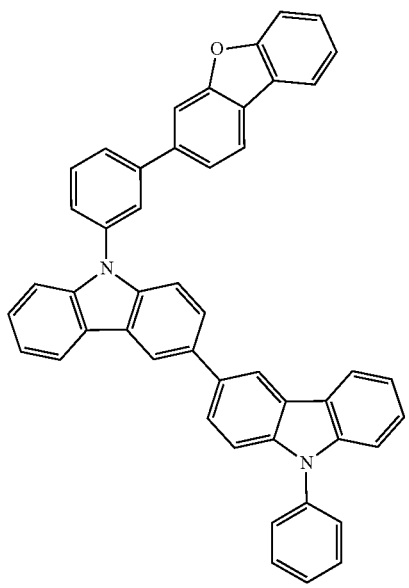

GHA-24
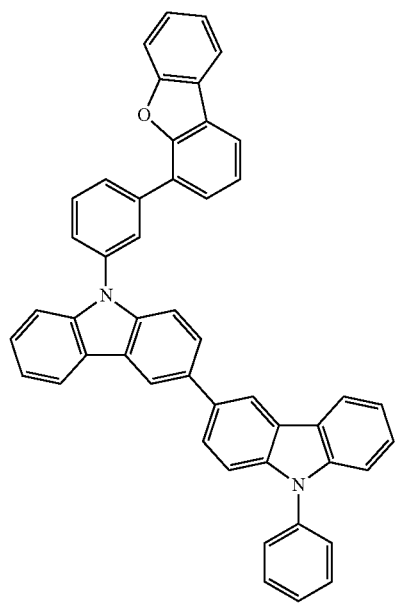
GHA-26
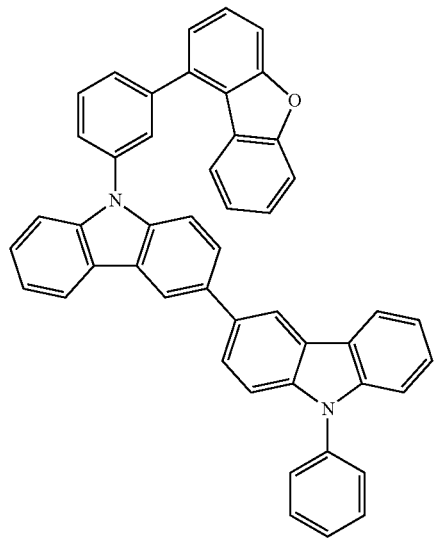
GHA-25
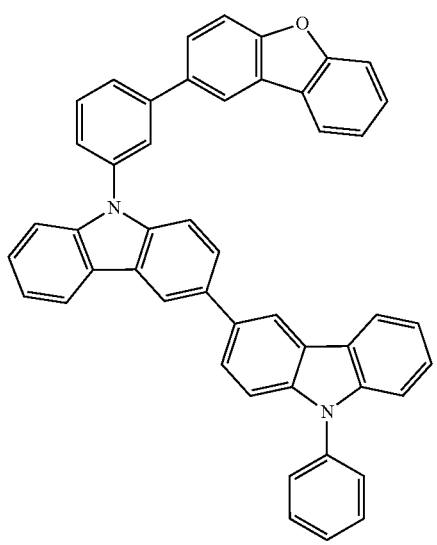
GHA-27
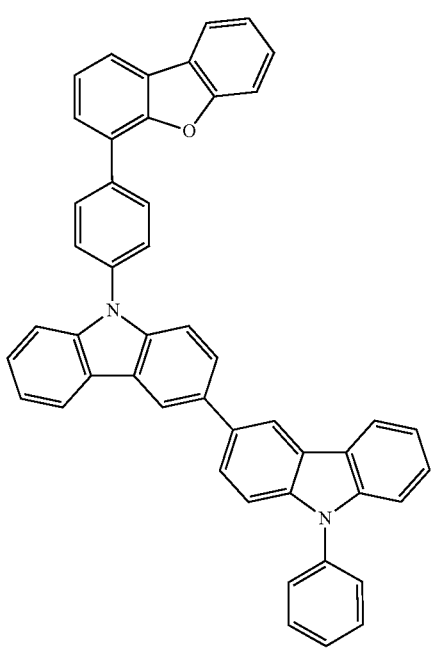

GHA-28
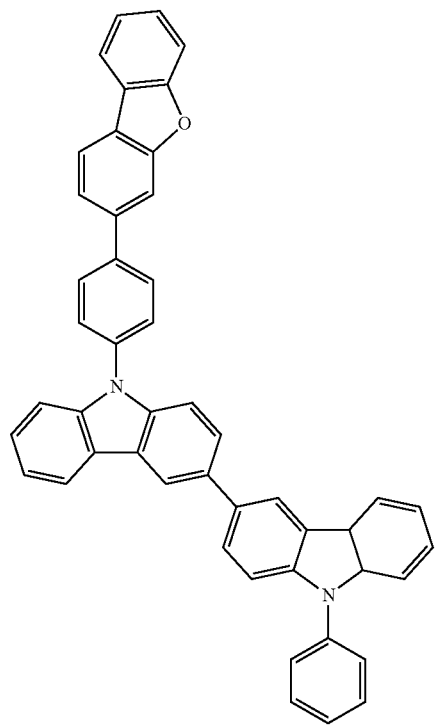
GHA-29
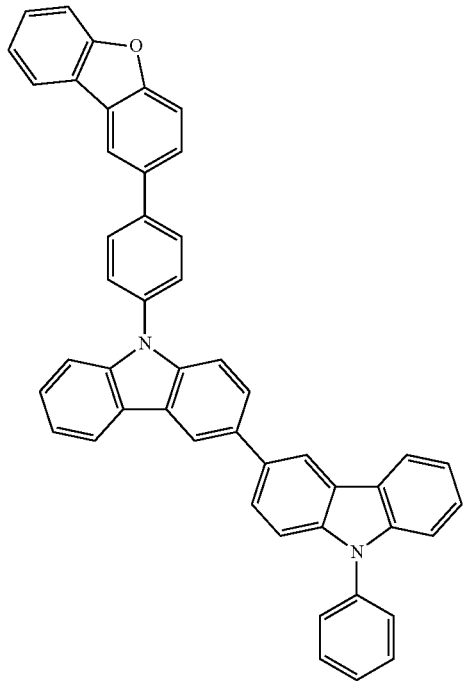
GHA-30
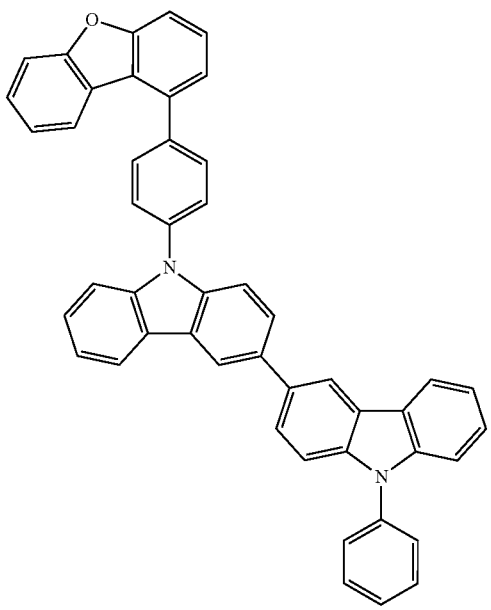
GHA-31
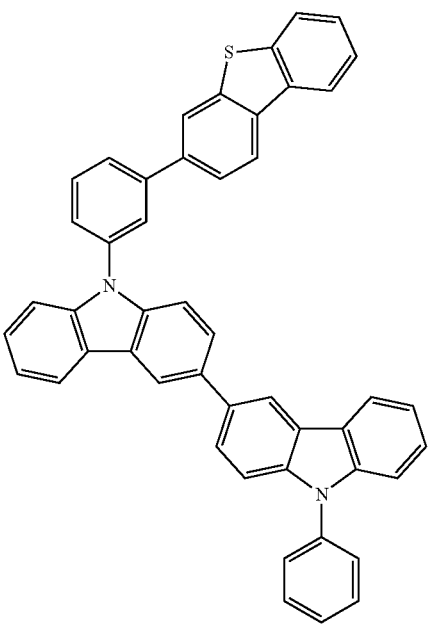

GHA-32
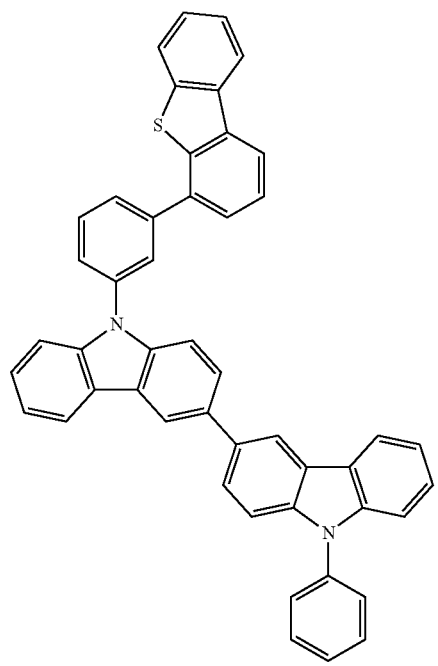
GHA-33
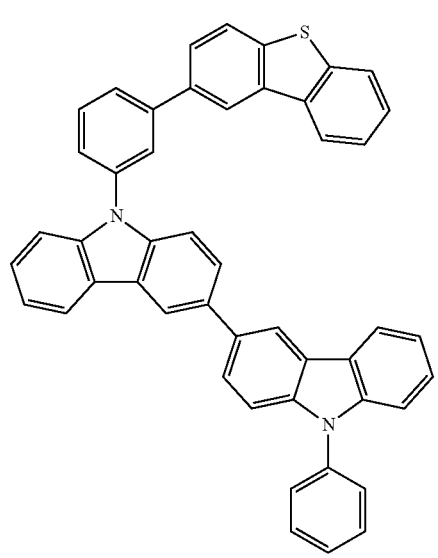
GHA-34
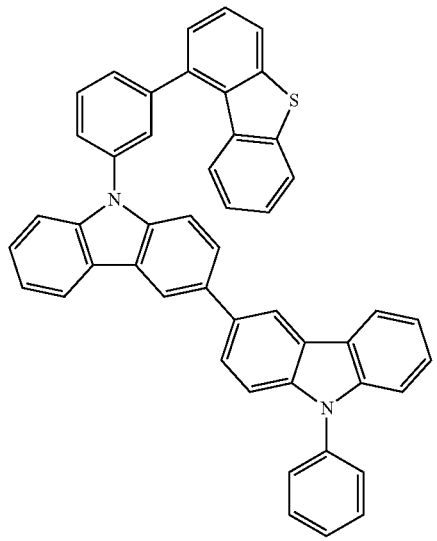
GHA-35
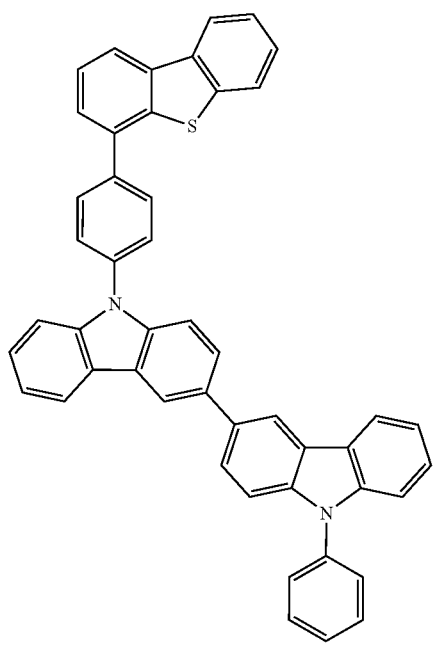

-continued
GHA-36
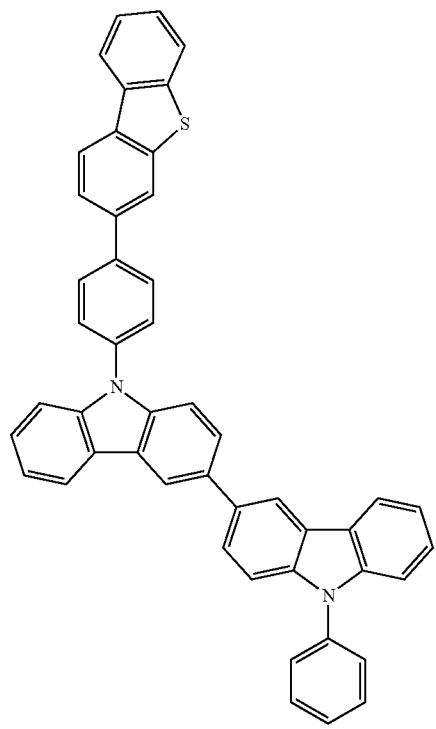
GHA-38
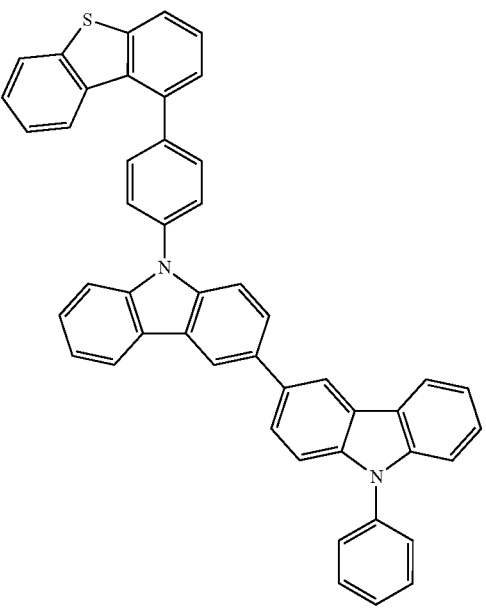
GHA-37
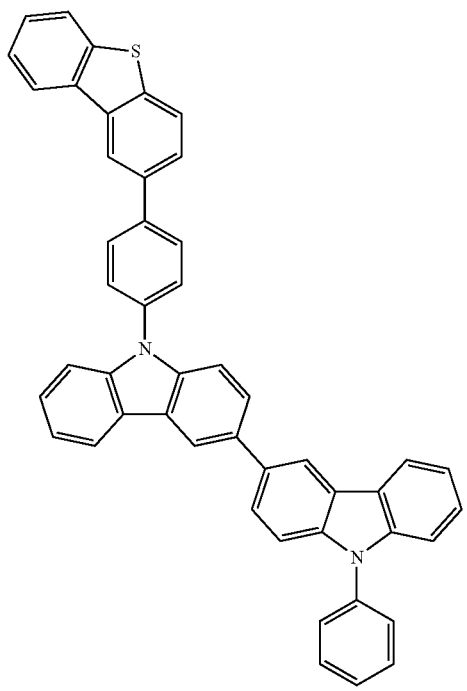
GHA-39
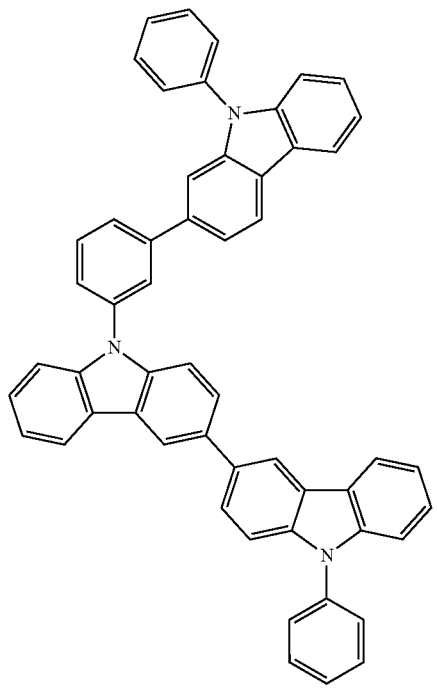

GHA-40
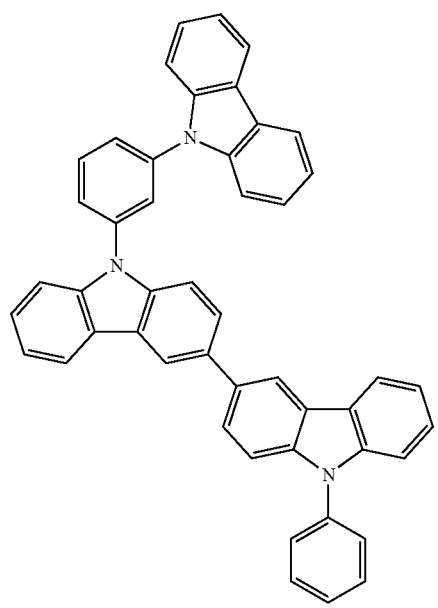
GHA-42
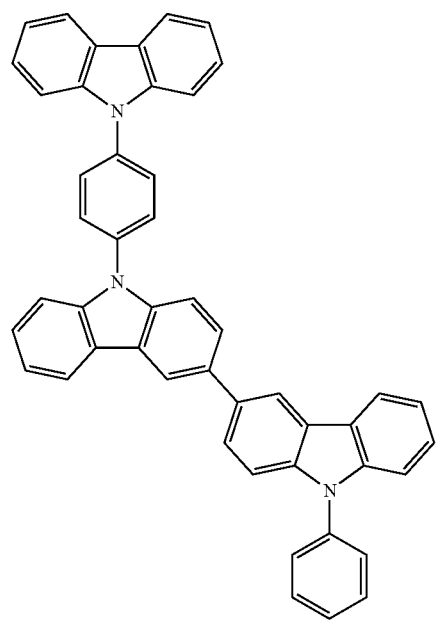
GHA-41
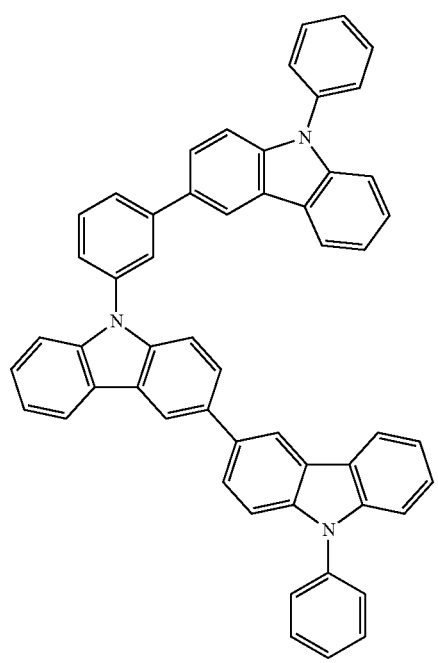
GHA-43
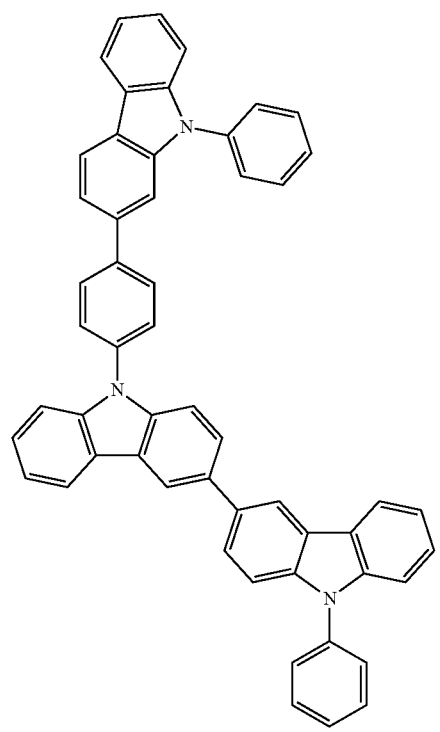

GHA-44
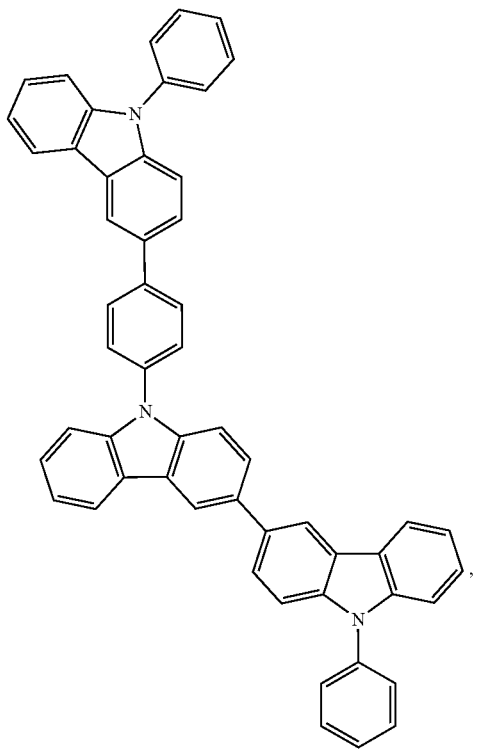
wherein the second green host compound is a compound represented by at least one of the following compounds:
GHB-2
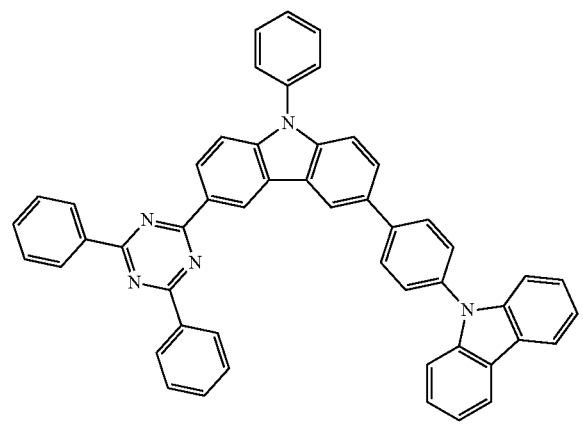
GHB-3
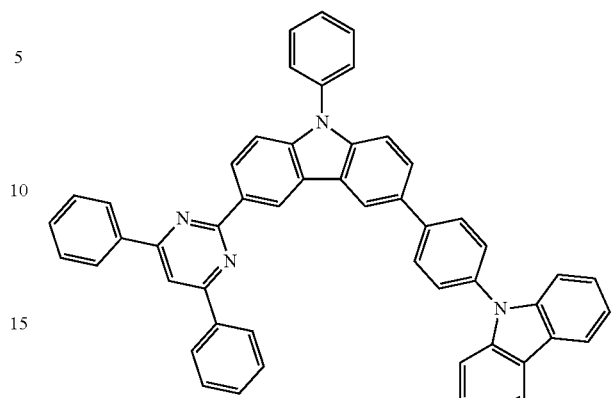
GHB-4
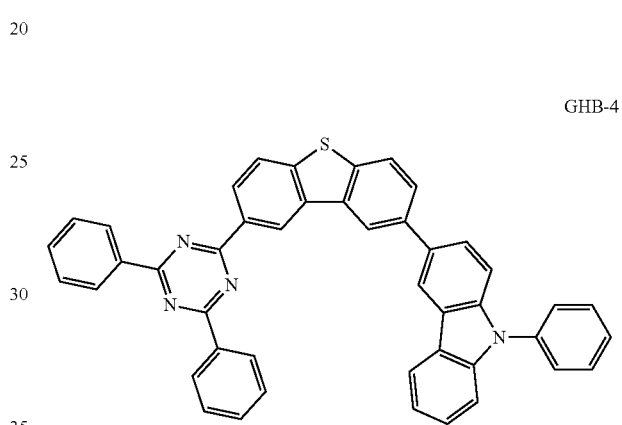
GHB-5
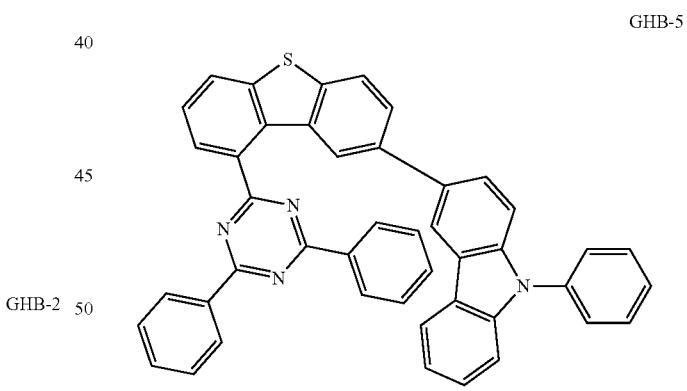
GHB-6
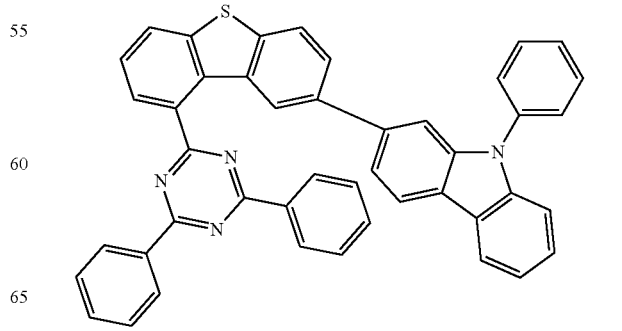

-continued
GHB-7
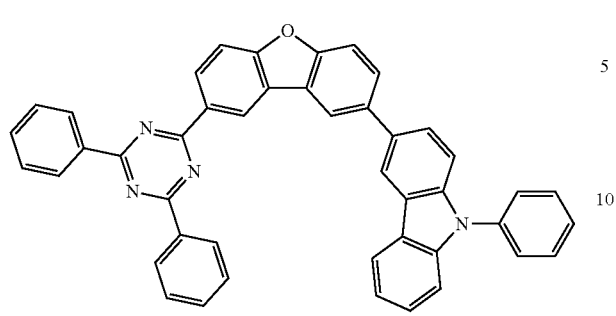
GHB-8
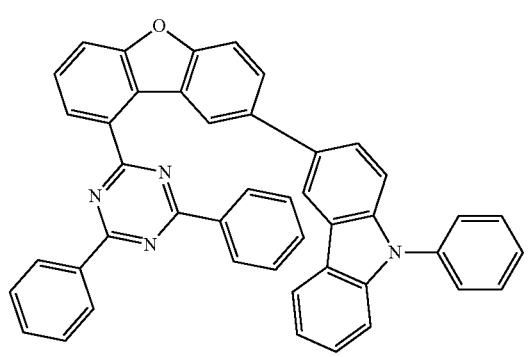
GHB-9
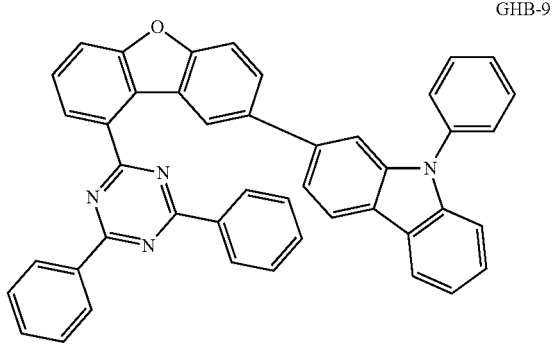
GHB-10
GHB-11
GHB-12
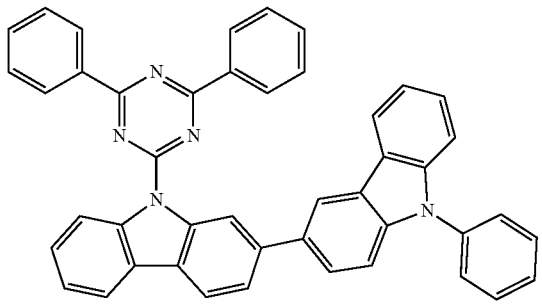

GHB-13
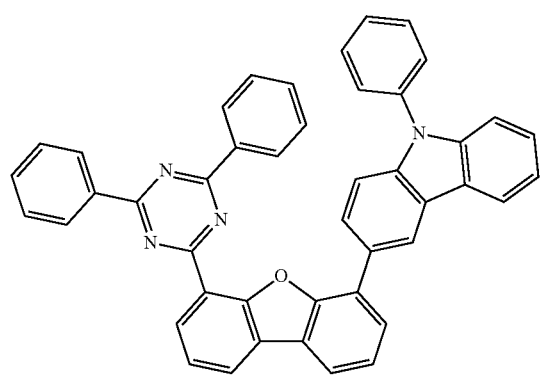
GHB-14
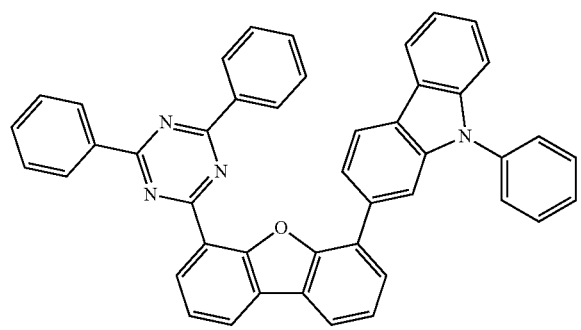
GHB-15
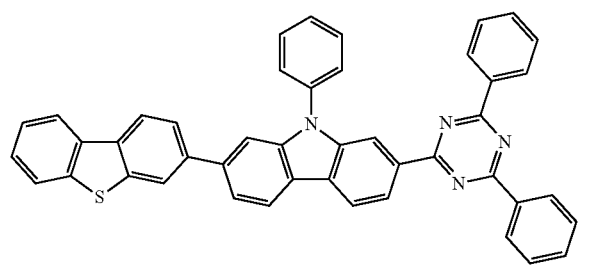
GHB-16
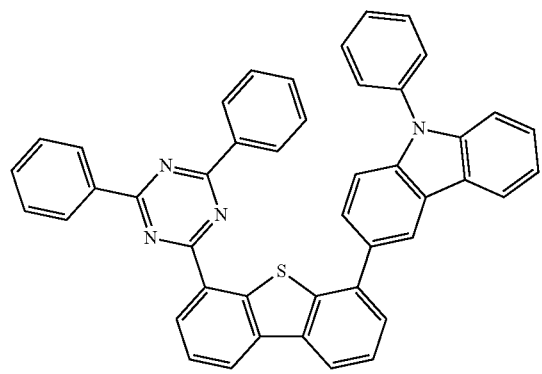
GHB-17
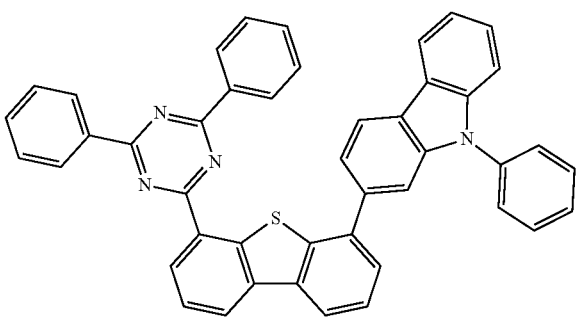
GHB-18
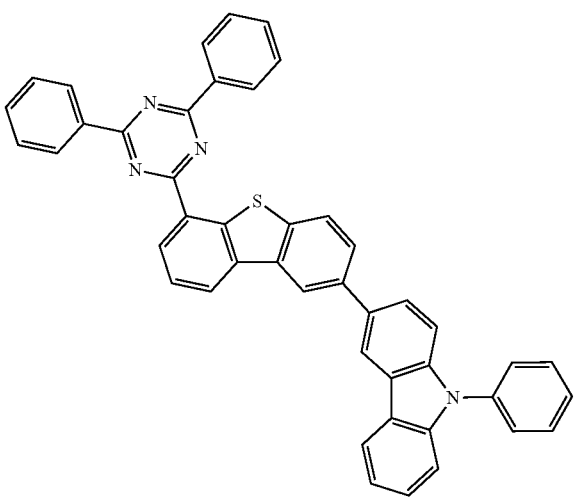
GHB-19

GHB-20

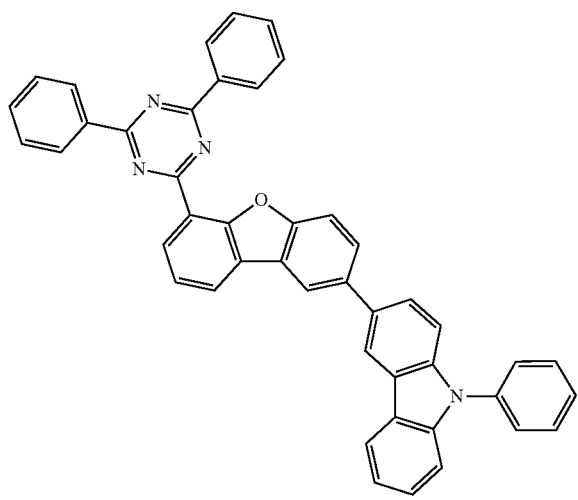

wherein the red phosphorescent dopant compound comprises at least one compound represented by Chemical Formula 4 or a compound represented by Chemical Formula 5, wherein the green phosphorescent dopant includes at least one of a compound represented by Chemical Formula 6 or a compound represented by Chemical Formula 7:

<Chemical Formula 4>

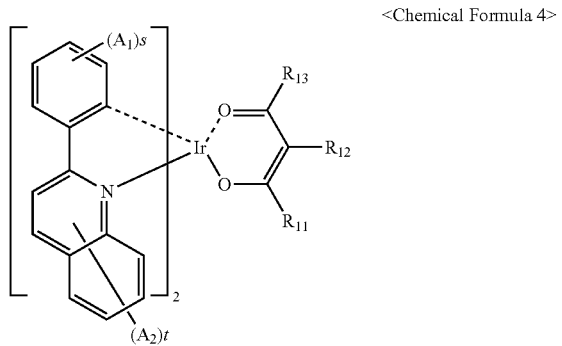

wherein, in the Chemical Formula 4, each of $A_1$ and $A_2$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 4, s denotes an integer of 1 to 4, t denotes an integer from 1 to 6, and each of $R_{11}$, $R_{12}$, and $R_{13}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{11}$ and $R_{12}$ are or $R_{12}$ and $R_{13}$ are connected to each other to form a ring, <Chemical Formula 5>

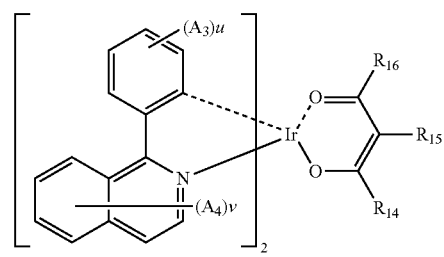

wherein, in the Chemical Formula 5, each of $A_3$ and $A_4$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 5, u denotes an integer of 1 to 4, v denotes an integer from 1 to 6, and each of $R_{14}$, $R_{15}$, and $R_{16}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{14}$ and $R_{15}$ are or $R_{15}$ and $R_{16}$ are connected to each other to form a ring, <Chemical Formula 6>

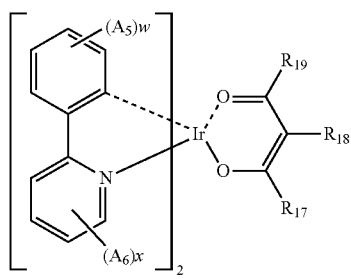

wherein, in the Chemical Formula 6, each of $A_5$ and $A_6$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 6, each of w and x independently denotes an integer of 1 to 4, and each of $R_{17}$, $R_{18}$, and $R_{19}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{17}$ and $R_{18}$ are or $R_{18}$ and $R_{19}$ are connected to each other to form a ring, <Chemical Formula 7>

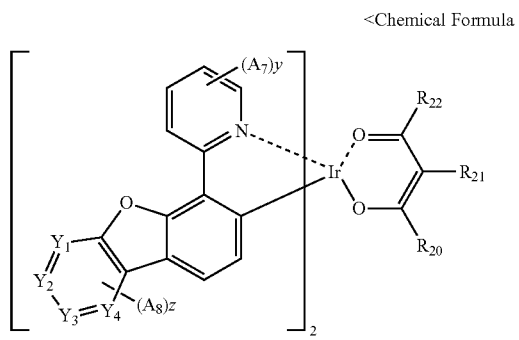

wherein, in the Chemical Formula 7, each of $A_7$ and $A_8$ independently represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, a substituted or unsubstituted C5 to C9 heteroaryl group, a substituted or unsubstituted carbazole group, a substituted or unsubstituted dibenzofuranyl group, a substituted or unsubstituted dibenzothiophenyl group, a substituted or unsubstituted trialkylsilyl group, and a substituted or unsubstituted triarylsilyl group, wherein, in the Chemical Formula 7, y denotes an integer of 1 to 4, z denotes an integer from 1 to 3, and each of $R_{20}$, $R_{21}$, and $R_{22}$ independently represents one selected from the group consisting of hydrogen, a substituted or unsubstituted C1 to C6 alkyl group, a substituted or unsubstituted C1 to C6 cycloalkyl group, and a substituted or unsubstituted C6 to C10 aryl group, wherein $R_{20}$ and $R_{21}$ are or $R_{21}$ and $R_{22}$ are connected to each other to form a ring, and wherein, in the Chemical Formula 7, each of $Y_1$, $Y_2$, $Y_3$, and $Y_4$ independently represents N or CR', wherein R' represents one selected from the group consisting of hydrogen, deuterium, halogen, a substituted or unsubstituted C1 to C6 alkyl group, a substituted or unsubstituted C3 to C6 cycloalkyl group, a substituted or unsubstituted C6 to C10 aryl group, and a substituted or unsubstituted C5 to C9 heteroaryl group.

12. The organic electroluminescence device of claim 11, further comprising an electron transport layer, and wherein the electron transport layer comprises a compound of Chemical Formula (III):

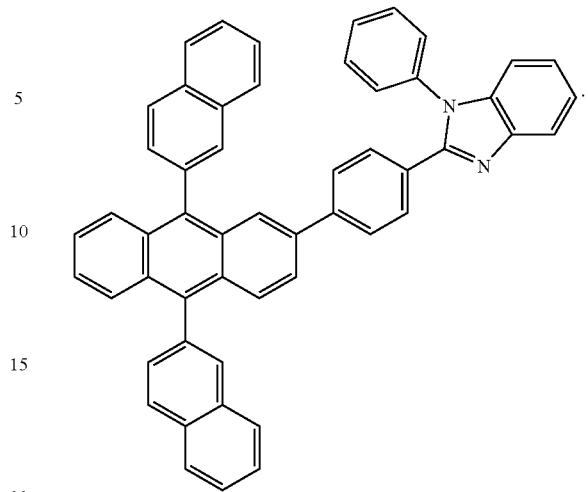

further comprising a hole transport layer, and wherein the hole transport layer comprises a compound of Chemical Formula (II):

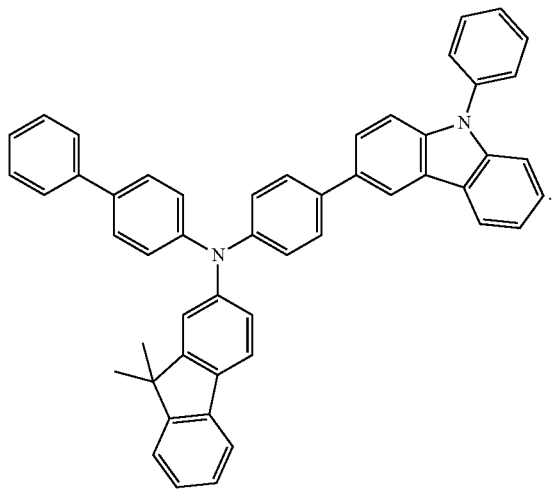 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

13. The organic electroluminescence device of claim 11, wherein the blue light-emission layer comprises a blue host compound and a blue dopant compound,
wherein the blue host compound comprises an anthracene based compound, and
wherein the blue dopant compound comprises a pyrene based dopant compound or a boron-containing dopant compound.

14. The organic electroluminescence device of claim 11, wherein the stack of the blue light-emission layer further comprises a hole transport layer and an electron transport layer,
wherein the hole transport layer, the blue light-emission layer, and the electron transport layer are sequentially stacked.

15. The organic electroluminescence device of claim 11, wherein a thickness of the red light-emitting layer is in a range of 10 nm to 20 nm, wherein the green light-emitting layer has a thickness in a range of 20 nm to 40 nm.

* * * * *